United States Patent
Schaapveld et al.

(10) Patent No.: US 9,161,947 B2
(45) Date of Patent: Oct. 20, 2015

(54) MIRNA MOLECULE DEFINED BY ITS SOURCE AND ITS DIAGNOSTIC AND THERAPEUTIC USES IN DISEASES OR CONDITIONS ASSOCIATED WITH EMT

(75) Inventors: Roeland Quirinus Jozef Schaapveld, Bussum (NL); Gerardus Wihelmus Christiaan Theodoor Verhaegh, Molenhoek (NL); Jacobus Antonius Schalken, Nijmegen (NL); Andreas Alphons van Puijenbroek, Boxtel (NL); Willemjin Maria Gommans, Voorschoten (NL); Sanne Weijzen, Bilthoven (NL)

(73) Assignee: INTERNA TECHNOLOGIES B.V., Nijmegen (NL)

( * ) Notice: Subject to any disclaimer, the term of this patent is extended or adjusted under 35 U.S.C. 154(b) by 0 days.

(21) Appl. No.: 13/603,300

(22) Filed: Sep. 4, 2012

(65) Prior Publication Data

US 2013/0072545 A1 Mar. 21, 2013

Related U.S. Application Data

(63) Continuation of application No. PCT/NL2011/050152, filed on Mar. 4, 2011.

(60) Provisional application No. 61/310,452, filed on Mar. 4, 2010.

(30) Foreign Application Priority Data

Mar. 4, 2010 (EP) ..................................... 10155512

(51) Int. Cl.
- *C12N 15/11* (2006.01)
- *C12Q 1/68* (2006.01)
- *A61K 31/7088* (2006.01)
- *A61K 31/7105* (2006.01)
- *C12N 15/113* (2010.01)

(52) U.S. Cl.
CPC ......... *A61K 31/7088* (2013.01); *A61K 31/7105* (2013.01); *C12N 15/113* (2013.01); *C12N 2310/141* (2013.01)

(58) Field of Classification Search
CPC ........... C12Q 2600/178; C12Q 1/6886; C12Q 2525/207; C12Q 1/6883; G01N 33/57434
See application file for complete search history.

(56) References Cited

FOREIGN PATENT DOCUMENTS

| EP | 2 208 499 A1 | 7/2010 |
|----|----|----|
| WO | WO 2005111211 A2 * | 11/2005 |
| WO | WO 2006137941 A2 * | 12/2006 |
| WO | 2007/148235 A2 | 12/2007 |
| WO | WO 2008142567 A2 * | 11/2008 |
| WO | 2009/044899 A1 | 4/2009 |

OTHER PUBLICATIONS

Godlewski et al, Targeting of the Bmi-1 Oncogene/Stem Cell Renewal Factor by MicroRNA-128 Inhibits Glioma Proliferation and Self-Renewal, published online Nov. 2008, Cancer Research, 68: 9125-9130.*

Huang et al, Microarray analysis of microRNA expression in hepatocellular carcinoma and non-tumorous tissues without viral hepatitis, 2008, Journal of Gastroenterology and Hepatology, 23: 87-94.*

Rubin et al, E-Cadherin Expression in Prostate Cancer: A Broad Survey Using High-Density Tissue Microarray Technology, 2001, Human Pathology, vol. 32, 7:690-697.*

Cervigne et al., "Identification of microRNA signature associated with progression of leukoplakia to oral carcinoma", Human Molecular Genetics, 2009, vol. 18, No. 24, p. 4818-4829.

Mueller et al., "miRNA expression profiling in melanocytes and melanoma cell lines reveals miRNAs associated with formation and progression of malignant melanoma", Journal of investigative dermatology, 2009, vol. 129, No. 7, p. 1740-1751.

Nakano et al., "Functional screening identifies a microRNA, miR-491 that induces apoptosis by targeting Bcl-XL in colorectal cancer cells", Int. Journal of Cancer, 2009, vol. 127, No. 5, p. 1072-1080.

Korpal et al., "The miR-200 family inhibits epithelial-mesenchymal transition and cancer cell migration by direct targeting of E-cadherin transcriptional repressors ZEB1 and ZEB2*", Journal of Biological Chemistry, 2008, vol. 283, No. 22, p. 14910-14914.

Gregory at al., "The miR-200 family and the miR-205 regulate epithelial to mesenchymal transition by targeting ZEB1 and SIP1", Nature Cell Biology, 2008, vol. 10, No. 5, p. 593-601.

* cited by examiner

*Primary Examiner* — Tracy Vivlemore
*Assistant Examiner* — Kate Poliakova
(74) *Attorney, Agent, or Firm* — Morgan Lewis & Bockius LLP

(57) ABSTRACT

The invention relates to the diagnostic and therapeutic uses of a miRNA molecule or an equivalent thereof wherein a source of said miRNA molecule or equivalent thereof comprises at least 80 nucleotides and comprises a motif having at least 98% identity with the motif represented by SEQ ID NO:1 or a source thereof in a disease and condition associated with EMT (Epithelial to Mesenchymal Transition).

20 Claims, 6 Drawing Sheets

```
                         SEQUENCE LISTING

<160> NUMBER OF SEQ ID NOS: 163

<210> SEQ ID NO 1
<211> LENGTH: 82
<212> TYPE: RNA
<213> ORGANISM: Artificial Sequence
<220> FEATURE:
<223> OTHER INFORMATION: motif
<220> FEATURE:
<221> NAME/KEY: misc_feature
<222> LOCATION: (4)..(4)
<223> OTHER INFORMATION: n may be A, U, C, G
<220> FEATURE:
<221> NAME/KEY: misc_feature
<222> LOCATION: (11)..(11)
<223> OTHER INFORMATION: n may be A, U, C, G
<220> FEATURE:
<221> NAME/KEY: misc_feature
<222> LOCATION: (16)..(16)
<223> OTHER INFORMATION: n may be A, U, C, G
<220> FEATURE:
<221> NAME/KEY: misc_feature
<222> LOCATION: (17)..(17)
<223> OTHER INFORMATION: n may be A, U, C, G
<220> FEATURE:
<221> NAME/KEY: misc_feature
<222> LOCATION: (19)..(19)
<223> OTHER INFORMATION: n is a, c, g, or u
<220> FEATURE:
<221> NAME/KEY: misc_feature
<222> LOCATION: (28)..(28)
<223> OTHER INFORMATION: n may be A, U, C, G
<220> FEATURE:
<221> NAME/KEY: misc_feature
<222> LOCATION: (35)..(35)
<223> OTHER INFORMATION: n may be A, U, C, G
<220> FEATURE:
<221> NAME/KEY: misc_feature
<222> LOCATION: (37)..(37)
<223> OTHER INFORMATION: n may be A, U, C, G
<220> FEATURE:
<221> NAME/KEY: misc_feature
<222> LOCATION: (41)..(41)
<223> OTHER INFORMATION: n may be A, U, C, G
<220> FEATURE:
<221> NAME/KEY: misc_feature
<222> LOCATION: (42)..(42)
<223> OTHER INFORMATION: n may be A, U, C, G
<220> FEATURE:
<221> NAME/KEY: misc_feature
<222> LOCATION: (45)..(45)
<223> OTHER INFORMATION: n may be A, U, C, G
<220> FEATURE:
<221> NAME/KEY: misc_feature
<222> LOCATION: (51)..(51)
<223> OTHER INFORMATION: n may be A, U, C, G
<220> FEATURE:
<221> NAME/KEY: misc_feature
<222> LOCATION: (52)..(52)
<223> OTHER INFORMATION: n may be A, U, C, G
<220> FEATURE:
<221> NAME/KEY: misc_feature
<222> LOCATION: (54)..(54)
<223> OTHER INFORMATION: n may be A, U, C, G
<220> FEATURE:
<221> NAME/KEY: misc_feature
<222> LOCATION: (56)..(56)
<223> OTHER INFORMATION: n may be A, U, C, G
<220> FEATURE:
<221> NAME/KEY: misc_feature
<222> LOCATION: (60)..(60)
<223> OTHER INFORMATION: n may be A, U ,C , G
```

```
<220> FEATURE:
<221> NAME/KEY: misc_feature
<222> LOCATION: (63)..(63)
<223> OTHER INFORMATION: n may be A, U, C, G
<220> FEATURE:
<221> NAME/KEY: misc_feature
<222> LOCATION: (67)..(67)
<223> OTHER INFORMATION: n may be A, U, C, G
<220> FEATURE:
<221> NAME/KEY: misc_feature
<222> LOCATION: (71)..(71)
<223> OTHER INFORMATION: n may be A, U, C, G
<220> FEATURE:
<221> NAME/KEY: misc_feature
<222> LOCATION: (72)..(72)
<223> OTHER INFORMATION: n may be A, U, C, G
<220> FEATURE:
<221> NAME/KEY: misc_feature
<222> LOCATION: (77)..(77)
<223> OTHER INFORMATION: n may be A, U, C, G

<400> SEQUENCE: 1
ucangcugug ncccunnana gggaagcncu uucununguc nnaangaaaa nnangngcun      60
ccnuuungag nnuuacnguu ug                                              82

<210> SEQ ID NO 2
<211> LENGTH: 20
<212> TYPE: RNA
<213> ORGANISM: Homo sapiens

<400> SEQUENCE: 2
uaaggcacgc ggugaaugcc                                                 20

<210> SEQ ID NO 3
<211> LENGTH: 22
<212> TYPE: RNA
<213> ORGANISM: Homo Sapiens

<400> SEQUENCE: 3
cguguucaca gcggaccuug au                                              22

<210> SEQ ID NO 4
<211> LENGTH: 23
<212> TYPE: RNA
<213> ORGANISM: Homo sapiens

<400> SEQUENCE: 4
aacauucaac gcugucggug agu                                             23

<210> SEQ ID NO 5
<211> LENGTH: 22
<212> TYPE: RNA
<213> ORGANISM: Homo sapiens

<400> SEQUENCE: 5
accaucgacc guugauugua cc                                              22

<210> SEQ ID NO 6
<211> LENGTH: 22
<212> TYPE: RNA
<213> ORGANISM: Homo sapiens

<400> SEQUENCE: 6
uaacacuguc ugguaaagau gg                                              22

<210> SEQ ID NO 7
```

```
<211> LENGTH: 22
<212> TYPE: RNA
<213> ORGANISM: Homo sapiens

<400> SEQUENCE: 7
caucuuccag uacaguguug ga                                          22

<210> SEQ ID NO 8
<211> LENGTH: 22
<212> TYPE: RNA
<213> ORGANISM: Homo Sapiens

<400> SEQUENCE: 8
uaacacuguc ugguaacgau gu                                          22

<210> SEQ ID NO 9
<211> LENGTH: 22
<212> TYPE: RNA
<213> ORGANISM: Homo sapiens

<400> SEQUENCE: 9
caucuuaccg gacagugcug ga                                          22

<210> SEQ ID NO 10
<211> LENGTH: 22
<212> TYPE: RNA
<213> ORGANISM: Homo sapiens

<400> SEQUENCE: 10
uaauacugcc ugguaaugau ga                                          22

<210> SEQ ID NO 11
<211> LENGTH: 22
<212> TYPE: RNA
<213> ORGANISM: Homo sapiens

<400> SEQUENCE: 11
caucuuacug ggcagcauug ga                                          22

<210> SEQ ID NO 12
<211> LENGTH: 23
<212> TYPE: RNA
<213> ORGANISM: Homo sapiens

<400> SEQUENCE: 12
uaauacugcc ggguaaugau gga                                         23

<210> SEQ ID NO 13
<211> LENGTH: 22
<212> TYPE: RNA
<213> ORGANISM: Homo sapiens

<400> SEQUENCE: 13
cgucuuaccc agcaguguuu gg                                          22

<210> SEQ ID NO 14
<211> LENGTH: 22
<212> TYPE: RNA
<213> ORGANISM: Homo sapiens

<400> SEQUENCE: 14
uccuucauuc caccggaguc ug                                          22
```

```
<210> SEQ ID NO 15
<211> LENGTH: 21
<212> TYPE: RNA
<213> ORGANISM: Homo sapiens

<400> SEQUENCE: 15
gauuucagug gagugaaguu c                                              21

<210> SEQ ID NO 16
<211> LENGTH: 22
<212> TYPE: RNA
<213> ORGANISM: Homo sapiens

<400> SEQUENCE: 16
uaauacuguc ugguaaaacc gu                                             22

<210> SEQ ID NO 17
<211> LENGTH: 22
<212> TYPE: RNA
<213> ORGANISM: Homo sapiens

<400> SEQUENCE: 17
uggaauguaa ggaagugugu gg                                             22

<210> SEQ ID NO 18
<211> LENGTH: 22
<212> TYPE: RNA
<213> ORGANISM: Homo sapiens

<400> SEQUENCE: 18
caaagcgcuc cccuuuagag gu                                             22

<210> SEQ ID NO 19
<211> LENGTH: 22
<212> TYPE: RNA
<213> ORGANISM: Homo sapiens

<400> SEQUENCE: 19
aagugcuucc uuuuagaggg uu                                             22

<210> SEQ ID NO 20
<211> LENGTH: 22
<212> TYPE: RNA
<213> ORGANISM: Homo sapiens

<400> SEQUENCE: 20
cuacaaaggg aagcacuuuc uc                                             22

<210> SEQ ID NO 21
<211> LENGTH: 21
<212> TYPE: RNA
<213> ORGANISM: Homo sapiens

<400> SEQUENCE: 21
gaaggcgcuu cccuuuggag u                                              21

<210> SEQ ID NO 22
<211> LENGTH: 85
<212> TYPE: RNA
<213> ORGANISM: homo sapiens

<400> SEQUENCE: 22
aggccucucu cuccguguuc acagcggacc uugauuuaaa uguccauaca auuaaggcac    60
```

```
gcggugaaug ccaagaaugg ggcug                                          85

<210> SEQ ID NO 23
<211> LENGTH: 109
<212> TYPE: RNA
<213> ORGANISM: homo sapiens

<400> SEQUENCE: 23
aucaagauua gaggcucugc ucuccguguu cacagcggac cuugauuuaa ugcauacaa    60 uuaaggcacg cggugaaugc caagagcgga gccuacggcu gcacuugaa               109

<210> SEQ ID NO 24
<211> LENGTH: 87
<212> TYPE: RNA
<213> ORGANISM: homo sapiens

<400> SEQUENCE: 24
ugagggcccc ucugcguguu cacagcggac cuugauuuaa ugucuauaca auuaaggcac   60
gcggugaaug ccaagagagg cgccucc                                       87

<210> SEQ ID NO 25
<211> LENGTH: 110
<212> TYPE: RNA
<213> ORGANISM: homo sapiens

<400> SEQUENCE: 25
ugaguuuuga gguugcuuca gugaacauuc aacgcugucg gugaguuugg aauuaaaauc   60
aaaaccaucg accguugauu guacccuaug gcuaaccauc aucuacucca              110

<210> SEQ ID NO 26
<211> LENGTH: 95
<212> TYPE: RNA
<213> ORGANISM: homo sapiens

<400> SEQUENCE: 26
cggccggccc uggguccauc uuccaguaca gucuuggaug gucuaauugu gaagcuccua   60
acacugucug guaaagaugg cucccgggug gguuc                              95

<210> SEQ ID NO 27
<211> LENGTH: 90
<212> TYPE: RNA
<213> ORGANISM: homo sapiens

<400> SEQUENCE: 27
ccgggccccu gugagcaucu uaccggacag ugcuggauuu cccagcuuga cucuaacacu   60
gucugguaac gauguucaaa ggugacccgc                                    90

<210> SEQ ID NO 28
<211> LENGTH: 68
<212> TYPE: RNA
<213> ORGANISM: homo sapiens

<400> SEQUENCE: 28
cccucgucuu acccagcagu guuggguugc gguuggagu cucuaauacu gccgguaau     60 gauggagg                                                            68

<210> SEQ ID NO 29
<211> LENGTH: 110
<212> TYPE: RNA
<213> ORGANISM: homo sapiens
```

```
<400> SEQUENCE: 29
aaagauccuc agacaaucca ugugcuucuc uugccuuca uuccaccgga gucugucuca    60
uacccaacca gauuucagug gagugaaguu caggaggcau ggagcugaca             110

<210> SEQ ID NO 30
<211> LENGTH: 70
<212> TYPE: RNA
<213> ORGANISM: homo sapiens

<400> SEQUENCE: 30
gcgucuuacc agacauggu agaccuggcc cucugucuaa uacugucugg uaaaaccguc    60
cauccgcugc                                                         70

<210> SEQ ID NO 31
<211> LENGTH: 86
<212> TYPE: RNA
<213> ORGANISM: homo sapiens

<400> SEQUENCE: 31
ugcuucccga ggccacaugc uucuuuauau ccccauaugg auuacuuugc uauggaaugu    60
aaggaagugu gugguuucgg caagug                                       86

<210> SEQ ID NO 32
<211> LENGTH: 83
<212> TYPE: RNA
<213> ORGANISM: homo sapiens

<400> SEQUENCE: 32
ucaugcugug gcccuccaga gggaagcgcu uucguuguc ugaaagaaaa caaagcgcuc    60
cccuuuagag guuuacgguu uga                                          83

<210> SEQ ID NO 33
<211> LENGTH: 87
<212> TYPE: RNA
<213> ORGANISM: homo sapiens

<400> SEQUENCE: 33
ucucaggcug ugacccucua aagggaagcg cuuucgugg ucagaaagaa aagcaagugc    60
uuccuuuuag agguuaccg uuuggga                                       87

<210> SEQ ID NO 34
<211> LENGTH: 87
<212> TYPE: RNA
<213> ORGANISM: homo sapiens

<400> SEQUENCE: 34
ucucaugcug ugacccuaca aagggaagca cuuucucuug uccaaaggaa agaaggcgc    60 uucccuuugg aguguuacgg uuugaga                                      87

<210> SEQ ID NO 35
<211> LENGTH: 95
<212> TYPE: RNA
<213> ORGANISM: homo sapiens

<400> SEQUENCE: 35
ccagcucggg cagccgugc caucuuacug ggcagcauug gauggaguca ggucucuaau    60
acugccuggu aaugaugacg gcggagcccu gcacg                             95
```

```
<210> SEQ ID NO 36
<211> LENGTH: 180
<212> TYPE: DNA
<213> ORGANISM: artificial sequence
<220> FEATURE:
<223> OTHER INFORMATION: miR-124-1 as cloned into lentiviral vector

<400> SEQUENCE: 36
tttctttcac ctttccttcc ttccttcctc ctttccttcc tcaggagaaa ggcctctctc      60
tccgtgttca cagcggacct tgatttaaat gtccatacaa ttaaggcacg cggtgaatgc     120
caagaatggg gctggctgag caccgtgggt cggcgagggc cgccaagga aggagcgacc     180

<210> SEQ ID NO 37
<211> LENGTH: 205
<212> TYPE: DNA
<213> ORGANISM: artificial sequence
<220> FEATURE:
<223> OTHER INFORMATION: miR-181a-1 as cloned into lentiviral vector

<400> SEQUENCE: 37
gttgtttctg tctcccatcc ccttcagata cttacagata ctgtaaagtg agtagaattc      60
tgagttttga ggttgcttca gtgaacattc aacgctgtcg gtgagtttgg aattaaaatc     120
aaaaccatcg accgttgatt gtaccctatg gctaaccatc atctactcca tggtgctcag     180
aattcgctga agacaggaaa ccaaa                                           205

<210> SEQ ID NO 38
<211> LENGTH: 200
<212> TYPE: DNA
<213> ORGANISM: artificial sequence
<220> FEATURE:
<223> OTHER INFORMATION: miR-141 as cloned into lentiviral vector

<400> SEQUENCE: 38
cctgtagcaa ctggtgagcg cgcaccgtag ttctctgtcg gccggccctg ggtccatctt      60
ccagtacagt gttggatggt ctaattgtga agctcctaac actgtctggt aaagatggct     120
cccgggtggg ttctctcggc agtaaccttc agggagccct gaagaccatg gaggactact     180
gaccaacaac ctctgacctt                                                 200

<210> SEQ ID NO 39
<211> LENGTH: 191
<212> TYPE: DNA
<213> ORGANISM: artificial sequence
<220> FEATURE:
<223> OTHER INFORMATION: miR-200a as cloned into lentiviral vector

<400> SEQUENCE: 39
gttcttccct gggcttccac agcagcccct gcctgcctgg cgggacccca cgtccctccc      60
gggcccctgt gagcatctta ccggacagtg ctggatttcc cagcttgact ctaacactgt     120
ctggtaacga tgttcaaagg tgacccgccg ctcgccgggg acaccaccga ggcacatccg     180
gagctcctac t                                                          191

<210> SEQ ID NO 40
<211> LENGTH: 140
<212> TYPE: DNA
<213> ORGANISM: artificial sequence
<220> FEATURE:
<223> OTHER INFORMATION: miR-200c as cloned into lentiviral vector

<400> SEQUENCE: 40
```

```
aagctgcctg acccaaggtg ggcgggctgg gcggggccc tcgtcttacc cagcagtgtt      60
tgggtgcggt tgggagtctc taatactgcc gggtaatgat ggaggcccct gtccctgtgt    120
cagcaacatc catcgcctca                                                140

<210> SEQ ID NO 41
<211> LENGTH: 253
<212> TYPE: DNA
<213> ORGANISM: artificial sequence
<220> FEATURE:
<223> OTHER INFORMATION: miR-205 as cloned into lentiviral vector

<400> SEQUENCE: 41
agtgtctaca ggctgaggtt gacatgcatc cccaccctct gagaaaaaga tcctcagaca     60
atccatgtgc ttctcttgtc cttcattcca ccggagtctg tctcataccc aaccagattt   120
cagtggagtg aagttcagga ggcatggagc tgacaaccat gaggcctcgg cagccaccgc   180
caccaccgcc gccgccacca ccgtagcagc agcagcagca gcagcagcag cagcagcagc   240
agcaagagta act                                                      253

<210> SEQ ID NO 42
<211> LENGTH: 175
<212> TYPE: DNA
<213> ORGANISM: artificial sequence
<220> FEATURE:
<223> OTHER INFORMATION: miR-429 as cloned into lentiviral vector

<400> SEQUENCE: 42
agacaccagc ccaggacccg gaggccaccc acaccaccgc cggccgatgg gcgtcttacc    60
agacatggtt agacctggcc ctctgtctaa tactgtctgg taaaaccgtc catccgctgc   120
ctgatcaccg ttagaggaga gagctgcctg ccctgcagct catcagtgca aagcc        175

<210> SEQ ID NO 43
<211> LENGTH: 202
<212> TYPE: DNA
<213> ORGANISM: artificial sequence
<220> FEATURE:
<223> OTHER INFORMATION: miR-206 as cloned into lentiviral vector

<400> SEQUENCE: 43
gcaaggagga aagatgctac aagtgggccca cttctgagat gcgggctgct tctggatgac    60
actgcttccc gaggccacat gcttctttat atccccatat ggattacttt gctatggaat   120
gtaaggaagt gtgtggtttc ggcaagtgcc tcctcgctgg ccccagggta ccacccggag   180
cacaggtttg gtgaccttct tc                                            202

<210> SEQ ID NO 44
<211> LENGTH: 251
<212> TYPE: DNA
<213> ORGANISM: artificial sequence
<220> FEATURE:
<223> OTHER INFORMATION: miR-518b as cloned into lentiviral vector

<400> SEQUENCE: 44
gcaaacaggg caaataaatg catctttatt ttgtgtccat tttaacctgg tcaaggaaaa     60
ttccaacagc aacatcaaaa aaccagtgtt ggagcaagaa tatgtcatgc tgtggccctc   120
cagagggaag cgctttctgt tgtctgaaag aaaacaaagc gctcccctt agaggtttac    180 ggtttgagta aagcagcgtt gaagttgatg ctgatcttgg taatacattt gcagagcgtg   240
```

```
cttatcatca g                                                          251

<210> SEQ ID NO 45
<211> LENGTH: 214
<212> TYPE: DNA
<213> ORGANISM: artificial sequence
<220> FEATURE:
<223> OTHER INFORMATION: miR-520f as cloned into lentiviral vector

<400> SEQUENCE: 45
tgtgtccatt taaacctggt caaggaagat tcccacaaaa aatccacggt gctggagcaa     60
gaggatctca ggctgtgacc ctctaaaggg aagcgctttc tgtggtcaga aagaaaagca    120
agtgcttcct tttagagggt taccgtttgg gaaaagcaat gttgaagttg atgctgatct    180
tggtaaaata tttgcagagc gtgcttatca tcag                                214

<210> SEQ ID NO 46
<211> LENGTH: 253
<212> TYPE: DNA
<213> ORGANISM: artificial sequence
<220> FEATURE:
<223> OTHER INFORMATION: miR-524 as cloned into lentiviral vector

<400> SEQUENCE: 46
caaacagggc caataaatgc atcctcattt ttgtgtccat tttaacctgg gcaaggaaaa     60
ttccaacaaa aaacccagag ttctggagca agaagatctc atgctgtgac cctacaaagg    120
gaagcacttt ctcttgtcca aggaaaagaa aggcgcttcc ctttggagtg ttacggtttg    180
agaaaagcag cgttgaagtt gatgcttatc tcggtaatac atttgtagag catgcttatc    240
atgaggcttg gac                                                       253

<210> SEQ ID NO 47
<211> LENGTH: 135
<212> TYPE: DNA
<213> ORGANISM: artificial sequence
<220> FEATURE:
<223> OTHER INFORMATION: miR-200b as cloned into lentiviral vector

<400> SEQUENCE: 47
cagccgggcg gccccggac ccagctcggg cagccgtggc catcttactg ggcagcattg      60
gatggagtca ggtctctaat actgcctggt aatgatgacg gcggagccct gcacgcagcg    120
accggccgac cccgt                                                     135

<210> SEQ ID NO 48
<211> LENGTH: 18
<212> TYPE: DNA
<213> ORGANISM: artificial sequence
<220> FEATURE:
<223> OTHER INFORMATION: E-Cadherin forward1 primer

<400> SEQUENCE: 48
gaaaagagag tggaagtg                                                   18

<210> SEQ ID NO 49
<211> LENGTH: 18
<212> TYPE: DNA
<213> ORGANISM: artificial sequence
<220> FEATURE:
<223> OTHER INFORMATION: E-Cadherin reverse1 primer

<400> SEQUENCE: 49
gtgaagggag atgtattg                                                   18
```

<210> SEQ ID NO 50
<211> LENGTH: 20
<212> TYPE: DNA
<213> ORGANISM: artificial sequence
<220> FEATURE:
<223> OTHER INFORMATION: E-Cadherin forward2 primer

<400> SEQUENCE: 50
caggtctcct cttggctctg                                                    20

<210> SEQ ID NO 51
<211> LENGTH: 20
<212> TYPE: DNA
<213> ORGANISM: artificial sequence
<220> FEATURE:
<223> OTHER INFORMATION: E-Cadherin reverse2 primer

<400> SEQUENCE: 51
actttgaatc gggtgtcgag                                                    20

<210> SEQ ID NO 52
<211> LENGTH: 20
<212> TYPE: DNA
<213> ORGANISM: artificial sequence
<220> FEATURE:
<223> OTHER INFORMATION: N-Cadherin forward primer

<400> SEQUENCE: 52
gaggattagc cggaacaaca                                                    20

<210> SEQ ID NO 53
<211> LENGTH: 20
<212> TYPE: DNA
<213> ORGANISM: artificial sequence
<220> FEATURE:
<223> OTHER INFORMATION: N-Cadherin reverse primer

<400> SEQUENCE: 53
aacaaatttc ccccatctcc                                                    20

<210> SEQ ID NO 54
<211> LENGTH: 20
<212> TYPE: DNA
<213> ORGANISM: artificial sequence
<220> FEATURE:
<223> OTHER INFORMATION: SNAIL forward primer

<400> SEQUENCE: 54
aggatctcca ggctcgaaag                                                    20

<210> SEQ ID NO 55
<211> LENGTH: 20
<212> TYPE: DNA
<213> ORGANISM: artificial sequence
<220> FEATURE:
<223> OTHER INFORMATION: SNAIL reverse primer

<400> SEQUENCE: 55
gacatctgag tgggtctgga                                                    20

<210> SEQ ID NO 56
<211> LENGTH: 20
<212> TYPE: DNA
<213> ORGANISM: artificial sequence
<220> FEATURE:

<223> OTHER INFORMATION: SLUG forward primer

<400> SEQUENCE: 56
ttcggaccca cacattacct                                        20

<210> SEQ ID NO 57
<211> LENGTH: 20
<212> TYPE: DNA
<213> ORGANISM: artificial sequence
<220> FEATURE:
<223> OTHER INFORMATION: SLUG reverse primer

<400> SEQUENCE: 57
ttggagcagt ttttgcactg                                        20

<210> SEQ ID NO 58
<211> LENGTH: 20
<212> TYPE: DNA
<213> ORGANISM: artificial sequence
<220> FEATURE:
<223> OTHER INFORMATION: ZEB1 forward primer

<400> SEQUENCE: 58
atgcggaaga cagaaaatgg                                        20

<210> SEQ ID NO 59
<211> LENGTH: 20
<212> TYPE: DNA
<213> ORGANISM: artificial sequence
<220> FEATURE:
<223> OTHER INFORMATION: ZEB1 reverse primer

<400> SEQUENCE: 59
gtcacgttct tccgcttctc                                        20

<210> SEQ ID NO 60
<211> LENGTH: 20
<212> TYPE: DNA
<213> ORGANISM: artificial sequence
<220> FEATURE:
<223> OTHER INFORMATION: ZEB2 forward primer

<400> SEQUENCE: 60
cgcttgacat cactgaagga                                        20

<210> SEQ ID NO 61
<211> LENGTH: 20
<212> TYPE: DNA
<213> ORGANISM: artificial sequence
<220> FEATURE:
<223> OTHER INFORMATION: ZEB2 reverse primer

<400> SEQUENCE: 61
cttgccacac tctgtgcatt                                        20

<210> SEQ ID NO 62
<211> LENGTH: 21
<212> TYPE: DNA
<213> ORGANISM: artificial sequence
<220> FEATURE:
<223> OTHER INFORMATION: B2M forward primer

<400> SEQUENCE: 62
agcagagaat ggaaagtcaa a                                      21

<210> SEQ ID NO 63
<211> LENGTH: 18
<212> TYPE: DNA
<213> ORGANISM: artificial sequence
<220> FEATURE:
<223> OTHER INFORMATION: B2M reverse primer

<400> SEQUENCE: 63
tgctgcttac atgtctcg                                           18

<210> SEQ ID NO 64
<211> LENGTH: 50
<212> TYPE: DNA
<213> ORGANISM: artificial sequence
<220> FEATURE:
<223> OTHER INFORMATION: miR-141-specific stem-loop primer

<400> SEQUENCE: 64
gtcgtatcca gtgcagggtc cgaggtattc gcactggata cgacccatct        50

<210> SEQ ID NO 65
<211> LENGTH: 50
<212> TYPE: DNA
<213> ORGANISM: artificial sequence
<220> FEATURE:
<223> OTHER INFORMATION: miR-200c-specific stem-loop primer

<400> SEQUENCE: 65
gtcgtatcca gtgcagggtc cgaggtattc gcactggata cgactccatc        50

<210> SEQ ID NO 66
<211> LENGTH: 50
<212> TYPE: DNA
<213> ORGANISM: artificial sequence
<220> FEATURE:
<223> OTHER INFORMATION: miR-181a-1-specific stem-loop primer

<400> SEQUENCE: 66
gtcgtatcca gtgcagggtc cgaggtattc gcactggata cgacactcac        50

<210> SEQ ID NO 67
<211> LENGTH: 50
<212> TYPE: DNA
<213> ORGANISM: artificial sequence
<220> FEATURE:
<223> OTHER INFORMATION: miR-124-specific stem-loop primer

<400> SEQUENCE: 67
gtcgtatcca gtgcagggtc cgaggtattc gcactggata cgacggcatt        50

<210> SEQ ID NO 68
<211> LENGTH: 50
<212> TYPE: DNA
<213> ORGANISM: artificial sequence
<220> FEATURE:
<223> OTHER INFORMATION: miR-518b-specific stem-loop primer

<400> SEQUENCE: 68
gtcgtatcca gtgcagggtc cgaggtattc gcactggata cgacacctct        50

<210> SEQ ID NO 69
<211> LENGTH: 50
<212> TYPE: DNA
<213> ORGANISM: artificial sequence
<220> FEATURE:
<223> OTHER INFORMATION: miR-520f-specific stem-loop primer

<400> SEQUENCE: 69
gtcgtatcca gtgcagggtc cgaggtattc gcactggata cgacaaccct          50

<210> SEQ ID NO 70
<211> LENGTH: 50
<212> TYPE: DNA
<213> ORGANISM: artificial sequence
<220> FEATURE:
<223> OTHER INFORMATION: miR-524-5p-specific stem-loop primer

<400> SEQUENCE: 70
gtcgtatcca gtgcagggtc cgaggtattc gcactggata cgacgagaaa          50

<210> SEQ ID NO 71
<211> LENGTH: 50
<212> TYPE: DNA
<213> ORGANISM: artificial sequence
<220> FEATURE:
<223> OTHER INFORMATION: miR-524-3p-specific stem-loop primer

<400> SEQUENCE: 71
gtcgtatcca gtgcagggtc cgaggtattc gcactggata cgacactcca          50

<210> SEQ ID NO 72
<211> LENGTH: 24
<212> TYPE: DNA
<213> ORGANISM: artificial sequence
<220> FEATURE:
<223> OTHER INFORMATION: miR-141 forward primer

<400> SEQUENCE: 72
gcccgctaac actgtctggt aaag                                      24

<210> SEQ ID NO 73
<211> LENGTH: 24
<212> TYPE: DNA
<213> ORGANISM: artificial sequence
<220> FEATURE:
<223> OTHER INFORMATION: miR-200c forward primer

<400> SEQUENCE: 73
gcccgctaat actgccgggt aatg                                      24

<210> SEQ ID NO 74
<211> LENGTH: 23
<212> TYPE: DNA
<213> ORGANISM: artificial sequence
<220> FEATURE:
<223> OTHER INFORMATION: miR-181a-1 forward primer

<400> SEQUENCE: 74
tgccagaaca ttcaacgctg tcg                                       23

<210> SEQ ID NO 75
<211> LENGTH: 21
<212> TYPE: DNA
<213> ORGANISM: artificial sequence
<220> FEATURE:
<223> OTHER INFORMATION: miR-124 forward primer

<400> SEQUENCE: 75
tgccagtaag gcacgcggtg a                                         21

<210> SEQ ID NO 76
<211> LENGTH: 24

```
<212> TYPE: DNA
<213> ORGANISM: artificial sequence
<220> FEATURE:
<223> OTHER INFORMATION: miR-518b forward primer

<400> SEQUENCE: 76
tgccagcaaa gcgctcccct ttag                                      24

<210> SEQ ID NO 77
<211> LENGTH: 24
<212> TYPE: DNA
<213> ORGANISM: artificial sequence
<220> FEATURE:
<223> OTHER INFORMATION: miR-520f forward primer

<400> SEQUENCE: 77
gcccgcaagt gcttcctttt agag                                      24

<210> SEQ ID NO 78
<211> LENGTH: 23
<212> TYPE: DNA
<213> ORGANISM: artificial sequence
<220> FEATURE:
<223> OTHER INFORMATION: miR-524-5p forward primer

<400> SEQUENCE: 78
gcccgcctac aaagggaagc act                                       23

<210> SEQ ID NO 79
<211> LENGTH: 23
<212> TYPE: DNA
<213> ORGANISM: artificial sequence
<220> FEATURE:
<223> OTHER INFORMATION: miR-524-3p forward primer

<400> SEQUENCE: 79
tgccaggaag gcgcttccct ttg                                       23

<210> SEQ ID NO 80
<211> LENGTH: 16
<212> TYPE: DNA
<213> ORGANISM: artificial sequence
<220> FEATURE:
<223> OTHER INFORMATION: universal reverse primer

<400> SEQUENCE: 80
gtgcagggtc cgaggt                                               16

<210> SEQ ID NO 81
<211> LENGTH: 16
<212> TYPE: DNA
<213> ORGANISM: artificial sequence
<220> FEATURE:
<223> OTHER INFORMATION: U6 snRNA (RNA6-1) RT primer

<400> SEQUENCE: 81
gtcatccttg cgcagg                                               16

<210> SEQ ID NO 82
<211> LENGTH: 20
<212> TYPE: DNA
<213> ORGANISM: artificial sequence
<220> FEATURE:
<223> OTHER INFORMATION: U6 snRNA (RNA6-1) forward primer

<400> SEQUENCE: 82
```

```
cgcttcggca gcacatatac                                              20

<210> SEQ ID NO 83
<211> LENGTH: 20
<212> TYPE: DNA
<213> ORGANISM: artificial sequence
<220> FEATURE:
<223> OTHER INFORMATION: U6 snRNA (RNA6-1) reverse primer

<400> SEQUENCE: 83
aggggccatg ctaatcttct                                              20

<210> SEQ ID NO 84
<211> LENGTH: 23
<212> TYPE: DNA
<213> ORGANISM: artificial sequence
<220> FEATURE:
<223> OTHER INFORMATION: pCDH lentiviral vector-specific forward primer

<400> SEQUENCE: 84
cacgctgttt tgacctccat aga                                          23

<210> SEQ ID NO 85
<211> LENGTH: 18
<212> TYPE: DNA
<213> ORGANISM: artificial sequence
<220> FEATURE:
<223> OTHER INFORMATION: pCDH lentiviral vector-specific reverse primer

<400> SEQUENCE: 85
cactgacggg caccggag                                                18

<210> SEQ ID NO 86
<211> LENGTH: 28
<212> TYPE: DNA
<213> ORGANISM: artificial sequence
<220> FEATURE:
<223> OTHER INFORMATION: pCDH specific primer

<400> SEQUENCE: 86
gacctccata gaagattcta gagctagc                                     28

<210> SEQ ID NO 87
<211> LENGTH: 7
<212> TYPE: RNA
<213> ORGANISM: artificial sequence
<220> FEATURE:
<223> OTHER INFORMATION: mature miR-124 seed sequence

<400> SEQUENCE: 87 aaggcac                                                             7

<210> SEQ ID NO 88
<211> LENGTH: 7
<212> TYPE: RNA
<213> ORGANISM: artificial sequence
<220> FEATURE:
<223> OTHER INFORMATION: mature miR-124 seed sequence

<400> SEQUENCE: 88 guguuca                                                             7

<210> SEQ ID NO 89
<211> LENGTH: 7
<212> TYPE: RNA
<213> ORGANISM: artificial sequence
```

```
-continued

<220> FEATURE:
<223> OTHER INFORMATION: mature miR-181a seed sequence

<400> SEQUENCE: 89 acauuca                                                              7

<210> SEQ ID NO 90
<211> LENGTH: 7
<212> TYPE: RNA
<213> ORGANISM: artificial sequence
<220> FEATURE:
<223> OTHER INFORMATION: mature miR-181a seed sequence

<400> SEQUENCE: 90 ccaucga                                                              7

<210> SEQ ID NO 91
<211> LENGTH: 7
<212> TYPE: RNA
<213> ORGANISM: artificial sequence
<220> FEATURE:
<223> OTHER INFORMATION: mature miR-141 seed sequence

<400> SEQUENCE: 91 aacacug                                                              7

<210> SEQ ID NO 92
<211> LENGTH: 7
<212> TYPE: RNA
<213> ORGANISM: artificial sequence
<220> FEATURE:
<223> OTHER INFORMATION: mature miR-141 seed sequence

<400> SEQUENCE: 92 aucuucc                                                              7

<210> SEQ ID NO 93
<211> LENGTH: 7
<212> TYPE: RNA
<213> ORGANISM: artificial sequence
<220> FEATURE:
<223> OTHER INFORMATION: mature miR-200a seed sequence

<400> SEQUENCE: 93 aacacug                                                              7

<210> SEQ ID NO 94
<211> LENGTH: 7
<212> TYPE: RNA
<213> ORGANISM: artificial sequence
<220> FEATURE:
<223> OTHER INFORMATION: mature miR-200a seed sequence

<400> SEQUENCE: 94 aucuuac                                                              7

<210> SEQ ID NO 95
<211> LENGTH: 7
<212> TYPE: RNA
<213> ORGANISM: artificial sequence
<220> FEATURE:
<223> OTHER INFORMATION: mature miR-200b seed sequence

<400> SEQUENCE: 95 aauacug                                                              7
```

```
<210> SEQ ID NO 96
<211> LENGTH: 7
<212> TYPE: RNA
<213> ORGANISM: artificial sequence
<220> FEATURE:
<223> OTHER INFORMATION: mature miR-200b seed sequence

<400> SEQUENCE: 96 aucuuac                                                                    7

<210> SEQ ID NO 97
<211> LENGTH: 7
<212> TYPE: RNA
<213> ORGANISM: artificial sequence
<220> FEATURE:
<223> OTHER INFORMATION: mature miR-200c seed sequence

<400> SEQUENCE: 97 aauacug                                                                    7

<210> SEQ ID NO 98
<211> LENGTH: 7
<212> TYPE: RNA
<213> ORGANISM: artificial sequence
<220> FEATURE:
<223> OTHER INFORMATION: mature miR-200c seed sequence

<400> SEQUENCE: 98 gucuuac                                                                    7

<210> SEQ ID NO 99
<211> LENGTH: 7
<212> TYPE: RNA
<213> ORGANISM: artificial sequence
<220> FEATURE:
<223> OTHER INFORMATION: mature miR-205 seed sequence

<400> SEQUENCE: 99 ccuucau                                                                    7

<210> SEQ ID NO 100
<211> LENGTH: 7
<212> TYPE: RNA
<213> ORGANISM: artificial sequence
<220> FEATURE:
<223> OTHER INFORMATION: mature miR-205 seed sequence

<400> SEQUENCE: 100 auuucag                                                                    7

<210> SEQ ID NO 101
<211> LENGTH: 7
<212> TYPE: RNA
<213> ORGANISM: artificial sequence
<220> FEATURE:
<223> OTHER INFORMATION: mature miR-429 seed sequence

<400> SEQUENCE: 101 aauacug                                                                    7

<210> SEQ ID NO 102
<211> LENGTH: 7
<212> TYPE: RNA
<213> ORGANISM: artificial sequence
<220> FEATURE:
<223> OTHER INFORMATION: mature miR-206 seed sequence
```

```
<400> SEQUENCE: 102 ggaaugu                                                                    7

<210> SEQ ID NO 103
<211> LENGTH: 7
<212> TYPE: RNA
<213> ORGANISM: artificial sequence
<220> FEATURE:
<223> OTHER INFORMATION: mature miR-518b seed sequence

<400> SEQUENCE: 103 aaagcgc                                                                    7

<210> SEQ ID NO 104
<211> LENGTH: 7
<212> TYPE: RNA
<213> ORGANISM: artificial sequence
<220> FEATURE:
<223> OTHER INFORMATION: mature miR-520f seed sequence

<400> SEQUENCE: 104 agugcuu                                                                    7

<210> SEQ ID NO 105
<211> LENGTH: 7
<212> TYPE: RNA
<213> ORGANISM: artificial sequence
<220> FEATURE:
<223> OTHER INFORMATION: mature miR-520f seed sequence

<400> SEQUENCE: 105 aagugcu                                                                    7

<210> SEQ ID NO 106
<211> LENGTH: 7
<212> TYPE: RNA
<213> ORGANISM: artificial sequence
<220> FEATURE:
<223> OTHER INFORMATION: mature miR-524-5p seed sequence

<400> SEQUENCE: 106 uacaaag                                                                    7

<210> SEQ ID NO 107
<211> LENGTH: 7
<212> TYPE: RNA
<213> ORGANISM: artificial sequence
<220> FEATURE:
<223> OTHER INFORMATION: mature miR-524-3p seed sequence

<400> SEQUENCE: 107 aaggcgc                                                                    7

<210> SEQ ID NO 108
<211> LENGTH: 25
<212> TYPE: RNA
<213> ORGANISM: macaca mulatta

<400> SEQUENCE: 108
aaagugcuuc cuuuuagagg guuac                                               25

<210> SEQ ID NO 109
<211> LENGTH: 85
<212> TYPE: RNA
```

```
<213> ORGANISM: macaca mulatta

<400> SEQUENCE: 109
cucaggcugu gacccucuag agggaagcgc uuucuguggu cugaaagaaa agaaagugcu      60
uccuuuuaga ggguuaccgu uugag                                           85

<210> SEQ ID NO 110
<211> LENGTH: 23
<212> TYPE: RNA
<213> ORGANISM: macaca mulatta

<400> SEQUENCE: 110
aaagugcuuc cuuuuagagg guu                                             23

<210> SEQ ID NO 111
<211> LENGTH: 87
<212> TYPE: RNA
<213> ORGANISM: macaca mulatta

<400> SEQUENCE: 111
ucucaggcug ugacccucua gagggaagcg cuuucugugg ucugaaagaa aagaaagugc      60
uuccuuuuag aggguuaccg uuugaga                                         87

<210> SEQ ID NO 112
<211> LENGTH: 25
<212> TYPE: DNA
<213> ORGANISM: artificial sequence
<220> FEATURE:
<223> OTHER INFORMATION: HPRT forward primer

<400> SEQUENCE: 112
ctcaacttta actggaaaga atgtc                                           25

<210> SEQ ID NO 113
<211> LENGTH: 19
<212> TYPE: DNA
<213> ORGANISM: artificial sequence
<220> FEATURE:
<223> OTHER INFORMATION: HPRT reverse primer

<400> SEQUENCE: 113 tcctttcac cagcaagct                                                   19

<210> SEQ ID NO 114
<211> LENGTH: 20
<212> TYPE: DNA
<213> ORGANISM: artificial sequence
<220> FEATURE:
<223> OTHER INFORMATION: Vimentin forward primer

<400> SEQUENCE: 114
ggctcagatt caggaacagc                                                 20

<210> SEQ ID NO 115
<211> LENGTH: 20
<212> TYPE: DNA
<213> ORGANISM: artificial sequence
<220> FEATURE:
<223> OTHER INFORMATION: Vimentin reverse primer

<400> SEQUENCE: 115
gcttcaacgg caaagttctc                                                 20
```

-continued

```
<210> SEQ ID NO 116
<211> LENGTH: 20
<212> TYPE: DNA
<213> ORGANISM: artificial sequence
<220> FEATURE:
<223> OTHER INFORMATION: CDH11 forward primer

<400> SEQUENCE: 116
ggtctggaac cagttcttcg                                                  20

<210> SEQ ID NO 117
<211> LENGTH: 20
<212> TYPE: DNA
<213> ORGANISM: artificial sequence
<220> FEATURE:
<223> OTHER INFORMATION: CDH11 reverse primer

<400> SEQUENCE: 117
ggcatgaatg ttccctgatt                                                  20

<210> SEQ ID NO 118
<211> LENGTH: 21
<212> TYPE: RNA
<213> ORGANISM: human
<220> FEATURE:
<223> OTHER INFORMATION: isomiR of hsa-miR-520f

<400> SEQUENCE: 118
aagugcuucc uuuuagaggg u                                                21

<210> SEQ ID NO 119
<211> LENGTH: 22
<212> TYPE: RNA
<213> ORGANISM: human
<220> FEATURE:
<223> OTHER INFORMATION: isomiR of hsa-miR-520f

<400> SEQUENCE: 119
caagugcuuc cuuuuagagg gu                                               22

<210> SEQ ID NO 120
<211> LENGTH: 22
<212> TYPE: RNA
<213> ORGANISM: human
<220> FEATURE:
<223> OTHER INFORMATION: isomiR of hsa-miR-520f

<400> SEQUENCE: 120
aagugcuucc uuuuagaggg uu                                               22

<210> SEQ ID NO 121
<211> LENGTH: 22
<212> TYPE: RNA
<213> ORGANISM: human
<220> FEATURE:
<223> OTHER INFORMATION: isomiR of hsa-miR-518b

<400> SEQUENCE: 121
caaagcgcuc cccuuuagag gu                                               22

<210> SEQ ID NO 122
<211> LENGTH: 21
<212> TYPE: RNA
<213> ORGANISM: human
<220> FEATURE:
<223> OTHER INFORMATION: isomiR of hsa-miR-518b
```

<400> SEQUENCE: 122
caaagcgcuc cccuuuagag g                                             21

<210> SEQ ID NO 123
<211> LENGTH: 20
<212> TYPE: RNA
<213> ORGANISM: human
<220> FEATURE:
<223> OTHER INFORMATION: isomiR of hsa-miR-518b

<400> SEQUENCE: 123
caaagcgcuc cccuuuagag                                               20

<210> SEQ ID NO 124
<211> LENGTH: 22
<212> TYPE: RNA
<213> ORGANISM: human
<220> FEATURE:
<223> OTHER INFORMATION: isomiR of hsa-miR-524

<400> SEQUENCE: 124
gaaggcgcuu cccuuuggag ug                                            22

<210> SEQ ID NO 125
<211> LENGTH: 21
<212> TYPE: RNA
<213> ORGANISM: human
<220> FEATURE:
<223> OTHER INFORMATION: isomiR of hsa-miR-524

<400> SEQUENCE: 125
gaaggcgcuu cccuuuggag u                                             21

<210> SEQ ID NO 126
<211> LENGTH: 21
<212> TYPE: RNA
<213> ORGANISM: human
<220> FEATURE:
<223> OTHER INFORMATION: isomiR of hsa-miR-524

<400> SEQUENCE: 126
cuacaaaggg aagcacuuuc u                                             21

<210> SEQ ID NO 127
<211> LENGTH: 22
<212> TYPE: RNA
<213> ORGANISM: human
<220> FEATURE:
<223> OTHER INFORMATION: isomiR of hsa-miR-524

<400> SEQUENCE: 127
cuacaaaggg aagcacuuuc uc                                            22

<210> SEQ ID NO 128
<211> LENGTH: 20
<212> TYPE: RNA
<213> ORGANISM: human
<220> FEATURE:
<223> OTHER INFORMATION: isomiR of hsa-miR-524

<400> SEQUENCE: 128
cuacaaaggg aagcacuuuc                                               20

<210> SEQ ID NO 129
<211> LENGTH: 22

```
<212> TYPE: RNA
<213> ORGANISM: human
<220> FEATURE:
<223> OTHER INFORMATION: isomiR of miR-124

<400> SEQUENCE: 129
uaaggcacgc ggugaaugcc aa                                              22

<210> SEQ ID NO 130
<211> LENGTH: 21
<212> TYPE: RNA
<213> ORGANISM: human
<220> FEATURE:
<223> OTHER INFORMATION: isomiR of miR-124

<400> SEQUENCE: 130
uaaggcacgc ggugaaugcc a                                               21

<210> SEQ ID NO 131
<211> LENGTH: 19
<212> TYPE: RNA
<213> ORGANISM: human
<220> FEATURE:
<223> OTHER INFORMATION: isomiR of miR-124

<400> SEQUENCE: 131
uaaggcacgc ggugaaugc                                                  19

<210> SEQ ID NO 132
<211> LENGTH: 20
<212> TYPE: RNA
<213> ORGANISM: human
<220> FEATURE:
<223> OTHER INFORMATION: isomiR of miR-124

<400> SEQUENCE: 132
uaaggcacgc ggugaaugcc                                                 20

<210> SEQ ID NO 133
<211> LENGTH: 22
<212> TYPE: RNA
<213> ORGANISM: human
<220> FEATURE:
<223> OTHER INFORMATION: isomiR of hsa-miR-206

<400> SEQUENCE: 133
uggaauguaa ggaagugugu gg                                              22

<210> SEQ ID NO 134
<211> LENGTH: 23
<212> TYPE: RNA
<213> ORGANISM: human
<220> FEATURE:
<223> OTHER INFORMATION: isomiR of hsa-miR-206

<400> SEQUENCE: 134
uggaauguaa ggaagugugu ggu                                             23

<210> SEQ ID NO 135
<211> LENGTH: 21
<212> TYPE: RNA
<213> ORGANISM: human
<220> FEATURE:
<223> OTHER INFORMATION: isomiR of hsa-miR-206

<400> SEQUENCE: 135
```

```
uggaauguaa ggaagugugu g                                              21
```

<210> SEQ ID NO 136
<211> LENGTH: 25
<212> TYPE: RNA
<213> ORGANISM: human
<220> FEATURE:
<223> OTHER INFORMATION: isomiR of hsa-miR-181a-1

<400> SEQUENCE: 136

```
aacauucaac gcugucgguq aguuu                                          25
```

<210> SEQ ID NO 137
<211> LENGTH: 23
<212> TYPE: RNA
<213> ORGANISM: human
<220> FEATURE:
<223> OTHER INFORMATION: isomiR of hsa-miR-181a-1

<400> SEQUENCE: 137

```
aacauucaac gcugucgguq agu                                            23
```

<210> SEQ ID NO 138
<211> LENGTH: 22
<212> TYPE: RNA
<213> ORGANISM: human
<220> FEATURE:
<223> OTHER INFORMATION: isomiR of hsa-miR-181a-1

<400> SEQUENCE: 138

```
aacauucaac gcugucgguq ag                                             22
```

<210> SEQ ID NO 139
<211> LENGTH: 24
<212> TYPE: RNA
<213> ORGANISM: human
<220> FEATURE:
<223> OTHER INFORMATION: isomiR of hsa-miR-181a-1

<400> SEQUENCE: 139

```
aacauucaac gcugucgguq aguu                                           24
```

<210> SEQ ID NO 140
<211> LENGTH: 18
<212> TYPE: RNA
<213> ORGANISM: human
<220> FEATURE:
<223> OTHER INFORMATION: isomiR of hsa-miR-181a-1

<400> SEQUENCE: 140

```
aacauucaac gcugucgg                                                  18
```

<210> SEQ ID NO 141
<211> LENGTH: 19
<212> TYPE: RNA
<213> ORGANISM: human
<220> FEATURE:
<223> OTHER INFORMATION: isomiR of hsa-miR-181a-1

<400> SEQUENCE: 141

```
aacauucaac gcugucggu                                                 19
```

<210> SEQ ID NO 142
<211> LENGTH: 20
<212> TYPE: RNA
<213> ORGANISM: human

```
<220> FEATURE:
<223> OTHER INFORMATION: isomiR of hsa-miR-181a-1

<400> SEQUENCE: 142
aacauucaac gcugucggug                                                    20

<210> SEQ ID NO 143
<211> LENGTH: 21
<212> TYPE: RNA
<213> ORGANISM: human
<220> FEATURE:
<223> OTHER INFORMATION: isomiR of hsa-miR-181a-1

<400> SEQUENCE: 143
aacauucaac gcugucggug a                                                  21

<210> SEQ ID NO 144
<211> LENGTH: 22
<212> TYPE: RNA
<213> ORGANISM: human
<220> FEATURE:
<223> OTHER INFORMATION: isomiR of hsa-miR-141

<400> SEQUENCE: 144
uaacacuguc ugguaaagau gg                                                 22

<210> SEQ ID NO 145
<211> LENGTH: 21
<212> TYPE: RNA
<213> ORGANISM: human
<220> FEATURE:
<223> OTHER INFORMATION: isomiR of hsa-miR-141

<400> SEQUENCE: 145
uaacacuguc ugguaaagau g                                                  21

<210> SEQ ID NO 146
<211> LENGTH: 23
<212> TYPE: RNA
<213> ORGANISM: human
<220> FEATURE:
<223> OTHER INFORMATION: isomiR of hsa-miR-141

<400> SEQUENCE: 146
uaacacuguc ugguaaagau ggc                                                23

<210> SEQ ID NO 147
<211> LENGTH: 20
<212> TYPE: RNA
<213> ORGANISM: human
<220> FEATURE:
<223> OTHER INFORMATION: isomiR of hsa-miR-141

<400> SEQUENCE: 147
uaacacuguc ugguaaagau                                                    20

<210> SEQ ID NO 148
<211> LENGTH: 19
<212> TYPE: RNA
<213> ORGANISM: human
<220> FEATURE:
<223> OTHER INFORMATION: isomiR of hsa-miR-141

<400> SEQUENCE: 148
uaacacuguc ugguaaaga                                                     19
```

```
<210> SEQ ID NO 149
<211> LENGTH: 24
<212> TYPE: RNA
<213> ORGANISM: human
<220> FEATURE:
<223> OTHER INFORMATION: isomiR of hsa-miR-141

<400> SEQUENCE: 149
uaacacuguc ugguaaagau ggcu                                              24

<210> SEQ ID NO 150
<211> LENGTH: 23
<212> TYPE: RNA
<213> ORGANISM: human
<220> FEATURE:
<223> OTHER INFORMATION: isomiR of hsa-miR-141

<400> SEQUENCE: 150
uaacacuguc ugguaacgau guu                                               23

<210> SEQ ID NO 151
<211> LENGTH: 22
<212> TYPE: RNA
<213> ORGANISM: human
<220> FEATURE:
<223> OTHER INFORMATION: isomiR of hsa-miR-200a

<400> SEQUENCE: 151
uaacacuguc ugguaacgau gu                                                22

<210> SEQ ID NO 152
<211> LENGTH: 23
<212> TYPE: RNA
<213> ORGANISM: human
<220> FEATURE:
<223> OTHER INFORMATION: isomiR of hsa-miR-200b

<400> SEQUENCE: 152
uaauacugcc ugguaaugau gac                                               23

<210> SEQ ID NO 153
<211> LENGTH: 22
<212> TYPE: RNA
<213> ORGANISM: human
<220> FEATURE:
<223> OTHER INFORMATION: isomiR of hsa-miR-200b

<400> SEQUENCE: 153
uaauacugcc ugguaaugau ga                                                22

<210> SEQ ID NO 154
<211> LENGTH: 22
<212> TYPE: RNA
<213> ORGANISM: human
<220> FEATURE:
<223> OTHER INFORMATION: isomiR of hsa-miR-200b

<400> SEQUENCE: 154
caucuuacug ggcagcauug ga                                                22

<210> SEQ ID NO 155
<211> LENGTH: 21
<212> TYPE: RNA
<213> ORGANISM: human
<220> FEATURE:
<223> OTHER INFORMATION: isomiR of hsa-miR-200b
```

-continued

```
<400> SEQUENCE: 155
caucuuacug ggcagcauug g                                          21

<210> SEQ ID NO 156
<211> LENGTH: 23
<212> TYPE: RNA
<213> ORGANISM: human
<220> FEATURE:
<223> OTHER INFORMATION: isomiR of hsa-miR-200c

<400> SEQUENCE: 156
uaauacugcc ggguaaugau gga                                        23

<210> SEQ ID NO 157
<211> LENGTH: 22
<212> TYPE: RNA
<213> ORGANISM: human
<220> FEATURE:
<223> OTHER INFORMATION: isomiR of hsa-miR-200c

<400> SEQUENCE: 157
uaauacugcc ggguaaugau gg                                         22

<210> SEQ ID NO 158
<211> LENGTH: 21
<212> TYPE: RNA
<213> ORGANISM: human
<220> FEATURE:
<223> OTHER INFORMATION: isomiR of hsa-miR-205

<400> SEQUENCE: 158
uccuucauuc caccggaguc u                                          21

<210> SEQ ID NO 159
<211> LENGTH: 22
<212> TYPE: RNA
<213> ORGANISM: human
<220> FEATURE:
<223> OTHER INFORMATION: isomiR of hsa-miR-205

<400> SEQUENCE: 159
uccuucauuc caccggaguc ug                                         22

<210> SEQ ID NO 160
<211> LENGTH: 23
<212> TYPE: RNA
<213> ORGANISM: human
<220> FEATURE:
<223> OTHER INFORMATION: isomiR of hsa-miR-205

<400> SEQUENCE: 160
uccuucauuc caccggaguc ugu                                        23

<210> SEQ ID NO 161
<211> LENGTH: 22
<212> TYPE: RNA
<213> ORGANISM: human
<220> FEATURE:
<223> OTHER INFORMATION: isomiR of hsa-miR-429

<400> SEQUENCE: 161
uaauacuguc ugguaaaacc gu                                         22

<210> SEQ ID NO 162
```

```
<211> LENGTH: 21
<212> TYPE: RNA
<213> ORGANISM: human
<220> FEATURE:
<223> OTHER INFORMATION: isomiR of hsa-miR-429

<400> SEQUENCE: 162
uaauacuguc ugguaaaacc g                                              21

<210> SEQ ID NO 163
<211> LENGTH: 24
<212> TYPE: RNA
<213> ORGANISM: artificial sequence
<220> FEATURE:
<223> OTHER INFORMATION: mimic based on C. Elegans Cel-miR-67

<400> SEQUENCE: 163
ucacaaccuc cuagaaagag uaga                                           24
```

US 9,161,947 B2

MIRNA MOLECULE DEFINED BY ITS SOURCE AND ITS DIAGNOSTIC AND THERAPEUTIC USES IN DISEASES OR CONDITIONS ASSOCIATED WITH EMT

This application is a continuation of PCT/NL2011/050152, filed Mar. 4, 2011, which claims the benefit of U.S. provisional application 61/310,452 filed Mar. 4, 2010 and European patent application EP10155512.6 filed Mar. 4, 2010. The contents of each of these applications are incorporated by reference herein in their entirety.

FIELD OF THE INVENTION

The invention relates to the diagnostic and therapeutic uses of a miRNA molecule defined by its source later on in diseases and conditions associated with EMT (Epithelial to Mesenchymal Transition).

BACKGROUND OF THE INVENTION

Most solid tumors are epithelial in origin (i.e. carcinomas). A loss of epithelial cell markers (e.g. E-cadherin) and gain of mesenchymal cell markers (e.g. N-cadherin and Vimentin) has been observed in patient tumor samples, including prostate cancer (1). Cancer cells can dedifferentiate through this so-called Epithelial to Mesenchymal Transition (EMT). During EMT, intercellular cell junctions are broken down, thereby giving tumor cells the ability to migrate and invade into the surrounding tissue or through blood vessel walls. Such phenotypic changes are thought to play a major role in dissemination of the disease and ultimately lead to disease progression, which is often associated with poor prognosis for the patients (2;3).

Loss of E-cadherin expression is considered as a molecular hallmark of EMT. EMT in tumor cells results from a transcriptional reprogramming of the cell. In particular the transcriptional repression of the E-cadherin (CDH1) gene promoter has been shown to trigger the EMT phenotype. The E-cadherin protein is one of the most important cadherin molecules mediating cell-cell contacts in epithelial cells/tissues. CDH1 is repressed by binding of the transcriptional repressors, SNAI1, SNAI2, TCF3, TWIST, ZEB1, ZEB2 or KLF8 (4-7), to three so-called E-boxes in the CDH1 proximal promoter region (8-10). Inhibiting the binding of these repressors to the CDH1 promoter can revert EMT, also called mesenchymal to epithelial transition (MET), and inhibits tumor cell invasion and tumor progression (11).

Recently, the expression of several microRNAs has been shown to be linked with EMT (12). By comparing microRNA expression profiles of cells with an epithelial and (induced) mesenchymal phenotype, members of the miR-200 family (miR-141, miR-200a/b/c, and miR-429) and miR-205 were identified as EMT-associated miRs (13-15). The target genes of the EMT-associated microRNAs of the miR-200 family were shown to be ZEB1 and ZEB2. MicroRNAs targeting the other known transcriptional repressors of CDH1 (i.e. SNAI1, SNAI2, TCF3 and TWIST1) have not yet been found. The identification of these microRNAs in an expression profile of cells which have undergone EMT does not necessarily mean that these microRNAs are involved during EMT.

There is currently no effective known medicament that may be used for specifically preventing, treating, reverting and/or delaying a disease or condition associated with EMT in a subject. The only standard treatments comprise chemotherapy, radiotherapy, surgery. Particularly, the identification of patients that will or have already developed metastases and/or early treatment of patients with tumors expressing EMT markers, such as expression of mesenchymal Cadherin and/or lower expression of E-Cadherin could contribute to better disease free and overall survival. Therefore, there is still a need for diagnostic markers for EMT and for new treatments of disease or conditions associated with EMT.

DESCRIPTION OF THE INVENTION

In a first aspect, there is provided a miRNA molecule or an equivalent thereof wherein a source of said miRNA molecule or equivalent thereof comprises at least 80 nucleotides and comprises a motif having at least 98% identity with the motif represented by SEQ ID NO:1 or a composition comprising said miRNA molecule or equivalent thereof or said source thereof for use as a medicament for preventing, treating, reverting, curing and/or delaying a disease or a condition associated with EMT.

MicroRNAs (miRNAs) are small RNAs of 17-25 nucleotides, which function as regulators of gene expression in eukaryotes. miRNAs are initially expressed in the nucleus as part of long primary transcripts called primary miRNAs (pri-miRNAs). Inside the nucleus, pri-miRNAs are partially digested by the enzyme Drosha, to form 65-120 nucleotide-long hairpin precursor miRNAs (pre-miRNAs) that are exported to the cytoplasm for further processing by Dicer into shorter, mature miRNAs, which are the active molecules. In animals, these short RNAs comprise a 5' proximal "seed" region (nucleotides 2 to 8) which appears to be the primary determinant of the pairing specificity of the miRNA to the 3' untranslated region (3'-UTR) of a target mRNA. A more detailed explanation is given in the part dedicated to general definitions.

Each of the definitions given below concerning a miRNA molecule, a miRNA equivalent or a miRNA source is to be used for each of the identified miRNAs or miRNA equivalent or miRNA sources of this application: miRNA-124-1, miRNA-206, miRNA181a-1, miRNA-141, miRNA-200a, miRNA-200b, miRNA-200c, miRNA-429, miRNA-205, miRNA518b, miRNA520f, miRNA524 and sources thereof, further including a source comprising at least 80 nucleotides and comprising a motif having at least 98% identity with the motif represented by SEQ ID NO:1. Preferred mature (as identified in Table 3), seed (as identified in Table 5) isomiRs (as identified in Table 6) or source sequences (as identified in Tables 2 (RNA precursor) or 4 (DNA encoding a RNA precursor)) of said miRNA molecule or equivalent thereof respectively are identified in corresponding tables.

Within the whole text of the application unless otherwise indicated, a miRNA may also be named a miRNA molecule, a miR, or an equivalent thereof or a source or a precursor thereof. A preferred equivalent is a mature, an isomiR, or a mimic. Each sequence identified herein may be identified as being SEQ ID NO as used in the text of the application or as corresponding SEQ ID NO in the sequence listing.

In the context of the invention a miRNA molecule or an equivalent or a mimic or an isomiR thereof may be a synthetic or natural or recombinant or mature or part of a mature miRNA or a human miRNA or derived from a human miRNA as further defined in the part dedicated to the general definitions. A human miRNA molecule is a miRNA molecule which is found in a human cell, tissue, organ or body fluids (i.e. endogenous human miRNA molecule). A human miRNA molecule may also be a human miRNA molecule derived from an endogenous human miRNA molecule by substitution, deletion and/or addition of a nucleotide. A miRNA molecule or an equivalent or a mimic thereof may be a single stranded or double stranded RNA molecule.

Within the context of the invention, a preferred miRNA molecule or an equivalent or a mimic or an isomiR thereof is such that a source of said miRNA molecule or equivalent or mimic or isomiR thereof comprises or consists of at least 80 nucleotides and comprises a motif having at least 98% identity with the motif represented by SEQ ID NO:1 is further preferably defined as follows.

SEQ ID NO: 1 is as follows:

UCAnGCUGUGnCCCUnnAnAGGGAAGCnCUUUCUnUnGUCnnAAnGAAA

AnnAnGnGCUnCCnUUUnGAGnnUUACnGUUUG

In the motif represented by SEQ ID NO:1, n may be any base A, U, C or G.

In a further preferred embodiment, there is provided a miRNA molecule or an equivalent or a mimic or a isomiR thereof such that a source of said miRNA molecule or equivalent or mimic or isomiR thereof comprises at least 80 nucleotides and comprises a motif having at least 98% identity with the motif represented by SEQ ID NO:1. More preferably, the identity is at least 99% or 100%. In a preferred embodiment, said source is a precursor of a miRNA-518b, a miRNA-520f or a miRNA-524 molecule or an equivalent or a mimic or a isomiR thereof. Preferred sources and precursors are later defined herein.

The invention therefore relates to a miRNA molecule or an equivalent or a mimic or an isomiR thereof or a source thereof or a composition comprising said miRNA molecule or equivalent or mimic or isomiR thereof or source thereof, as defined in coming paragraphs, wherein the miRNA molecule is a miRNA-518b, miRNA-520f and/or mi-RNA-524 or an equivalent or a mimic or an isomiR thereof or a source thereof. Preferred miRNA molecule, equivalent, mimic and isomiR are later defined herein.

In a preferred embodiment, an equivalent of a miRNA-518b, a miRNA-520f or of a miRNA-524 is a human miRNA molecule. A human miRNA molecule is a miRNA molecule which is found in a human cell, tissue or organ. A human miRNA molecule may also be a human miRNA molecule derived from an endogenous human miRNA molecule by substitution, deletion and/or addition of a nucleotide. In this context, a "nucleotide" may mean 1, 2, 3, 4, 5 or more nucleotides. A preferred equivalent of a miRNA-518b, a miRNA-520f or of a miRNA-524 molecule is not an mml-mir-519a or an mml-mir-520c miRNA molecule as identified hereafter. A preferred source or precursor of a miRNA-518b, a miRNA-520f or of a miRNA-524 molecule is not a source or a precursor of an mml-mir-519a or an mml-mir-520c miRNA molecule as identified hereafter. Preferred disclaimed mature and precursor sequences of mml-mir-519a are identified as SEQ ID NO: 108 and 109. Preferred mature and precursor sequences of mml-mir-520c are identified as SEQ ID NO: 110 and 111.

In a preferred embodiment, a miRNA molecule or equivalent or mimic or isomiR thereof comprises at least 6 of the 7 nucleotides present in the seed sequence of said miRNA molecule or equivalent or mimic or isomiR thereof (Table 5 shows preferred seed sequence of each of the miRNAs molecule identified herein). Preferably in this embodiment, a miRNA molecule or an equivalent or a mimic or isomiR thereof can be from 6, 7, 8, 9, 10, 11, 12 to 30 nucleotides in length and more preferably comprises at least 6 of the 7 nucleotides present in the seed sequence of said miRNA molecule or equivalent thereof. Even more preferably a miRNA molecule or an equivalent or a mimic or isomiR thereof is from 15 to 28 nucleotides in length and more preferably comprises at least 6 of the 7 nucleotides present in the seed sequence. Even more preferably a miRNA molecule has a length of at least 6, 7, 8, 9, 10, 11, 12, 13, 14, 15, 16, 17, 18, 19, 20, 21, 22, 23, 24, 25, 26, 27, 28, 29, 30 nucleotides or more and preferably comprises at least 6 of the 7 nucleotides present in the seed sequence.

In each of these embodiments, a mirRNA molecule or an equivalent or a mimic or isomiR thereof may comprise the 7 nucleotides of the seed sequence as identified in table 5. Even more preferably a miRNA molecule has a length of at least 7, 8, 9, 10, 11, 12, 13, 14, 15, 16, 17, 18, 19, 20, 21, 22, 23, 24, 25, 26, 27, 28, 29, 30 nucleotides or more and comprises the 7 nucleotides present in the seed sequence as identified in table 5.

Accordingly, a preferred miRNA-520f molecule or equivalent or mimic or isomiR thereof comprises at least 6 of the 7 nucleotides present in the seed sequence identified as SEQ ID NO: 104 or 105 and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly, a preferred miRNA-518b molecule or equivalent or mimic or isomiR thereof comprises at least 6 of the 7 nucleotides present in the seed sequence identified as SEQ ID NO: 103 and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly, a preferred miRNA-524 molecule or equivalent or mimic or isomiR thereof comprises at least 6 of the 7 nucleotides present in the seed sequence identified as SEQ ID NO: 106 or 107 and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

In another preferred embodiment, a miRNA molecule or an equivalent or mimic or isomiR thereof comprises at least 6 of the 7 nucleotides present in a given seed sequence as identified in table 5 as SEQ ID NO: 87-107 and has at least 80% identity over the whole mature sequence (Table 3 shows preferred mature sequences of each of the miRNAs identified herein). Preferably, identity is at least 80%, 81%, 82%, 83%, 84%, 85%, 86%, 87%, 88%, 89%, 90%, 91%, 92%, 93%, 94%, 95%, or higher such as 96%, 97%, 98%, 99% or 100%.

Alternatively, preferably in this embodiment, a miRNA molecule or an equivalent or a mimic or an isomiR thereof has a length of not more than 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides, comprises at least 6 of the 7 nucleotides present in a given seed sequence as identified in table 5 as SEQ ID NO: 87-107 and has at least 80% identity over the whole mature sequence as identified in table 3 as SEQ ID NO: 2-21. Preferably, identity is at least 80%, 81%, 82%, 83%, 84%, 85%, 86%, 87%, 88%, 89%, 90%, 91%, 92%, 93%, 94%, 95%, 96%, 97%, 98%, 99% or 100%.

In another preferred embodiment, an isomiR of a miRNA molecule has at least 80% identity over the whole isomiR sequence (Table 6 shows preferred isomiR of each of the mature miRNAs identified as SEQ ID NO: 118-162). Preferably, identity is at least 80%, 81%, 82%, 83%, 84%, 85%, 86%, 87%, 88%, 89%, 90%, 91%, 92%, 93%, 94%, 95% or higher such as 96%, 97%, 98%, 99% or 100%. Preferably in this embodiment, an isomiR of a miRNA molecule or an equivalent or a mimic thereof has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Identity may be assessed using several ways as defined later herein. However, in a preferred embodiment, identity means identity percentage and is calculated by the number of equal nucleotides between subject and query, divided by the total length of the query, and multiplied by 100.

Accordingly, a preferred miRNA-520f molecule or equivalent or mimic or isomiR thereof comprises at least 6 of the 7 nucleotides present in the seed sequence identified as SEQ ID NO: 104 or 105 and/or has at least 80%, 81%, 82%, 83%, 84%, 85%, 86%, 87%, 88%, 89%, 90%, 91%, 92%, 93%, 94%, 95%, 96%, 97%, 98%, 99% or 100% identity over SEQ ID NO: 19, 118, 119 and/or 120 and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

Accordingly, a preferred miRNA-518b molecule or equivalent or mimic or isomiR thereof comprises at least 6 of the 7 nucleotides present in the seed sequence identified as SEQ ID NO: 103 and/or has at least 80%, 81%, 82%, 83%, 84%, 85%, 86%, 87%, 88%, 89%, 90%, 91%, 92%, 93%, 94%, 95%, 96%, 97%, 98%, 99% or 100% identity over SEQ ID NO: 18, 121, 122 and/or 123 and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

Accordingly, a preferred miRNA-524 molecule or equivalent or mimic or isomiR thereof comprises at least 6 of the 7 nucleotides present in the seed sequence identified as SEQ ID NO: 106 or 107 and/or has at least 80%, 81%, 82%, 83%, 84%, 85%, 86%, 87%, 88%, 89%, 90%, 91%, 92%, 93%, 94%, 95%, 96%, 97%, 98%, 99% or 100% identity over SEQ ID NO: 20, 21, 124, 125, 126, 127 and/or 128 and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

Another preferred miRNA molecule or equivalent or mimic or an isomiR thereof has at least 80% identity with a seed sequence (as identified in Table 5 as SEQ ID NO: 87-107) or with a mature sequence (as identified in Table 3 as SEQ ID NO: 2-21) or with a precursor sequence (as identified in Table 2 as SEQ ID NO: 22-35) or with a DNA encoding an RNA precursor (as identified in Table 4 as SEQ ID NO: 36-47) or with an isomiR sequence (as identified in Table 6 as SEQ ID NO: 118-162). Identity may be at least 65%, 70%, 75%, 80%, 85%, 90%, 95%, 99% or 100%. Identity is preferably assessed on the whole SEQ ID NO as identified in a given Table. However, identity may also be assessed on part of a given SEQ ID NO. Part may mean at least 50% of the length of the SEQ ID NO, at least 60%, at least 70%, at least 80%, at least 90% or 100%.

An equivalent may be an isomiR or a mimic. A precursor sequence may result in more than one isomiR sequences depending on the maturation process (see for example miRNA-520f or miRNA-518b or miRNA-524 where in certain tissues, multiple isomiRs have been identified (Table 6: SEQ ID NO:118-128). A mimic is a molecule which has a similar or identical activity with a miRNA molecule. In this context a similar activity is given the same meaning as an acceptable level of an activity.

Each of the miRNA molecules or equivalents or mimics or isomiRs thereof as identified herein has an acceptable level of an activity of a given miRNA they derive from. An acceptable level of an activity is preferably that said miRNA or equivalent or mimics or isomiRs thereof is still able to exhibit an acceptable level of said activity of said miRNA. An activity of a given miRNA or an equivalent thereof is for example the ability to induce a detectable MET as later defined herein. An acceptable level of an activity is preferably at least 30%, 40%, 50%, 60%, 70%, 80%, 90%, 95% or 100% of the activity of the miRNA they derive from. Such activity may be as measured in a bladder cell of an individual or in vitro in a cell by comparison to the activity of the miRNA they derive from. The assessment of the activity may be carried out at the mRNA level, preferably using RT-qPCR. The assessment of the activity may be carried out at the protein level, preferably using Western blot analysis or, immunohistochemistry or immunofluorescence analysis of cross-sections.

The assessment of the activity may be carried out using cells expressing a CDH1 promotor driven firefly luciferase construct and measuring luciferase activity.

A preferred activity of any of the miRNA molecule or equivalent thereof as identified herein (i.e. miRNA-124-1, miRNA-206, miRNA181a-1, miRNA-141, miRNA-200a, miRNA-200b, miRNA-200c, miRNA-429, miRNA-205, miRNA-518b, miRNA-520f, miRNA-524) or a preferred activity of a miRNA molecule or equivalent thereof identified by a preferred source (i.e. a miRNA molecule or an equivalent thereof wherein a source of said miRNA molecule or equivalent thereof comprises at least 80 nucleotides and comprises a motif having at least 98% identity with the motif represented by SEQ ID NO:1) is to induce a detectable MET in a subject as later defined herein.

A source of a miRNA molecule or a source of an equivalent of a miRNA molecule, mimic, isomiR may be any molecule which is able to induce the production of a miRNA molecule or of an equivalent thereof such as a mimic or isomiR as identified herein and which comprises a hairpin-like structure and/or a double stranded nucleic acid molecule. The presence of a hairpin-like structure, may be assessed using the RNAshapes program (Steffen P., et al, (2006), Bioinformatics, 22: 500-503) using sliding windows of 80, 100 and 120 nt or more. The presence of a hairpin-like structure is usually present in a natural or endogenous source of a miRNA molecule whereas a double-stranded nucleic acid molecule is usually present in a recombinant or synthetic source of a miRNA molecule or of an equivalent thereof.

A source of a miRNA molecule or of an equivalent or a mimic or an isomiR thereof may be a single stranded, a double stranded RNA or a partially double stranded RNA or comprise three strands, an example of which is described in WO2008/10558. As used herein partially double stranded refers to double stranded structures that also comprise single stranded structures at the 5' and/or at the 3' end, it may occur when each strand of a miRNA molecule does not have the same length. In general, such partial double stranded miRNA molecule may have less than 75% double stranded structure and more than 25% single stranded structure, or less than 50% double stranded structure and more than 50% single stranded structure, or more preferably less than 25%, 20% or 15% double stranded structure and more than 75%, 80%, 85% single stranded structure. Alternatively, a source of a miRNA molecule or of an equivalent or a mimic or an isomiR thereof is a DNA molecule encoding a precursor of a miRNA molecule or of an equivalent or a mimic or an isomiR thereof. Preferred DNA molecules in this context are identified in table 4 as SEQ ID NO: 36-47. The invention encompasses the use of a DNA molecule encoding a precursor of a miRNA molecule that has at least 80% identity with said sequence as identified in table 4. Preferably, the identity is at least 80%, 81%, 82%, 83%, 84%, 85%, 86%, 87%, 88%, 89% 90%, 91%, 92%, 93%, 94%, 95%, 96%, 97%, 98%, 99% or 100%. Preferably in this embodiment, a DNA molecule has a length of at least 50, 55, 60, 70, 75, 80, 85, 90, 95, 100, 130, 150, 200, 250, 300, 350, 400 nucleotides or more and has at least 80%, 81%, 82%, 83%, 84%, 85%, 86%, 87%, 88%, 89% 90%, 91%, 92%, 93%, 94%, 95%, 96%, 97%, 98%, 99% or 100% identity with a DNA sequence as identified in table 4 as SEQ ID NO: 36-47.

Accordingly, a preferred source of a miRNA-520f molecule has at least 80%, 81%, 82%, 83%, 84%, 85%, 86%, 87%, 88%, 89%, 90%, 91%, 92%, 93%, 94%, 95%, 96%, 97%, 98%, 99% or 100% identity with SEQ ID NO: 45 and/or has a length of at least 50, 55, 60, 70, 75, 80, 85, 90, 95, 100, 130, 150, 200, 250, 300, 350, 400 nucleotides or more.

Accordingly, a preferred source of a miRNA-518b molecule has at least 80%, 81%, 82%, 83%, 84%, 85%, 86%, 87%, 88%, 89%, 90%, 91%, 92%, 93%, 94%, 95%, 96%, 97%, 98%, 99% or 100% identity with SEQ ID NO: 44 and/or has a length of at least 50, 55, 60, 70, 75, 80, 85, 90, 95, 100, 130, 150, 200, 250, 300, 350, 400 nucleotides or more.

Accordingly, a preferred source of a miRNA-524 molecule has at least 80%, 81%, 82%, 83%, 84%, 85%, 86%, 87%, 88%, 89%, 90%, 91%, 92%, 93%, 94%, 95%, 96%, 97%, 98%, 99% or 100% identity with SEQ ID NO: 46 and/or has a length of at least 50, 55, 60, 70, 75, 80, 85, 90, 95, 100, 130, 150, 200, 250, 300, 350, 400 nucleotides or more.

The induction of the production of a given miRNA molecule or of an equivalent thereof or of a mimic or an isomiR thereof is preferably obtained when said source is introduced into a cell using one assay as defined below. Cells encompassed by the present invention are later on defined.

A preferred source of a miRNA molecule or of an equivalent thereof or of a mimic or an isomiR thereof is a precursor thereof, more preferably a nucleic acid encoding said miRNA molecule or an equivalent thereof or of a mimic or an isomiR thereof. A preferred precursor is a naturally-occurring precursor. A precursor may be a synthetic or recombinant precursor.

A preferred precursor of a given miRNA molecule is identified in table 2 as SEQ ID NO: 22-35. The invention encompasses the use of a precursor of a miRNA molecule or of an equivalent thereof that has at least 80% identity with said sequence. Preferably, identity is at least 80%, 81%, 82%, 83%, 84%, 85%, 86%, 87%, 88%, 89%, 90%, 91%, 92%, 93%, 94%, 95%, 96%, 97%, 98%, 99% or 100%. Preferably in this embodiment, an RNA molecule has a length of at least 50, 55, 60, 70, 75, 80, 85, 90, 95, 100, 130, 150, 200, 250, 300, 350, 400 nucleotides or more and has at least 80%, 81%, 82%, 83%, 84%, 85%, 86%, 87%, 88%, 89%, 90%, 91%, 92%, 93%, 94%, 95%, 96%, 97%, 98%, 99% or 100% identity with a sequence as identified in table 2 as SEQ ID NO: 22-35.

Accordingly, a preferred source of a miRNA-520f molecule has at least 80%, 81%, 82%, 83%, 84%, 85%, 86%, 87%, 88%, 89%, 90%, 91%, 92%, 93%, 94%, 95%, 96%, 97%, 98%, 99% or 100% identity with SEQ ID NO: 33 and/or has a length of at least 50, 55, 60, 70, 75, 80, 85, 90, 95, 100, 130, 150, 200, 250, 300, 350, 400 nucleotides or more.

Accordingly, a preferred source of a miRNA-518b molecule has at least 80%, 81%, 82%, 83%, 84%, 85%, 86%, 87%, 88%, 89%, 90%, 91%, 92%, 93%, 94%, 95%, 96%, 97%, 98%, 99% or 100% identity with SEQ ID NO: 32 and/or has a length of at least 50, 55, 60, 70, 75, 80, 85, 90, 95, 100, 130, 150, 200, 250, 300, 350, 400 nucleotides or more.

Accordingly, a preferred source of a miRNA-524 molecule has at least 80%, 81%, 82%, 83%, 84%, 85%, 86%, 87%, 88%, 89%, 90%, 91%, 92%, 93%, 94%, 95%, 96%, 97%, 98%, 99% or 100% identity with SEQ ID NO: 34 and/or has a length of at least 50, 55, 60, 70, 75, 80, 85, 90, 95, 100, 130, 150, 200, 250, 300, 350, 400 nucleotides or more.

Preferred sources or precursors have been defined later herein. A preferred source includes or comprises an expression construct comprising a nucleic acid, i.e. DNA encoding said precursor of said miRNA, more preferably said expression construct is a viral gene therapy vector selected from gene therapy vectors based on an adenovirus, an adeno-associated virus (AAV), a herpes virus, a pox virus and a retrovirus. A preferred viral gene therapy vector is an AAV or Lentiviral vector. Other preferred vectors are oncolytic viral vectors. Such vectors are further described herein below. Alternatively, a source may be a synthetic miRNA molecule or a chemical mimic as further defined in the part dedicated to general definitions.

The detection of the presence of a miRNA molecule or of an equivalent thereof such as a mimic or an isomiR may be carried out using any technique known to the skilled person. The assessment of the expression level or of the presence of a miRNA molecule or of an equivalent thereof is preferably performed using classical molecular biology techniques such as (real time) qPCR, microarrays, bead arrays, RNAse protection analysis or Northern analysis or cloning and sequencing. The skilled person will understand that alternatively or in combination with the quantification of a miRNA molecule or of an equivalent thereof, the quantification of a substrate of a corresponding miRNA molecule or of an equivalent thereof or any compound known to be associated with a function of said miRNA molecule or of said equivalent thereof or the quantification of a function or activity of said miRNA molecule or of said equivalent thereof using a specific assay is encompassed within the scope of the invention.

Preferred compositions and formulations are all defined later herein. A miRNA molecule or an equivalent thereof or a mimic or an isomiR thereof may be used as such as a naked molecule, with or without chemical modifications, or encapsulated into a particle or conjugated to a moiety. A preferred composition comprises a miRNA molecule or an equivalent thereof or a mimic or an isomiR thereof encapsulated into a nanoparticle or a liposomal structure. A miRNA molecule or equivalent thereof or a mimic or an isomiR thereof may be an aptamer-miRNA hybrid. A miRNA molecule or equivalent thereof may be an aptamer-miRNA hybrid. An aptamer-miRNA is defined as a miRNA linked to an RNA (or DNA) oligonucleotide, the latter adopting a conformation that targets the aptamer-miRNA hybrid molecule to a cell-surface protein (e.g. the Prostate-Specific Membrane Antigen (PSMA)). The aptamer-tagged miRNA can be linked to e.g. polyethylene glycol, which increases the chimera's circulating half-life (Dassie, J. P., et al. *Nat. Biotechnol.* 27: 839-849 (2009)).

Any disease or condition wherein EMT is involved or associated may be prevented, delayed, cured and/or treated with a molecule as defined herein.

Within the context of the invention, Epithelial Mesenchymal Transition (EMT) is an orchestrated series of events in which cell-cell and cell-extracellular matrix (ECM) interactions are altered to allow the release of epithelial cells from the surrounding tissue. The epithelial cell cytoskeleton is reorganised to confer the ability of the cell to move through a three-dimensional ECM via molecular reprogramming of the cell.

Molecular reprogramming of an epithelial cell is necessary to achieve a mesenchymal phenotype and involves the down-regulation or decrease of the expression of epithelial proteins, such as E-cadherin and junction proteins such as desmoplakin, claudin and occludin. In addition, the expression of mesenchymal proteins is upregulated or increased, including for example, the expression of ECM proteins such as MMPs and fibronectin and cell surface proteins such as N-cadherin and integrin $\alpha v\beta 6$. Transcription factors may also be upregulated or increased in cells exhibiting a mesenchymal phenotype such as for example, SNAI1 (also known as SNAIL), TWIST, ZEB1 (also known as δEF1) and ZEB2 (also known as SIP1). Reference to inducing the "transition" of an epithelial cell to a cell exhibiting a mesenchymal phenotype should be understood as a reference to inducing the genetic, morphologic and/or functional changes which are required to change an epithelial cell to a cell exhibiting a mesenchymal phenotype of the type defined herein. Reference to inducing mesenchymal to epithelial transition should be understood to have the converse meaning.

In a disease or condition of the invention, EMT may be detectable before the onset of the disease or condition i.e. before the appearance of a symptom of said disease or condition. It is further encompassed by the present invention that EMT is detectable during the development of said disease or condition, i.e. after the apparition of a symptom of said disease or condition. It is also further encompassed that EMT is detectable before the onset of the disease or condition and during the development of said disease or condition.

EMT may be detected using any technique known to the skilled person. Preferably, EMT is assessed by detecting a decrease of the expression of epithelial E-cadherin and/or an increase of the expression of mesenchymal vimentin and/or mesenchymal cadherin using immunohistochemistry using specific antibodies raised against E-cadherin and/or mesenchymal vimentin and/or mesenchymal cadherin respectively (2, 3). N-cadherin (CDH2) and OB-cadherin (CDH11) are two examples of mesenchymal cadherins. The assessment of the expression is preferably carried out in a tumor biopsy or section at several time points for a given subject or at one or several time points for a given subject and a healthy control. The assessment may be carried out each week, each month. The increase/decrease may therefore be assessed each week, month.

Preferably, a decrease of the expression of epithelial E-cadherin means a significant decrease, preferably a decrease of at least 5% of the expression using immunohistochemistry. More preferably, a decrease means a decrease of at least 10%, even more preferably at least 20%, at least 30%, at least 40%, at least 50%, at least 70%, at least 90%, or 100%. In this case, no expression is detectable. A 25 fold increase of E-cadherin was obtained using a miRNA-520f molecule as identified herein (a representative example is shown in example 2, FIG. 4B). The effect of this miRNA molecule on this marker is quantitatively (at least 1.5 fold) more pronounced than the corresponding effect of miRNA molecule of the 200 family that were already known to have an effect on E-cadherin as shown in in example 2, FIG. 4B. We therefore may anticipate that a miRNA-520f molecule as identified herein may be considered as an attractive molecule for a use as identified herein.

Preferably, an increase of the expression mesenchymal vimentin and/or mesenchymal cadherin means a significant increase, preferably an increase of at least 5% of the expression using immunohistochemistry. More preferably, an increase means an increase of at least 10%, even more preferably at least 20%, at least 30%, at least 40%, at least 50%, at least 70%, at least 90%, at least 100%, or at least 150% or more.

A disease or condition wherein EMT is involved or associated is preferably a disease or condition wherein a dedifferentiation process occurs. In this dedifferentiation process, a decrease of the expression of epithelial E-cadherin and/or an increase of the expression of mesenchymal vimentin and/or mesenchymal cadherin preferably occurs and may be assessed as explained herein. As an example, EMT may be exhibited by cancer cells which undergo this process and thereby become metastatic due to their ability to separate from neighbouring cells and penetrate into and through surrounding tissues. Therefore, a preferred disease in this context is a cancer (e.g., malignant, metastatic) or a fibrosis. Cancers of a preferred embodiment of the invention include a cancer of epithelial origin or a carcinoma or a solid tumor. Cancer cells may be from the bladder, brain, breast, colon, esophagus, gastrointestine, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease of the breast; acinar cell carcinoma; adenosquamous carcinoma; adenocarcinoma w/squamous metaplasia; ovarian stromal tumor, malignant; androblastoma, malignant; Sertoli cell carcinoma. In a preferred embodiment, the disease or condition associated with EMT is a cancer, preferably a bladder or prostate cancer. EMT does not occur in all cancers. In soft tissue sarcomas and leukemias the dedifferentiation process of EMT does not occur. Therefore in a preferred embodiment, a cancer as identified herein is a carcinoma and/or is not a leukemia and/or is not a tissue sarcoma.

EMT may also occur during chronic inflammation or conditions that promote sustained tissue disruption which can stimulate fibrosis, thereby compromising tissue integrity and organ function. A fibrosis is also known as organ fibrosis or organ degeneration (reviewed in Thierry J. P. et al, 2009, Cell, 139: 871-890). In fibrotic tissues, myofibroblasts accumulate and secrete an excessive amount of collagen that is deposited as fibers, thereby compromising organ function and leading to its failure. Fibrosis originates from the conversion of a significant portion of epithelial cells into myofibroblasts through an EMT process (Iwano et al., 2002 J. Clin. Invest. 110:341-50). Initially demonstrated in differentiated cells of renal tubules and ducts, it is now clear that lens epithelium, endothelium, hepatocytes, and cardiomyocytes can all undergo EMT and contribute significantly to tissue fibrosis. Each fibrosis wherein EMT is supposed or suspected to occur is encompassed within the scope of the invention.

A condition or disease associated with EMT may also be poor wound healing, diabetic renal nephropathy, allograft dysfunction, cataracts or defects in cardiac valve formation.

There is currently no effective known medicament that may be used for specifically preventing, treating, reverting, curing and/or delaying a disease or condition associated with EMT in a subject. The invention encompasses to use a miRNA molecule or an equivalent thereof wherein a source of said miRNA molecule or equivalent thereof comprises at least 80 nucleotides and comprises a motif having at least 98% identity with the motif represented by SEQ ID NO:1 or a composition comprising said miRNA molecule or equivalent thereof or a source thereof to this end. Preferred miRNA molecules or equivalents or mimic or isomiR or sources thereof have already been defined herein.

This use includes pharmacologically increasing an activity or the steady-state level of said miRNA molecule or equivalent thereof or of said source thereof in a subject, in a cell of said subject, in a tissue of said subject or in body fluid of said subject.

In this use, an activity or steady-state level of said miRNA, or equivalent thereof or source thereof is increased in order to induce a detectable MET in a subject. A MET, Mesenchymal to Epithelial Transition is the reverse of an EMT. Therefore, induction of MET is identical to reversion of EMT. Preferably, a MET is assessed by detecting an increase of the expression of epithelial E-cadherin and/or a decrease of the expression of mesenchymal vimentin using immunohistochemistry using a specific antibody raised against E-cadherin, respectively mesenchymal vimentin and/or mesenchymal cadherin (2, 3). The assessment of the expression is preferably carried out in a tumor biopsy or section at several time points for a given subject or at one or several time points for a given subject and a healthy control. The assessment may be carried out at regular time intervals, e.g. each week, each month. The increase/decrease may therefore be assessed regularly, e.g. each week, each month. A MET has been preferably detected when for at least one time point, an increase of the expression of epithelial E-cadherin and/or an decrease of the expression of mesenchymal vimentin and/or mesenchymal Cadherin has been detected. Preferably, a MET has been detected when for at least two, three, four, five time points such increase of the expression of epithelial E-cadherin and/or decrease of the expression of mesenchymal vimentin and/or mesenchymal Cadherin has been detected. Preferably, an increase of the expression of epithelial E-cadherin means a significant increase, preferably an increase of at least 5% of the expression using immunohistochemistry. More preferably, an increase means an increase of at least 10%, even more preferably at least 20%, at least 30%, at least 40%, at least 50%, at least 70%, at least 90%, at least 150% or more.

Preferably, a decrease of the expression mesenchymal vimentin and/or mesenchymal cadherin means a significant decrease, preferably a decrease of at least 5% of the expression using immunohistochemistry. More preferably, a decrease means a decrease of at least 10%, even more preferably at least 20%, at least 30%, at least 40%, at least 50%, at least 70%, at least 90%, or 100%. In this case, no expression is detectable.

An activity or steady-state level of said miRNA molecule or an equivalent or a mimic or an isomiR thereof wherein a source of said miRNA molecule or equivalent or mimic or isomiR thereof comprises at least 80 nucleotides and comprises a motif having at least 98% identity with the motif represented by SEQ ID NO:1 may be increased at the level of the miRNA molecule (or equivalent or mimic or isomiR thereof) itself, e.g. by providing said miRNA molecule or equivalent or mimic or isomiR thereof to a subject, preferably to a cell of a subject, or to a tissue of said subject, or to an organ of said subject or to said subject said miRNA molecule or equivalent or mimic or isomiR thereof being from an exogenous source. For provision of a miRNA molecule or equivalent or mimic or isomiR thereof from an exogenous source, said miRNA molecule or equivalent or mimic or isomiR thereof may conveniently be produced by expression of a nucleic acid encoding said miRNA molecule or equivalent or mimic or isomiR thereof or encoding a source of said miRNA molecule or equivalent or mimic or isomiR thereof in a suitable host cell as described below or as completely synthetic molecules by chemical synthesis.

Preferably, however, an activity or steady-state level of a miRNA molecule or equivalent or a mimic or an isomiR thereof is increased by regulating the expression level of a nucleotide sequence encoding said miRNA molecule or equivalent or mimic or isomiR thereof or encoding a source of said miRNA molecule or equivalent or mimic or isomiR thereof. Preferably, the expression level of a nucleotide sequence is regulated in a cell of said subject or in a tissue of said subject or in the subject. The expression level of a miRNA molecule or equivalent or mimic or isomiR thereof or a source of said miRNA molecule or equivalent or mimic or isomiR thereof may be increased by introduction of a miRNA molecule, or equivalent or mimic or isomer thereof, or a source thereof, or an expression construct (or vector) into a cell, tissue, organ or body fluid of said subject, or in the subject whereby an expression vector comprises a nucleotide sequence comprising a miRNA molecule or equivalent or a mimic or an isomiR thereof or comprising a source of said miRNA molecule or equivalent or a mimic or an isomiR thereof, and whereby a nucleotide sequence is under control of a promoter capable of driving expression of a nucleotide sequence in said cell, tissue, organ, subject. The expression level of a miRNA molecule or equivalent or a mimic or an isomiR thereof or source thereof may also be increased by introduction of an expression construct into a cell, tissue, organ, subject, whereby a construct comprises a nucleotide sequence encoding a factor capable of trans-activation of an endogenous nucleotide sequence encoding a miRNA molecule or equivalent or mimic or isomiR thereof.

A use of the invention preferably comprises the step of administering to a subject a therapeutically effective amount of a pharmaceutical composition comprising a nucleic acid construct for increasing the activity or steady state level of a miRNA molecule or an equivalent or a mimic or an isomiR thereof wherein a source of said miRNA molecule or equivalent or mimic or isomiR thereof comprises at least 80 nucleotides and comprises a motif having at least 98% identity with the motif represented by SEQ ID NO:1 or a source thereof as identified herein. A nucleic acid construct may be an expression construct as further specified herein. Preferably, an expression construct is a viral gene therapy vector selected from gene therapy vectors based on an adenovirus, an adeno-associated virus (AAV), a herpes virus, a pox virus, an oncolytic virus vector and a retrovirus. A preferred viral gene therapy vector is an AAV or Lentiviral vector. Alternatively, a use of the invention preferably comprises the step of administering to a subject a therapeutically effective amount of a pharmaceutical composition comprising a miRNA molecule or an equivalent or a mimic or an isomiR thereof wherein a source of said miRNA molecule or equivalent or mimic or isomiR thereof comprises at least 80 nucleotides and comprises a motif having at least 98% identity with the motif represented by SEQ ID NO:1 or a source thereof as defined herein.

In a use of the invention, a cell, a tissue, an organ or body fluid is preferably from a subject suspected to have a high risk of having an EMT or of having a disease or condition associated with EMT due for example to its age or its genetic background or to its diet. Alternatively, in another preferred embodiment, use of the invention is applied on a cell, tissue, organ or body fluid from a subject diagnosed as either having a predictive risk for developing later a disease or condition associated with EMT. A diagnostic method used is preferably one of the inventions as described herein. Alternatively, a cell, a tissue or organ to be treated may be selected based on risk of progression of the disease or condition associated with EMT. Such risk of progression may be assessed using classical clinic-pathological criteria or biomarker-based prognosis known to the skilled person. It is also encompassed by the invention to administer a miRNA molecule or an equivalent or a mimic or an isomiR thereof wherein a source of said miRNA molecule or equivalent or mimic or isomiR thereof comprises at least 80 nucleotides and comprises a motif having at least 98% identity with the motif represented by SEQ ID NO:1 or a precursor thereof or a composition comprising said miRNAmolecule or equivalent or mimic or isomiR thereof or source thereof into a tissue or organ of said subject. Preferred miRNA molecules or equivalents or mimic or isomiR or sources thereof have already been defined herein. In the invention, a preferred cell, tissue or organ is a cell, tissue or organ that is or comprises a bladder or prostate cell or tissue or is or comprises the bladder or prostate as organ.

A treatment of a disease or condition associated with EMT may include a treatment that prevents EMT in a tumor cell that has not yet metastasized or revert EMT (defined as Mesenchymal to Epithelial Transition) in a tumor cell that has already formed metastases and/or is migrating from the primary tumor to distant sites in the body.

In another use, the invention mentioned herein may be combined with standard treatments of disease or condition associated with EMT such as chemotherapy, radiotherapy or surgery. Examples of chemotherapeutic agents are exemplified later herein.

Although gene therapy is a possibility for preventing, treating, reverting and/or delaying a condition or a disease associated with EMT, other possible treatments may also be envisaged. For example, treatment by "small molecule" drugs to steer certain molecular pathways in the desired direction, is also preferred. These small molecules are preferably identified by the screening method of the invention as defined later herein.

In the context of the invention, preventing, treating, reverting, curing and/or delaying a disease or condition associated with EMT may mean that:
  At least a symptom of this disease or condition has been improved, and/or
  At least a parameter associated with this disease or condition has been improved.

A symptom may be the presence of metastases as explained below. A parameter may be the assessment of MET as explained earlier herein. In the context of the invention, preventing, treating, reverting, curing and/or delaying a disease or condition associated with EMT may be replaced by achieving an anti-tumor effect. Unless otherwise indicated, an anti-tumor effect is preferably assessed or detected after at least one week, two weeks, three weeks, fours weeks, one month, two months, three months, four months, five months, six months or more in a treated subject. An anti-tumor effect is preferably identified in a subject as:
  an inhibition of proliferation of tumor cells and/or
  an increase in the capacity of differentiation of tumor cells and/or
  an induction or increased induction of tumor cells death and/or
  a delay in occurrence of metastases and/or of tumor cell migration and/or
  an inhibition or prevention or delay of the increase of a tumor weight or growth and/or
  a prolongation of patient survival of at least one month, several months or more (compared to those not treated or treated with a control or compared with the subject at the onset of the treatment).

In the context of the invention, a patient may survive and/or may be considered as being disease free. Alternatively, the disease or condition may have been stopped or delayed. An inhibition of the proliferation of tumor cells may be at least 20%, 30%, 40%, 50%, 55%, 60%, 65%, 70% or 75%, or more. Proliferation of cells may be assessed using known techniques.

An induction of tumor cell death may be at least 1%, 5%, 10%, 15%, 20%, 25%, or more. Tumor growth may be inhibited at least 5%, 10%, 20%, 30%, 40%, 50%, 55%, 60%, 65%, 70% or 75%, or more. Tumor cell death may be assessed using techniques known to the skilled person. Tumor cell death may be assessed using MRI (Magnetic Resonance Imaging) or CT (Computer Tomography).

In certain embodiments, tumor weight increase or tumor growth may be inhibited at least 20%, 30%, 40%, 50%, 55%, 60%, 65%, 70% or 75%, or more. Tumor weight or tumor growth may be assessed using techniques known to the skilled person.

The detection of tumor growth or the detection of the proliferation of tumor cells may be assessed in vivo by measuring changes in glucose utilization by positron emission tomography with the glucose analogue 2-[18F]-fluor-2-deoxy-D-glucose (FDG-PET) or [18F]-'3-fluoro-'3-deoxy-L-thymidine PET. An ex vivo alternative may be staining of a tumor biopsy with Ki67.

A delay in occurrence of metastases and/or of tumor cell migration may be a delay of at least one week, one month, several months, one year or longer. The presence of metastases may be assessed using MRI, CT or Echography or techniques allowing the detection of circulating tumour cells (CTC). Examples of the latter tests are CellSearch CTC test (Veridex), an EpCam-based magnetic sorting of CTCs from peripheral blood. In certain embodiments, tumor growth may be delayed at least one week, one month, two months or more. In a certain embodiment, an occurrence of metastases is delayed at least one week, two weeks, three weeks, fours weeks, one months, two months, three months, four months, five months, six months or more. A miRNA molecule or an equivalent or a mimic or an isomiR thereof or a source thereof wherein a source of said miRNA molecule or equivalent or mimic or isomiR thereof comprises at least 80 nucleotides and comprises a motif having at least 98% identity with the motif represented by SEQ ID NO:1 had been surprisingly found to delay the occurrence of metastases and/or tumor cell migration in a more pronounced fashion than the corresponding effect of miRNA molecule of the 200 family that were already known to have such an effect as shown in Example 2, FIG. 6D. We therefore may anticipate that a miRNA molecule or a source thereof as identified herein may be considered as an attractive molecule for a use as identified herein.

An increase in the capacity of differentiation of tumor cells may be assessed using a specific differentiation marker and following the presence of such marker on cells treated. Preferred markers or parameters have already been identified herein, i.e. markers associated with MET. This may be done using RT-PCR, western blotting or immunohistochemistry. An increase of the capacity of differentiation may be at least a detectable increase after at least one week of treatment using any of the identified techniques. Preferably, the increase is of 1%, 5%, 10%, 15%, 20%, 25%, or more, which means that the number of differentiated cells within a given sample will increase accordingly. In certain embodiments, tumor growth may be delayed at least one week, one month, two months or more. In a certain embodiment, an occurrence of metastases is delayed at least one week, two weeks, three weeks, fours weeks, one months, two months, three months, four months, five months, six months or more.

In a further preferred embodiment, there is provided a composition further comprising another miRNA molecule selected from:
a) at least one of miRNA-124-1, miRNA-206, miRNA-181a-1, miRNA-141, miRNA-200a, miRNA-200b, miRNA-200c, miRNA-429 and miRNA-205 and/or an equivalent or a mimic or an isomiR or a source thereof.

Since not each of the identified miRNAs molecules or equivalents or isomiRs or mimics thereof is expected to have the same target genes, it is assumed that the use of a miRNA molecule or an equivalent or an isomiR or a mimic thereof wherein a source of said miRNA molecule or equivalent or isomiR or mimic thereof comprises at least 80 nucleotides and comprises a motif having at least 98% identity with the motif represented by SEQ ID NO:1 optionally combined with at least one of the miRNAs molecule, or equivalent or isomiR or mimic thereof or source thereof identified above under a) allows a more effective treatment of a disease or condition associated with EMT. Preferred miRNA molecules or equivalents or mimic or isomiR or sources thereof have already been defined herein. A tumor treated by a composition or a cocktail of at least a miRNA molecule or an equivalent or an isomiR or a mimic thereof wherein a source of said miRNA molecule or equivalent thereof comprises at least 80 nucleotides and comprises a motif having at least 98% identity with the motif represented by SEQ ID NO: 1 is expected to have fewer possibilities to escape or to resist said treatment. In a further preferred embodiment, it is encompassed to diagnose the expression of each of the miRNA molecules or of their target genes as identified herein and depending on the outcome to adapt the identity of the miRNA molecules used for the treatment.

When the invention relates to a composition comprising more than one miRNA molecule or equivalent or isomiR or mimic thereof or source thereof, it is encompassed that each miRNA molecule or equivalent or isomiR or mimic thereof or source thereof may be present each in a separate composition, each composition being sequentially or simultaneously administered to a subject. Alternatively, it is also encompassed that more than one miRNA molecules or equivalents or isomiRs or mimics thereof or sources thereof is present in a composition as defined herein.

In a further aspect, there is provided the use of a miRNA molecule or an equivalent or an isomiR or a mimic thereof wherein a source of said miRNA molecule or equivalent or isomiR or mimic thereof comprises at least 80 nucleotides and comprises a motif having at least 98% identity with the motif represented by SEQ ID NO:1 or a source thereof or a composition comprising said miRNA molecule, an equivalent or isomiR or mimic or a source thereof for the manufacture of a medicament for preventing, treating, reverting, curing and/or delaying a disease or a condition associated with EMT. Each feature of this further aspect has already been described herein.

In a further aspect, there is provided a method for preventing preventing, treating, reverting, curing and/or delaying a condition or disease associated with EMT by administering a miRNA molecule or equivalent or isomiR or mimic thereof or source thereof or composition as earlier defined herein to a subject in the need thereof. Each feature of this further aspect has already been described herein.

In a further aspect, there is provided a method for diagnosing EMT or a disease or condition associated with EMT in a subject, the method comprising the steps of:
(a) determining the expression level of a miRNA molecule or an equivalent or isomiR or mimic thereof wherein a source of said miRNA molecule or equivalent or isomiR or mimic thereof comprises at least 80 nucleotides and comprises a motif having at least 98% identity with the motif represented by SEQ ID NO:1 or a source thereof in a subject, and optionally
(b) comparing the expression level of said molecule or equivalent thereof or source thereof as defined in (a) with a reference value for the expression level of said molecule, equivalent, isomiR, mimic or source thereof, the reference value preferably being the average value for the expression level of said molecule, equivalent, isomiR, mimic or source thereof in a healthy subject.

In the context of the invention, diagnosis means either a predictive risk assessment of a subject for developing a disease or a condition associated EMT or for developing EMT itself. In the context of the invention, a subject may be an animal. Preferably a subject is a mammal. Preferred mammal is a human being. Preferably, a subject is a human being.

Since the expression levels of these nucleotide sequences and/or amounts of corresponding miRNA molecule or equivalent or isomiR or mimic thereof or source thereof may be difficult to be measured in a subject, a sample from a subject is preferably used. According to another preferred embodiment, the expression level (of a nucleotide sequence or miRNA molecule or equivalent or isomiR or mimic or source thereof) is determined ex vivo in a sample obtained from a subject. The sample preferably comprises a body fluid of a subject. A body fluid may comprise or be derived from blood, serum, plasma, stool, urine or a tissue biopsy or a tumor biopsy or a cancer tissue of epithelial origin of a subject. Preferred tissue is bladder or prostate. It is specifically contemplated that the invention can be used to evaluate or diagnose differences between stages of disease or condition associated with EMT, such as between pre-cancer and cancer, or between a primary tumor and a metastasized tumor.

An increase or decrease of the expression level of a nucleotide sequence (or steady state level of the encoded miRNA molecule or equivalent or isomiR or mimic or source thereof) is preferably defined as being a detectable change of the expression level of a nucleotide (or steady state level of an encoded miRNA molecule or equivalent or isomiR or mimic or source thereof or any detectable change in a biological activity of a miRNA molecule or equivalent or isomiR or mimic or source thereof) using a method as defined earlier on as compared to the expression level of a corresponding nucleotide sequence (or steady state level of a corresponding encoded miRNA molecule or equivalent or isomiR or mimic or source thereof) in a healthy subject. A preferred nucleotide sequence is a sequence encoding a precursor of a miRNA molecule or equivalent or isomiR or mimic thereof or a precursor sequence of a miRNA molecule or equivalent or isomiR or mimic thereof. According to a preferred embodiment, an increase or decrease of a miRNA activity is quantified using a specific assay for a miRNA activity. A preferred assay is the assessment of MET as earlier defined herein.

Preferably, a decrease of the expression level of a nucleotide sequence means a decrease of at least 5% of the expression level of the nucleotide sequence using arrays. More preferably, a decrease of the expression level of a nucleotide sequence means an decrease of at least 10%, even more preferably at least 20%, at least 30%, at least 40%, at least 50%, at least 70%, at least 90%, or 100%. In this case, there is no detectable expression.

Preferably, a decrease of the expression level of a miRNA molecule or equivalent or isomiR or mimic or source thereof means a decrease of at least 5% of the expression level of the miRNA using qPCR, microarrays or Northernblot analysis. Preferably qPCR is stem-loop RT qPCR. More preferably, a decrease of the expression level of a miRNA molecule or equivalent or isomiR or mimic or source thereof means a decrease of at least 10%, even more preferably at least 20%, at least 30%, at least 40%, at least 50%, at least 70%, at least 90%, or 100%. In this case, there is no detectable expression.

Preferably, a decrease of a miRNA activity means a decrease of at least 5% of a miRNA activity using a suitable assay. More preferably, a decrease of a miRNA activity means a decrease of at least 10%, even more preferably at least 20%, at least 30%, at least 40%, at least 50%, at least 70%, at least 90%, or 100%. In this case, there is no detectable expression.

Preferably, an increase of the expression level of a nucleotide sequence means an increase of at least 5% of the expression level of the nucleotide sequence using any of the techniques mentioned herein. More preferably, an increase of the expression level of a nucleotide sequence means an increase of at least 10%, even more preferably at least 20%, at least 30%, at least 40%, at least 50%, at least 70%, at least 90%, at least 150% or more.

Preferably, an increase of the expression level of a miRNA molecule or equivalent or isomiR or mimic or source thereof means an increase of at least 5% of the expression level of the miRNA molecule or equivalent or isomiR or mimic or source thereof using RT-qPCR, preferably stem-loop RT qPCR. More preferably, an increase of the expression level of a miRNA molecule or equivalent or isomiR or mimic or source thereof means an increase of at least 10%, even more preferably at least 20%, at least 30%, at least 40%, at least 50%, at least 70%, at least 90%, at least 150% or more.

Preferably, an increase of a miRNA activity means an increase of at least 5% of a miRNA activity using a suitable assay. More preferably, an increase of a miRNA activity means an increase of at least 10%, even more preferably at least 20%, at least 30%, at least 40%, at least 50%, at least 70%, at least 90%, at least 150% or more.

Preferably, an expression level is determined ex vivo in a sample obtained from a subject. More preferably, the sample is as earlier defined herein and wherein subsequently, a given nucleotide sequence and/or miRNA molecule or equivalent or isomiR or mimic or source thereof is extracted and purified using known methods to the skilled person. More preferably, the sample is or comprises or is derived from a tumor biopsy, blood or urine.

In a diagnostic method of the invention preferably the expression level of more than one, more preferably of at least 2, 3, 4, 5, 6, 7, 8, 9, 10, 11, 12, 13, 14, 15 miRNAs molecule or equivalent or isomiR or mimic or source thereof and/or the steady state levels of the corresponding miRNAs molecule or equivalent or isomiR or mimic or source thereof are determined.

Accordingly in a preferred method, in step (a) one determines the expression level of another miRNA molecule or equivalent or source thereof selected from:
(a) at least one of miRNA-124-1, miRNA-206, miRNA-181a-1, miRNA-141, miRNA-200a, miRNA-200b miRNA-200c, miRNA-429 and miRNA-205 and/or an equivalent or a source thereof.

In a further preferred method, EMT or a disease or condition associated with EMT is diagnosed when the comparison leads to the finding of a decrease of the expression level of said miRNA molecule or an equivalent or a mimic or an isomiR thereof wherein a source of said miRNA molecule or equivalent thereof comprises at least 80 nucleotides and comprises a motif having at least 98% identity with the motif represented by SEQ ID NO:1. More preferred miRNA molecules or an equivalents or mimics or isomiRs or sources thereof have all been defined earlier herein.

In a further preferred method, EMT or a disease or condition associated with EMT is diagnosed when the comparison leads to the finding of a decrease of the expression level of miRNA molecule or an equivalent thereof wherein a source of said miRNA molecule or equivalent thereof comprises at least 80 nucleotides and comprises a motif having at least 98% identity with the motif represented by SEQ ID NO:1 or a source thereof and a decrease of the expression level of at least one of another miRNA selected from:
(a) at least one of miRNA-124-1, miRNA-206, miRNA-181a-1, miRNA-141, miRNA-200a, miRNA-200b, miRNA-200c, miRNA-429 and miRNA-205 and/or an equivalent or a mimic or an isomiR or a source thereof.

In a further aspect, there is provided a method for identification of a substance or a molecule capable of preventing, treating, reverting, curing and/or delaying EMT or a condition or disease associated with EMT in a subject, the method comprising the steps of:
(a) providing a test cell population capable of expressing a miRNA molecule or an equivalent or a mimic or an isomiR thereof, wherein a source of said miRNA molecule or equivalent or mimic or isomiR thereof comprises at least 80 nucleotides and comprises a motif having at least 98% identity with the motif represented by SEQ ID NO:1 or source thereof, preferably the test population comprises bladder or prostate cells, and/or the test cell population comprises cancer cells and/or the test cell population comprises mammalian cells, and/or the test cell population comprises human cells;
(b) contacting the test cell population with the substance;
(c) determining the expression level of said miRNA molecule or equivalent or mimic or isomiR thereof or source thereof or the activity or steady state level of said miRNA molecule or equivalent or mimic or isomiR thereof or source thereof in the test cell population contacted with the substance;
(d) comparing the expression, activity or steady state level determined in (c) with the expression, activity or steady state level of said miRNA molecule or equivalent or mimic or isomiR thereof or source thereof in a test cell population that is not contacted with the substance; and,
(e) identifying a substance that produces a difference in expression level, activity or steady state level of said miRNA molecule or equivalent or mimic or isomiR thereof or source thereof, between the test cell population that is contacted with the substance and the test cell population that is not contacted with the substance.

Preferably, in step a), a test cell comprises a nucleic acid construct comprising a source or a precursor of a miRNA molecule or an equivalent or a mimic or an isomiR thereof wherein a source or a precursor of said miRNA molecule or equivalent or mimic or isomiR thereof comprises at least 80 nucleotides and comprises a motif having at least 98% identity with the motif represented by SEQ ID NO:1. More preferred miRNA molecules or an equivalents or mimics or isomiRs or sources thereof have all been defined earlier herein. More preferably, a test cell comprises a CDH1 promotor driven firefly luciferase construct. Preferably, in a method the expression levels, an activity or steady state levels of more than one nucleotide sequence or more than one miRNA molecule, equivalent or mimic or isomiR or source thereof are compared. Preferably, in a method, a test cell population comprises mammalian cells, more preferably human cells. Even more preferably, a test cell population comprises bladder or prostate cells. A preferred test cell population does not express a miRNA molecule or an equivalent or a mimic or an isomiR thereof wherein a source of said miRNA molecule or equivalent thereof comprises at least 80 nucleotides and comprises a motif having at least 98% identity with the motif represented by SEQ ID NO:1 or source thereof or has a reduced expression compared to a normal epithelial counterpart that expresses CDH1. More preferably, a test cell population comprises a mesenchymal cell with low CDH1 expression, but is capable of expressing CDH1. Alternatively or in addition to previous mentioned cells, in one aspect the invention also pertains to a substance that is identified in the aforementioned methods.

In a preferred method, the expression levels, activities or steady state levels of at least another one miRNA molecule or equivalent or mimic or isomiR or source thereof is compared, preferably wherein the other miRNA molecule or equivalent or mimic or isomiR or source thereof is selected from:

(a) at least one of miRNA-124-1, miRNA-206, miRNA-181a-1, miRNA-141, miRNA-200a, miRNA-200b, miRNA-200c, miRNA-429 and miRNA-205 and/or an equivalent, a mimic or an isomiR or a source thereof.

General Definitions and General Technologies Referred to Herein

MicroRNA molecules ("miRNAs") are generally 21 to 22 nucleotides in length, though lengths of 17 and up to 25 nucleotides have been reported. Any length of 17, 18, 19, 20, 21, 22, 23, 24, 25 is therefore encompassed within the present invention. The miRNAs are each processed from a longer precursor RNA molecule ("precursor miRNA"). Precursor miRNAs are transcribed from non-protein-encoding genes. A precursor may have a length of at least 50, 70, 75, 80, 85, 100, 150, 200 nucleotides or more. The precursor miRNAs have two regions of complementarity that enables them to form a stem-loop- or fold-back-like structure, which is cleaved by enzymes called Dicer and Drosha in animals. Dicer and Drosha are ribonuclease Ill-like nucleases. The processed miRNA is typically a portion of the stem.

The processed miRNA (also referred to as "mature miRNA") becomes part of a large complex, known as the RNA-Induced Silencing Complex (RISC) complex, to (down)-regulate a particular target gene. Examples of animal miRNAs include those that perfectly or imperfectly basepair with the mRNA target, resulting in either mRNA degradation or inhibition of translation respectively (Olsen et al, 1999; Seggerson et al, 2002). SiRNA molecules also are processed by Dicer, but from a long, double-stranded RNA molecule. SiRNAs are not naturally found in animal cells, but they can function in such cells in a RNA-induced silencing complex (RISC) to direct the sequence-specific cleavage of an mRNA target (Denli et al, 2003).

The study of endogenous miRNA molecules is described in U.S. Patent Application 60/575,743, which is hereby incorporated by reference in its entirety. A miRNA is apparently active in the cell when the mature, single-stranded RNA is bound by a protein complex that regulates the translation of mRNAs that hybridize to the miRNA. Introducing exogenous RNA molecules that affect cells in the same way as endogenously expressed miRNAs requires that a single-stranded RNA molecule of the same sequence as the endogenous mature miRNA be taken up by the protein complex that facilitates translational control. A variety of RNA molecule designs have been evaluated. Three general designs that maximize uptake of the desired single-stranded miRNA by the miRNA pathway have been identified. An RNA molecule with a miRNA sequence having at least one of the three designs may be referred to as a synthetic miRNA.

miRNA molecules of the invention can replace or supplement the gene silencing activity of an endogenous miRNA. An example of such molecules, preferred characteristics and modifications of such molecules and compositions comprising such molecules is described in WO2009/091982, which is hereby incorporated by reference in its entirety.

miRNA molecules of the invention or equivalents or source thereof comprise, in some embodiments, two RNA molecules wherein one RNA is identical to a naturally occurring, mature miRNA. The RNA molecule that is identical to a mature miRNA is referred to as the active strand. The second RNA molecule, referred to as the complementary strand, is at least partially complementary to the active strand. The active and complementary strands are hybridized to create a double-stranded RNA, that is similar to the naturally occurring miRNA precursor that is bound by the protein complex immediately prior to miRNA activation in the cell. Maximizing activity of said miRNA requires maximizing uptake of the active strand and minimizing uptake of the complementary strand by the miRNA protein complex that regulates gene expression at the level of translation. The molecular designs that provide optimal miRNA activity involve modifications of the complementary strand.

Two designs incorporate chemical modifications of the complementary strand.

The first modification involves creating a complementary RNA with a group other than a phosphate or hydroxyl at its 5' terminus. The presence of the 5' modification apparently eliminates uptake of the complementary strand and subsequently favors uptake of the active strand by the miRNA protein complex. The 5' modification can be any of a variety of molecules including $NH_2$, $NHCOCH_3$, biotin, and others.

The second chemical modification strategy that significantly reduces uptake of the complementary strand by the miRNA pathway is incorporating nucleotides with sugar modifications in the first 2-6 nucleotides of the complementary strand. It should be noted that the sugar modifications consistent with the second design strategy can be coupled with 5' terminal modifications consistent with the first design strategy to further enhance miRNA activities.

The third miRNA design involves incorporating nucleotides in the 3' end of the complementary strand that are not complementary to the active strand.

Hybrids of the resulting active and complementary RNAs are very stable at the 3' end of the active strand but relatively unstable at the 5' end of the active strand. Studies with siRNAs indicate that 5' hybrid stability is a key indicator of RNA uptake by the protein complex that supports RNA interference, which is at least related to the miRNA pathway in cells. The inventors have found that the judicious use of mismatches in the complementary RNA strand significantly enhances the activity of said miRNA.

MiRNA Libraries

A key application for the miRNAs as identified herein is the assessment or diagnosis of the presence of one individual or groups of miRNAs in a sample. Cell populations with each of the different miRNAs can then be assayed to identify miRNAs whose presence affects a cellular phenotype (i.e. EMT). The number of different miRNAs in the libraries is variable. It is contemplated that there may be, be at least, or be at most 1, 2, 3, 4, 5, 6, 7, 8, 9, 10, 11, 12, 13, 14, 15, 16, 17, 18, 19, 20 or more, or any range derivable therein, different miRNA-specific molecules in the library. In specific embodiments, libraries have 1 to 20 different miRNA-specific molecules, or 5 to 20 different miRNA-specific molecules. "Different" miRNA-specific molecules refers to nucleic acids that specifically encode miRNAs with different sequences.

miRNAs are contemplated to be made primarily of RNA, though in some embodiments, they may be RNA, nucleotide analogs, such as Locked nucleic acids (LNA) or Unlocked nucleic acids (UNA), DNA, or any combination of DNA, RNA, nucleotide analogs, and PNAs (Peptide Nucleic Acids). Accordingly, it is understood that the library contains one or more nucleic acids for these different miRNAs. In specific embodiments, the library is specific to human miRNAs, though libraries for multiple organisms are contemplated.

An RNA molecule of the invention has or comprises or consists of a miRNA region. In specific embodiments, a miRNA molecule or equivalent thereof has a sequence that derives from any of SEQ ID NOs: 2-21 inclusive (Table 3). It is particularly contemplated that nucleic acid molecules of the invention may be derived from any of the mature miRNA sequences in SEQ ID NOs: 2-21.

A miRNA molecule or equivalent thereof will include a sequence that extends at least 1 to 5 nucleotides of coding sequence upstream and/or downstream of the predicted miRNA sequence. In some embodiments, molecules have up to 1, 2, 3, 4, 5, 6, 7, or more contiguous nucleotides, or any range derivable therein, that flank the sequence encoding the predominant processed miRNA on one or both sides (5' and/or 3' end).

Libraries of the invention can contain miRNA sequences from any organism having miRNAs, specifically including but not limited to, mammals such as humans, non human primates, rats and mice. Specifically contemplated are libraries having, having at least, or having at most 1, 2, 3, 4, 5, 6, 7, 8, 9, 10, 11, 12, 13, 14, 15, 16, 17, 18, 19, 20 or more different miRNAs (that is, miRNA-specific molecules having different sequences derived from different miRNA genes). Specifically contemplated are such libraries described in the previous sentence with respect to any of SEQ ID NOs: 2-21 particularly those corresponding to miRNA sequences (mature sequence).

Nucleic Acids

The present invention concerns nucleic acid molecules also called sources or precursors of miRNAs that can introduce miRNAs in cultured cells or into a subject. The nucleic acids may have been produced in cells or in vitro by purified enzymes though they are preferentially produced by chemical synthesis. They may be crude or purified. The term "miRNA," unless otherwise indicated, refers to the processed miRNA, after it has been cleaved from its precursor. Table 2 indicates which SEQ ID NO corresponds to a particular precursor sequence of a miRNA (SEQ ID NO: 22-35 and Table 3 which SEQ ID NO corresponds to the mature sequence of a miRNA (SEQ ID NO: 2-21. Table 4 identifies the cloned DNA sequences into the lentiviral vector (SEQ ID NO: 36-47, which were used in the functional screen as described in the examples. Table 5 identifies the preferred seed sequence (as SEQ ID NO: 87-107) of each of the mature miRNAs of Table 3. The name of the miRNA is often abbreviated and referred to without the prefix and will be understood as such, depending on the context. Unless otherwise indicated, miRNAs referred to in the application are human sequences identified as mir-X or let-X, where X is a number and/or letter.

It is understood that a miRNA is derived from genomic sequences or a non-coding gene. In this respect, the term "gene" is used for simplicity to refer to the genomic sequence encoding the precursor miRNA for a given miRNA. However, embodiments of the invention may involve genomic sequences of a miRNA that are involved in its expression, such as a promoter or other regulatory sequences.

The term "recombinant" may be used and this generally refers to a molecule that has been manipulated in vitro or that is the replicated or expressed product of such a molecule.

The term "nucleic acid" is well known in the art. A "nucleic acid" as used herein will generally refer to a molecule (one or more strands) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompasses the terms "oligonucleotide" and "polynucleotide," each as a subgenus of the term "nucleic acid."

The term "miRNA" generally refers to a single-stranded molecule, but in specific embodiments, molecules implemented in the invention will also encompass a region or an additional strand that is partially (between 10 and 50% complementary across length of strand), substantially (greater than 50% but less than 100% complementary across length of strand) or fully complementary to another region of the same single-stranded molecule or to another nucleic acid. Thus, nucleic acids may encompass a molecule that comprises one or more complementary or self-complementary strand(s) or "complement(s)" of a particular sequence comprising a molecule. For example, precursor miRNA may have a self-complementary region, which is up to 100% complementary.

As used herein, "hybridization", "hybridizes" or "capable of hybridizing" is understood to mean the forming of a double or triple stranded molecule or a molecule with partial double or triple stranded nature using techniques known to the skilled person such as southern blotting procedures. The term "anneal" as used herein is synonymous with "hybridize." The term "hybridization", "hybridize(s)" or "capable of hybridizing" may mean "low", "medium" or "high" hybridization conditions as defined below. Low to medium to high stringency conditions means prehybridization and hybridization at 42° C. in 5×SSPE, 0.3% SDS, 200 pg/ml sheared and denatured salmon sperm DNA, and either 25% 35% or 50% formamide for low to medium to high stringencies respectively. Subsequently, the hybridization reaction is washed three times for 30 minutes each using 2×SSC, 0.2% SDS and either 55° C., 65° C., or 75° C. for low to medium to high stringencies.

Nucleic acids or derivatives thereof of the invention will comprise, in some embodiments the miRNA sequence of any miRNA described in SEQ ID NOs: 2-21 or are described in SEQ ID NO: 22-35 or in SEQ ID NO: 36-47. It is contemplated that nucleic acids sequences of the invention derived from SEQ ID NO: 2-21 can have, have at least, or have at most 5, 6, 7, 8, 9, 10, 11, 12, 13, 14, 15, 16, 17, 18, 19, 20, 21, 22, 23, contiguous nucleotides from SEQ ID NOs: 2-21 (or any range derivable therein). In other embodiments, nucleic acids are, are at least, or are at most 80, 81, 82, 83, 84, 85, 86, 87, 88, 89, 90, 91, 92, 93, 94, 95, 96, 97, 98, 99, 100% identical to the miRNA sequence of SEQ ID NOs: 2-21 or to the precursor sequence of any of SEQ ID NO: 22-35 or any combination or range derivable therein.

Nucleobases

As used herein a "nucleobase" refers to a heterocyclic base, such as for example a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in a manner that may substitute for naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof, including but not limited to, those a purine or pyrimidine substituted by one or more of an alkyl, caboxyalkyl, amino, hydroxyl, halogen (i.e., fluoro, chloro, bromo, or iodo), thiol or alkylthiol moeity. Preferred alkyl (e.g., alkyl, caboxyalkyl, etc.) moieties comprise of from about 1, about 2, about 3, about 4, about 5, to about 6 carbon atoms. Other non-limiting examples of a purine or pyrimidine include a deazapurine, a 2,6-diaminopurine, a 5-fluorouracil, a xanthine, a hypoxanthine, a 8-bromoguanine, a 8-chloroguanine, a bromothymine, a 8-aminoguanine, a 8-hydroxyguanine, a 8-methylguanine, a 8-thioguanine, an azaguanine, a 2-aminopurine, a 5-ethylcytosine, a 5-methylcyosine, a 5-bromouracil, a 5-ethyluracil, a 5-iodouracil, a 5-chlorouracil, a 5-propyluracil, a thiouracil, a 2-methyladenine, a methylthioadenine, a N,N-diemethyladenine, an azaadenines, a 8-bromoadenine, a 8-hydroxyadenine, a 6-hydroxyaminopurine, a 6-thiopurine, a 4-(6-aminohexyl/cytosine), and the like. Other examples are well known to those of skill in the art.

A nucleobase may be comprised in a nucleoside or nucleotide, using any chemical or natural synthesis method described herein or known to one of ordinary skill in the art. Such nucleobase may be labeled or it may be part of a molecule that is labeled and contains the nucleobase.

Nucleosides

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring.

Different types of covalent attachment(s) of a nucleobase to a nucleobase linker moiety are known in the art. By way of non-limiting example, a nucleoside comprising a purine (i.e., A or G) or a 7-deazapurine nucleobase typically covalently attaches the 9 position of a purine or a 7-deazapurine to the 1'-position of a 5-carbon sugar. In another non-limiting example, a nucleoside comprising a pyrimidine nucleobase (i.e., C, T or U) typically covalently attaches a 1 position of a pyrimidine to a 1'-position of a 5-carbon sugar (Kornberg and Baker, 1992).

Nucleotides

As used herein, a "nucleotide" refers to a nucleoside further comprising a "backbone moiety". A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphorus moiety.

Nucleic Acid Analogs

A nucleic acid may comprise, or be composed entirely of, a derivative or analog of a nucleobase, a nucleobase linker moiety and/or backbone moiety that may be present in a naturally occurring nucleic acid. RNA with nucleic acid analogs may also be labeled according to methods of the invention. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. As used herein, a "moiety" generally refers to a smaller chemical or molecular component of a larger chemical or molecular structure. Nucleobase, nucleoside and nucleotide analogs or derivatives are well known in the art, and have been described (see for example, Scheit, 1980, incorporated herein by reference).

Additional non-limiting examples of nucleosides, nucleotides or nucleic acids comprising 5-carbon sugar and/or backbone moiety derivatives or analogs, include those in: U.S. Pat. No. 5,681,947, which describes oligonucleotides comprising purine derivatives that form triple helixes with and/or prevent expression of dsDNA; U.S. Pat. Nos. 5,652, 099 and 5,763,167, which describe nucleic acids incorporating fluorescent analogs of nucleosides found in DNA or RNA, particularly for use as fluorescent nucleic acids probes; U.S. Pat. No. 5,614,617, which describes oligonucleotide analogs with substitutions on pyrimidine rings that possess enhanced nuclease stability; U.S. Pat. Nos. 5,670,663, 5,872,232 and 5,859,221, which describe oligonucleotide analogs with modified 5-carbon sugars (i.e., modified T-deoxyfuranosyl moieties) used in nucleic acid detection; U.S. Pat. No. 5,446, 137, which describes oligonucleotides comprising at least one 5-carbon sugar moiety substituted at the 4' position with a substituent other than hydrogen that can be used in hybridization assays; U.S. Pat. No. 5,886,165, which describes oligonucleotides with both deoxyribonucleotides with 3'-5' internucleotide linkages and ribonucleotides with 2'-5' internucleotide linkages; U.S. Pat. No. 5,714,606, which describes a modified internucleotide linkage wherein a 3'-position oxygen of the internucleotide linkage is replaced by a carbon to enhance the nuclease resistance of nucleic acids; U.S. Pat. No. 5,672,697, which describes oligonucleotides containing one or more 5' methylene phosphonate internucleotide linkages that enhance nuclease resistance; U.S. Pat. Nos. 5,466, 786 and 5,792,847, which describe the linkage of a substituent moiety which may comprise a drug or label to the 2' carbon of an oligonucleotide to provide enhanced nuclease stability and ability to deliver drugs or detection moieties; U.S. Pat. No. 5,223,618, which describes oligonucleotide analogs with a 2' or 3' carbon backbone linkage attaching the 4' position and 3' position of adjacent 5-carbon sugar moiety to enhanced cellular uptake, resistance to nucleases and hybridization to target RNA; U.S. Pat. No. 5,470,967, which describes oligonucleotides comprising at least one sulfamate or sulfamide internucleotide linkage that are useful as nucleic acid hybridization probe; U.S. Pat. Nos. 5,378,825, 5,777, 092, 5,623,070, 5,610,289 and 5,602,240, which describe oligonucleotides with three or four atom linker moiety replacing phosphodiester backbone moiety used for improved nuclease resistance, cellular uptake and regulating RNA expression; U.S. Pat. No. 5,858,988, which describes hydrophobic carrier agent attached to the 2'-0 position of oligonucleotides to enhanced their membrane permeability and stability; U.S. Pat. No. 5,214,136, which describes oligonucleotides conjugated to anthraquinone at the 5' terminus that possess enhanced hybridization to DNA or RNA;

enhanced stability to nucleases; U.S. Pat. No. 5,700,922, which describes PNA-DNA-PNA chimeras wherein the DNA comprises 2'-deoxy-erythro-pentofuranosyl nucleotides for enhanced nuclease resistance, binding affinity, and ability to activate RNase H; and WO98/39352, WO99/14226, WO2003/95467 and WO2007/085485, which describe modified RNA nucleotides of which the ribose moiety is modified with an extra bridge connecting the 2' oxygen and 4' carbon. The locked ribose significantly increases the binding affinity and specificity; and WO2008/147824, which describes modified RNA nucleotides termed UNA (unlocked nucleic acid). UNA are acyclic analogues of RNA in which the bond between the C2" and C3' atoms has been cleaved, decreasing binding affinity towards a complementary strand. UNA are compatible with RNase H recognition and RNA cleavage and improves siRNA mediated gene silencing; WO2008/036127 which describes Morpholino nucleic acid analogues, which contain both uncharged and cationic intersubunit linkages; WO/2007/069092 and EP2075342 which describe Zip Nucleic Acids (ZNA), containing conjugating spermine derivatives as cationic moieties (Z units) to an oligonucleotide; U.S. Pat. No. 5,708,154, which describes RNA linked to a DNA to form a DNA-RNA hybrid; U.S. Pat. No. 5,728,525, which describes the labeling of nucleoside analogs with a universal fluorescent label.

Additional teachings for nucleoside analogs and nucleic acid analogs are U.S. Pat. No. 5,728,525, which describes nucleoside analogs that are end-labeled; U.S. Pat. Nos. 5,637,683, 6,251,666 (L-nucleotide substitutions), and U.S. Pat. No. 5,480,980 (7-deaza-2'-deoxyguanosine nucleotides and nucleic acid analogs thereof).

The use of other analogs is specifically contemplated for use in the context of the present invention. Such analogs may be used in synthetic nucleic acid molecules of the invention, both throughout the molecule or at selected nucleotides. They include, but are not limited to, 1) ribose modifications (such as 2'F, 2' $NH_2$, 2'N3,4'thio, or 2' O—$CH_3$) and 2) phosphate modifications (such as those found in phosphorothioates, methyl phosphonates, and phosphoroborates).

Such analogs have been created to confer stability on RNAs by reducing or eliminating their capacity to be cleaved by ribonucleases. When these nucleotide analogs are present in RNAs, they can have profoundly positive effects on the stability of the RNAs in animals. It is contemplated that the use of nucleotide analogs can be used alone or in conjunction with any of the design modifications of a synthetic miRNA for any nucleic acid of the invention.

Modified Nucleotides miRNAs of the invention specifically contemplate the use of nucleotides that are modified to enhance their activities. Such nucleotides include those that are at the 5' or 3' terminus of the RNA as well as those that are internal within the molecule. Modified nucleotides used in the complementary strands of said miRNAs either block the 5' OH or phosphate of the RNA or introduce internal sugar modifications that enhance uptake of the active strand of the miRNA. Modifications for the miRNAs include internal sugar modifications that enhance hybridization as well as stabilize the molecules in cells and terminal modifications that further stabilize the nucleic acids in cells. Further contemplated are modifications that can be detected by microscopy or other methods to identify cells that contain the synthetic miRNAs.

Preparation of Nucleic Acids

A nucleic acid may be made by any technique known to one of ordinary skill in the art, such as for example, chemical synthesis, enzymatic production or biological production.

Though miRNAs according to the invention could be produced using recombinant methods, it is preferred to produce miRNAs by chemical synthesis or enzymatic production. miRNAs can be produced by a number of methods, including methods involving recombinant DNA technology.

Nucleic acid synthesis is performed according to standard methods. See, for example, Itakura and Riggs (1980). Additionally, U.S. Pat. No. 4,704,362, U.S. Pat. No. 5,221,619, and U.S. Pat. No. 5,583,013 each describe various methods of preparing nucleic acids. Non-limiting examples of a nucleic acid (e.g., a oligonucleotide), include a nucleic acid made by in vitro chemically synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of an oligonucleotide described in U.S. Pat. No. 5,645,897, incorporated herein by reference.

Oligonucleotide synthesis is well known to those of skill in the art. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

Basically, chemical synthesis can be achieved by the diester method, the triester method polynucleotides phosphorylase method and by solid-phase chemistry. These methods are discussed in further detail below.

Diester Method

The diester method was the first to be developed to a usable state, primarily by Khorana and co-workers. (Khorana, 1979). The basic step is the joining of two suitably protected deoxynucleotides to form a dideoxynucleotide containing a phosphodiester bond. The diester method is well established and has been used to synthesize DNA molecules (Khorana, 1979).

Triester Method

The main difference between the diester and triester methods is the presence in the latter of an extra protecting group on the phosphate atoms of the reactants and products (Itakura et al., 1975). The phosphate protecting group is usually a chlorophenyl group, which renders the nucleotides and polynucleotide intermediates soluble in organic solvents. Therefore purifications are done in chloroform solutions. Other improvements in the method include (i) the block coupling of trimers and larger oligomers, (ii) the extensive use of high-performance liquid chromatography for the purification of both intermediate and final products, and (iii) solid-phase synthesis.

Polynucleotide Phosphorylase Method.

This is an enzymatic method of DNA synthesis that can be used to synthesize many useful oligonucleotides (Gillam et al., 1978; Gillam et al, 1979). Under controlled conditions, polynucleotide phosphorylase adds predominantly a single nucleotide to a short oligonucleotide.

Chromatographic purification allows the desired single adduct to be obtained. At least a trimer is required to start the procedure, and this primer must be obtained by some other method. The polynucleotide phosphorylase method works and has the advantage that the procedures involved are familiar to most biochemists.

Solid-Phase Methods.

Drawing on the technology developed for the solid-phase synthesis of polypeptides, it has been possible to attach the initial nucleotide to solid support material and proceed with the stepwise addition of nucleotides. All mixing and washing steps are simplified, and the procedure becomes amenable to automation. These syntheses are now routinely carried out using automatic nucleic acid synthesizers.

Phosphoramidite chemistry (Beaucage and Lyer, 1992) has become by far the most widely used coupling chemistry for the synthesis of oligonucleotides. As is well known to those skilled in the art, phosphoramidite synthesis of oligonucleotides involves activation of nucleoside phosphoramidite monomer precursors by reaction with an activating agent to form activated intermediates, followed by sequential addition of the activated intermediates to the growing oligonucleotide chain (generally anchored at one end to a suitable solid support) to form the oligonucleotide product.

Recombinant Methods.

Recombinant methods for producing nucleic acids in a cell are well known to those of skill in the art. These include the use of vectors, plasmids, cosmids, and other vehicles for delivery a nucleic acid to a cell, which may be the target cell or simply a host cell (to produce large quantities of the desired RNA molecule). Alternatively, such vehicles can be used in the context of a cell free system so long as the reagents for generating the RNA molecule are present. Such methods include those described in Sambrook, 2003, Sambrook, 2001 and Sambrook, 1989, which are hereby incorporated by reference. In certain embodiments, the present invention concerns nucleic acid molecules that are not synthetic. In some embodiments, the nucleic acid molecule has a chemical structure of a naturally occurring nucleic acid and a sequence of a naturally occurring nucleic acid, such as the exact and entire sequence of a single stranded primary miRNA (see Lee 2002), a single-stranded precursor miRNA, or a single-stranded mature miRNA. In addition to the use of recombinant technology, such non-synthetic nucleic acids may be generated chemically, such as by employing technology used for creating oligonucleotides.

Design of miRNAs miRNAs typically comprise two strands, an active strand that is identical in sequence to the mature miRNA that is being studied and a complementary strand that is at least partially complementary to the active strand. The active strand is the biologically relevant molecule and should be preferentially taken up by the complex in cells that modulates translation either through mRNA degradation or translational control. Preferential uptake of the active strand has two profound results: (1) the observed activity of said miRNA increases dramatically and (2) non-intended effects induced by uptake and activation of the complementary strand are essentially eliminated. According to the invention, several miRNA designs can be used to ensure the preferential uptake of the active strand.

5' Blocking Agent.

The introduction of a stable moiety other than phosphate or hydroxyl at the 5' end of the complementary strand impairs its activity in the miRNA pathway. This ensures that only the active strand of the miRNA will be used to regulate translation in the cell. 5' modifications include, but are not limited to, $NH_2$, biotin, an amine group, a lower alkylamine group, an acetyl group, 2' O-Me, DMTO, fluoroscein, a thiol, or acridine or any other group with this type of functionality.

Other sense strand modifications. The introduction of nucleotide modifications like 2'-O Me, 2'-deoxy, T-deoxy-2'-fluoro, 2'-O-methyl, 2'-O-methoxyethyl (2'-0-MOE), 2'-O-aminopropyl (2'-0-AP), 2'-O-dimethylaminoethyl (2'-0-DMAOE), 2'-O-dimethylaminopropyl (2'-0-DMAP), 2'-O-dimethylaminoethyloxyethyl (2'-0-DMAEOE), or 2'-O—N-methylacetamido (2'-0-NMA), $NH_2$, biotin, an amine group, a lower alkylamine group, an acetyl group, DMTO, fluoroscein, a thiol, or acridine or any other group with this type of functionality in the complementary strand of the miRNA can eliminate the activity of the complementary strand and enhance uptake of the active strand of the miRNA.

Base mismatches in the sense strand. As with siRNAs (Schwarz 2003), the relative stability of the 5' and 3' ends of the active strand of the miRNA apparently determines the uptake and activation of the active by the miRNA pathway. Destabilizing the 5' end of the active strand of the miRNA by the strategic placement of base mismatches in the 3' end of the complementary strand of the synthetic miRNA enhances the activity of the active strand and essentially eliminates the activity of the complementary strand.

Host Cells and Target Cells

The cells wherein a miRNA or source thereof is introduced or wherein the presence of a miRNA is assessed may be derived from or contained in any organism. Preferably, the cell is a vertebrate cell. More preferably, the cell is a mammalian cell. Even more preferably, the cell is a human cell.

A mammalian cell may be from the germ line or somatic, totipotent or pluripotent, dividing or non-dividing, epithelium, immortalized or transformed, or the like. The cell may be an undifferentiated cell, such as a stem cell, or a differentiated cell, such as from a cell of an organ or tissue. Alternatively, cells may be qualified as epithelial cells, brain, breast, cervix, colon, gastrointestinal tract, heart, kidney, large intestine, liver, lung, ovary, pancreas, heart, prostate, bladder, small intestine, stomach, testes or uterus.

As used herein, the terms "cell," "cell line," and "cell culture" may be used interchangeably. All of these terms also include their progeny, which is any and all subsequent generations formed by cell division. It is understood that all progeny may not be identical due to deliberate or inadvertent mutations. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a small, interfering RNA or a template construct encoding a reporter gene has been introduced. Therefore, recombinant cells are distinguishable from naturally occurring cells that do not contain a recombinantly introduced nucleic acid.

A tissue may comprise a host cell or cells to be transformed or contacted with a nucleic acid delivery composition and/or an additional agent. The tissue may be part or separated from an organism. In certain embodiments, a tissue and its constituent cells may comprise, but is not limited to brain, stem cells, liver, lung, bone, breast, cervix, colon, endometrium, epithelial, esophagus, goblet cells, kidney, ovaries, pancreas, prostate, bladder, skin, small intestine, stomach, testes, heart, blood vessel.

In certain embodiments, the host cell or tissue may be comprised in at least one organism. In certain embodiments, the organism may be a mammal, a human, a primate or murine. One of skill in the art would further understand the conditions under which to incubate all of the above described host cells to maintain them and to permit their division to form progeny.

Delivery Methods

The present invention involves in some embodiments delivering a nucleic acid into a cell. This may be done as part of a screening method, or it may be related to a therapeutic or diagnostic application.

RNA molecules may be encoded by a nucleic acid molecule comprised in a vector. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, lentivirus, and plant viruses), and artificial chromosomes (e.g., YACs). One of skill in the art would be well equipped to construct a vector through standard recombinant techniques, which are described in Sambrook et al, 1989 and Ausubel et al, 1996, both incorporated herein by reference. In addition to encoding a modified polypeptide such as modified gelonin, a vector may encode non-modified polypeptide sequences such as a tag or targetting molecule. A targetting molecule is one that directs the desired nucleic acid to a particular organ, tissue, cell, or other location in a subject's body.

The term "expression vector" refers to a vector containing a nucleic acid sequence coding for at least part of a gene product capable of being transcribed. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described There are a number of ways in which expression vectors may be introduced into cells. In certain embodiments of the invention, the expression vector comprises a virus or engineered vector derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein, 1988; Temin, 1986). The expression vectors may contain an RNAi expression cassette comprising one promoter and one or more stem-loop structures separated by one or more spacer regions (WO2006/084209).

Another way of introducing expression vectors into cells, using avidin fusion proteins is described in U.S. Pat. No. 6,287,792.

The retroviruses are a group of single-stranded RNA viruses characterized by an ability to convert their RNA to double-stranded DNA in infected cells; they can also be used as vectors. Other viral vectors may be employed as expression constructs in the present invention. Vectors derived from viruses such as vaccinia virus (Ridgeway, 1988; Baichwal and Sugden, 1986; Coupar et al, 1988) adeno-associated virus (AAV) (Ridgeway, 1988; Baichwal and Sugden, 1986; Hermonat and Muzycska, 1984), lentivirus (WO2008/071959, WO2004/054512), Hemaglutinating Virus of Japan (WO2004/035779), Baculovirus (WO2006/048662) and herpesviruses may be employed. They offer several attractive features for various mammalian cells (Friedmann, 1989; Ridgeway, 1988; Baichwal and Sugden, 1986; Coupar et al, 1988; Horwich et al, 1990).

Other suitable methods for nucleic acid delivery to affect expression of compositions of the present invention are believed to include virtually any method by which a nucleic acid (e.g., DNA, including viral and nonviral vectors) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al, 1987); by liposome mediated transfection (Nicolau and Sene, 1982; Fraley et al., 1979; Nicolau et al, 1987; Wong et al, 1980; Kaneda et al., 1989; Kato et al., 1991); by photochemical internalization (WO2008/007073); by microprojectile bombardment (PCT Application Nos. WO 94/09699 and 95/06128; U.S. Pat. Nos. 5,610,042; 5,322,783, 5,563,055, 5,550,318, 5,538,877 and 5,538,880, and each incorporated herein by reference); by agitation with silicon carbide fibers (Kaeppler et al, 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

A review provides several ways of formulating a RNA molecule in order to optimize its internalisation into a cell (Kim S S., et al, Trends Mol. Med., 2009, 15: 491-500). The following other publications discloses alternative ways of formulating a RNA molecule in order to improve its internalisation into a cell, each incorporated herein by reference: WO 2007/095152, describing the use of PTD-DRBD (Peptide transduction domains linked to double stranded binding domain) for delivery of oligonculeotides, WO 2009/086558, describing the use of SNALP (Stable Nucleic Acid Lipid Particles) particles, comprising a mixture of cationic and fusogenic lipids that enable the cellular uptake and endosomal release of the particle's nucleic acid payload, WO 2009/149418, describing neutral phospholipid-oil-RNAi emulsions, WO 2007/121947, describing the use of a delivery vehicle based on lipoplex, WO 2009/132131, describing the use of novel lipids and nucleic acid-lipid particles that provide efficient encapsulation and efficient delivery of the encapsulated nucleic acid to cells, WO2004/091578 and WO2004/064805 describing cochleate technology of alternating layers of lipids that spiral around a nucleic acid molecule, WO2003/047494 and WO2003/047493 describing reverse micelles incorporating nucleic acids for oral and mucosal delivery, WO 2008/156702, describing bacteria and bacterial therapeutic particle (BTP), including oligonucleotides for as delivery vehicle to cells. Each of the formulations referred to or disclosed in these publications is encompassed by the present invention.

A variety of compounds have been attached to the ends of oligonucleotides to facilitate their transport across cell membranes. Short signal peptides found in the HIV TAT, HSV VP22, *Drosphila antennapedia*, and other proteins have been found to enable the rapid transfer of biomolecules across membranes (reviewed by Schwarze 2000). These signal peptides, referred to as Protein Transduction Domains (PTDs), have been attached to oligonucleotides to facilitate their delivery into cultured cells (Eguchi A, Dowdy S F, Trends Pharmacol Sci., 2009, 7:341-5). Cholesterols have been conjugated to oligonucleotides to improve their uptake into cells in animals (MacKellar 1992). The terminal cholesterol groups apparently interact with receptors or lipids on the surfaces of cells and facilitate the internalization of the modified oligonucleotides. Likewise, poly-L-lysine has been conjugated to oligonucleotides to decrease the net negative charge and improve uptake into cells (Leonetti 1990).

A variety of compounds have been developed that complex with nucleic acids, deliver them to surfaces of cells, and facilitate their uptake in and release from endosomes. Among these are: (1) a variety of lipids such as DOTAP (or other cationic lipid), DDAB, DHDEAB, and DOPE and (2) non-lipid-based polymers like polyethylenimine, polyamidoamine, and dendrimers of these and other polymers. In certain of these embodiments a combination of lipids is employed such as DOTAP and cholesterol or a cholesterol derivative (U.S. Pat. No. 6,770,291, which is hereby incorporated by reference). Several of these reagents have been shown to facilitate nucleic acid uptake in animals.

The cellular components involved in the miRNA pathway are becoming known. Proteins that stabilize and/or transport miRNAs within cells might enhance the stability and activity of miRNAs because they should protect and guide the bound miRNAs once they are in cells. Mixtures of miRNA-transporter proteins and miRNAs could enhance the efficacy of miRNA-based therapeutics. RNAs are hydrophilic molecules by virtue of their anionic phosphate and sugar backbone. Although the nucleobases are hydrophobic, hydrophilicity dominates owing to the extensive hydrogen bonding resulting from the phosphate and sugar residues. The hydrophilic character and anionic backbone reduces cellular permeation. Conjugation of lipophilic groups like cholesterol (Manoharan, 2002) and lauric and lithocholic acid derivatives with C32 functionality (Lorenz et al, 2004), have been shown to improve cellular uptake. Moreover binding of steroid conjugated oligonucleotides to different lipoproteins in the bloodstream, such as LDL, protect their integrity and govern their biodistribution (Rump et al, 2000). Cholesterol attached to anti-sense molecules (Bijsterbosch et al., 2001) and aptamers (Rusconi et al., 2004) has also been shown to stabilize oligonucleotides by allowing binding to lipoproteins. Cholesterol has been demonstrated to enhance uptake and serum stability of siRNAs in vitro (Lorenz et al., 2004) and in vivo (Soutschek et al., 2004). Additionally, a number of small molecules like SB-435495 (Blackie et al, (2002), Isradipine (Oravcova et al, 1994), amlodipine (Oravcova et al, 1994) and 2,2',4,4', 5,5'-hexachlorobiphenyl (Borlakoglu et al, 1990) could enhance cellular uptake, and improve nuclease resistance by promoting lipoprotein association.

Screening with miRNA Libraries

As used in the patent application, screening is a process wherein multiple miRNA-specific reagents are delivered separately into individual cell populations or animals. At one or more designated times after delivery, the cell populations or animals are assayed for one or more phenotypes. Those cells or animals that have a significantly different phenotype than cells or animals in the negative control group are classified as positives. The miRNA that was being manipulated in the sample is defined as a hit. Hits represent targets for additional research and potential therapeutic development.

In some embodiments, there is a multi-step process for screening, in certain embodiments, there are four general steps:

(1) Develop Quantitative Assay to Monitor Cellular Process being Studied.

Assays that measure the intensity of a cellular phenotype range from microscopic assays that monitor cell size, cell cycle status, or antibody staining to enzymatic assays that assess the turnover of a specific substrate in a cell lysate to direct measurements of biomolecules or small molecules in lysates, on cells, or in medium.

Critical to the success of a screen is creating an assay that truly measures the cellular phenotype and maximizing the signal-to-noise ratio of the assay. Maximizing signal-to-noise involves testing variables like assay time, assay components, cell type, and length of time between transfection and assay. The greater the difference in the assay results between a positive phenotype and a negative control phenotype, the greater the spread will be in the screening results and the better the opportunity will be to identify interesting genes.

(2) Optimize Transfection Conditions for the Desired Cells.

The first step in this process is identifying a transfection reagent and plating conditions that maximize the uptake of synthetic miRNAs while maintaining high cell viability. We find it useful to test 2-5 different transfection reagents when using cell lines or 5-10 electroporation conditions when using primary or suspension cells. Transfection can be optimized for the reagent or electroporation condition that worked best among the conditions tested. Screening miRNA-specific libraries requires conditions for high-throughput transfection. In this type of screen, lentiviral introduction rather than transfection was used. This may require alternative optimization techniques.

(3) Screen

Once the assay and transfection process have been developed, a library of synthetic miRNAs or miRNAs expressed by viruses can be introduced sequentially into cells in a 24- or 96-well plate. Duplicate or triplicate transfections for each reagent provide enough data for reasonable statistical analysis.

(4) Validate Hits

Validating a hit involves showing that the observed phenotype is due to the miRNA being targeted. Hits are typically confirmed by delivering a dilution series of the miRNA inhibitor or synthetic miRNA that registered as a hit into the cell that was originally assayed. Confirmation is slightly different from validation. Confirmation is a repeat of the miRNA-induced phenotype, whereas validation can also include reversal of the phenotype by antagonizing miRNA mediated phenotype.

Labeling and Labeling Techniques

In some embodiments, the present invention concerns miRNAs that are labeled, such as for screening assays to evaluate the therapeutic or diagnostic relevance of a particular miRNA species. It is contemplated that miRNA may first be isolated (either from a cell in which the miRNA is endogenous to the cell or from a cell in which miRNA is exogenous to the cell) and/or purified prior to labeling. This may achieve a reaction that more efficiently labels the miRNA, as opposed to other RNA in a sample in which the miRNA is not isolated or purified prior to labeling. In many embodiments of the invention, the label is non-radioactive. Generally, nucleic acids may be labeled by adding labeled nucleotides (one-step process) or adding nucleotides and labeling the added nucleotides (two-step process).

Moreover, miRNAs may be labeled as is described in U.S. Patent Application Ser. No. 60/649,584, which is hereby incorporated by reference. Such nucleotides include those that can be labeled with a dye, including a fluorescent dye, or with a molecule such as biotin. Labeled nucleotides are readily available; they can be acquired commercially or they can be synthesized by reactions known to those of skill in the art.

Nucleotides for Labeling

Nucleotides for labelling are not naturally occurring nucleotides, but instead, refer to prepared nucleotides that have a reactive moiety on them. Specific reactive functionalities of interest include: amino, sulfhydryl, sulfoxyl, aminosulfhydryl, azido, epoxide, isothiocyanate, isocyanate, anhydride, monochlorotriazine, dichlorotriazine, mono- or dihalogen substituted pyridine, mono- or disubstituted diazine, maleimide, epoxide, aziridine, sulfonyl halide, acid halide, alkyl halide, aryl halide, alkylsulfonate, N-hydroxysuccinimide ester, imido ester, hydrazine, azidonitrophenyl, azide, 3-(2-pyridyl dithio)-propionamide, glyoxal, aldehyde, iodoacetyl, cyanomethyl ester, p-nitrophenyl ester, o-nitrophenyl ester, hydroxypyridine ester, carbonyl imidazole, and the other such chemical groups. In some embodiments, the reactive functionality may be bonded directly to a nucleotide, or it may be bonded to the nucleotide through a linking group. The functional moiety and any linker cannot substantially impair the ability of the nucleotide to be added to the miRNA or to be labeled. Representative linking groups include carbon containing linking groups, typically ranging from about 2 to 18, usually from about 2 to 8 carbon atoms, where the carbon containing linking groups may or may not include one or more heteroatoms, e.g. S, O, N etc., and may or may not include one or more sites of unsaturation. Of particular interest in many embodiments are alkyl linking groups, typically lower alkyl linking groups of 1 to 16, usually 1 to 4 carbon atoms, where the linking groups may include one or more sites of unsaturation. The functionalized nucleotides (or primers) used in the above methods of functionalized target generation may be fabricated using known protocols or purchased from commercial vendors, e.g., Sigma, Roche, Ambion, and IDT. Functional groups may be prepared according to ways known to those of skill in the art, including the representative information found in U.S. Pat. Nos. 4,404,289; 4,405,711; 4,337,063 and 5,268,486, and Br. Pat. No. 1,529,202, which are all incorporated by reference.

Amine-modified nucleotides are used in several embodiments of the invention. The amine-modified nucleotide is a nucleotide that has a reactive amine group for attachment of the label. It is contemplated that any ribonucleotide (G, A, U, or C) or deoxyribonucleotide (G, A, T, or C) can be modified for labeling. Examples include, but are not limited to, the following modified ribo- and deoxyribo-nucleotides: 5-(3-aminoallyl)-UTP; 8-[(4-amino)butyl]-amino-ATP and 8-[(6-amino)butyl]-amino-ATP; $N^6$-(4-amino)butyl-ATP, $N^6$-(6-amino)butyl-ATP, $N^4$-[2,2-oxy-bis-(ethylamine)]-CTP; $N^6$-(6-Amino)hexyl-ATP; 8-[(6-Amino)hexyl]-amino-ATP; 5-propargylamino-CTP, 5-propargylamino-UTP; 5-(3-aminoallyl)-dUTP; 8-[(4-amino)butyl]-amino-dATP and 8-[(6-amino)butyl]-amino-dATP; N-(4-amino)butyl-dATP, $N^6$-(6-amino)butyl-dATP, $N^4$-[2,2-oxy-to-(ethylamine)]-dCTP; $N^6$-(6-Amino)hexyl-dATP; 8-[(6-Amino)hexyl]-amino-dATP; 5-propargylamino-dCTP, and 5-propargylamino-dUTP. Such nucleotides can be prepared according to methods known to those of skill in the art. Moreover, a person of ordinary skill in the art could prepare other nucleotide entities with the same amine-modification, such as a 5-(3-aminoallyl)-CTP, GTP, ATP, dCTP, dGTP, dTTP, or dUTP in place of a 5-(3-aminoallyl)-UTP.

Labeling Techniques

In some embodiments, nucleic acids are labeled by catalytically adding to the nucleic acid an already labeled nucleotide or nucleotides. One or more labeled nucleotides can be added to miRNA molecules. See U.S. Pat. No. 6,723,509, which is hereby incorporated by reference.

In other embodiments, an unlabeled nucleotide or nucleotides is catalytically added to an miRNA, and the unlabeled nucleotide is modified with a chemical moiety that enables it to be subsequently labeled, in embodiments of the invention, the chemical moiety is a reactive amine such that the nucleotide is an amine-modified nucleotide. Examples of amine-modified nucleotides are well known to those of skill in the art, many being commercially available such as from Ambion, Sigma, Jena Bioscience, and TriLink.

In contrast to labeling of cDNA during its synthesis, the issue for labeling miRNAs is how to label the already existing molecule. To this end, we may use an enzyme capable of using a di- or tri-phosphate ribonucleotide or deoxyribonucleotide as a substrate for its addition to an miRNA, a small RNA molecule. Moreover, in specific embodiments, it involves using a modified di- or triphosphate ribonucleotide, which is added to the 3' end of an miRNA. The source of the enzyme is not limiting. Examples of sources for the enzymes include yeast, gram-negative bacteria such as *E. coli*, lactococcus lactis, and sheep pox virus.

Enzymes capable of adding such nucleotides include, but are not limited to, poly(A) polymerase, terminal transferase, and polynucleotide phosphorylase. In specific embodiments of the invention, ligase is contemplated as NOT being the enzyme used to add the label, and instead, a non-ligase enzyme is employed.

Poly(A) polymerase has been cloned from a number of organisms from plants to humans. It has been shown to catalyze the addition of homopolymer tracts to RNA (Martin et al, RNA, 4(2):226-30, 1998).

Terminal transferase catalyzes the addition of nucleotides to the 3' terminus of a nucleic acid.

Polynucleotide phosphorylase can polymerize nucleotide diphosphates without the need for a primer.

Labels and Tags miRNAs or miRNA probes may be labeled with a positron emitting (including radioactive), enzymatic, colorimetric (includes visible and UV spectrum, including fluorescent), luminescent or other label or tag for detection or isolation purposes. The label may be detected directly or indirectly. Radioactive labels include $^{125}I$, $^{32}P$, $^{33}P$, and $^{35}S$. Examples of enzymatic labels include alkaline phosphatase, luciferase, horseradish peroxidase, and β-galactosidase. Labels can also be proteins with luminescent properties, e.g., green fluorescent protein and phicoerythrin.

The colorimetric and fluorescent labels contemplated for use as conjugates include, but are not limited to, AMCA, Alexa Fluor dyes, BODIPY dyes, such as BODIPY FL, BODIPY 630/650, BODIPY 650/665, BODIP Y-R6G, BODIPY-TRX; Cascade Blue; Cascade Yellow; coumarin and its derivatives, such as 7-amino-4-methylcoumarin, aminocoumarin and hydroxycoumarin; cyanine dyes, such as Cy3 and Cy5; eosins and erythrosins; fluorescein and its derivatives, such as fluorescein isothiocyanate; macrocyclic chelates of lanthanide ions, such as Quantum Dye™; Marina Blue; Oregon Green; rhodamine dyes, such as rhodamine red, tetramethylrhodamine and rhodamine 6G; Texas Red;

Specific examples of dyes include, but are not limited to, those identified above and the following: Alexa Fluor 350, Alexa Fluor 405, Alexa Fluor 430, Alexa Fluor 488, Alexa Fluor 500. Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, and, Alexa Fluor 750; amine-reactive BODIPY dyes, such as BODIPY 493/503, BODEPY 530/550, BODEPY 558/568, BODIPY 564/570, BODDPY 576/589, BODIPY 581/591, BODEPY 630/650, BODIPY 650/655, BODIPY FL, BODIPY R6G, BODEPY TMR, and, BODIPY-TR; Cy3, Cy5, 6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, 2',4',5',7'-Tetrabromosulfonefluorescein, and TET.

Specific examples of fluorescently labeled ribonucleotides are available from Molecular Probes, and these include, Alexa Fluor 488-5-UTP, Fluorescein-12-UTP, BODEPY FL-14-UTP, BODIPY TMR-14-UTP, Tetramethylrhodamine-6-UTP, Alexa Fluor 546-14-UTP, Texas Red-5-UTP, and BODIPY TR-14-UTP. Other fluorescent ribonucleotides are available from Amersham Biosciences, such as Cy3-UTP and Cy5-UTP. Examples of fluorescently labeled deoxyribonucleotides include Dinitrophenyl (DNP)-11-dUTP, Cascade Blue-7-dUTP, Alexa Fluor 488-5-dUTP, Fluorescein-12-dUTP, Oregon Green 488-5-dUTP, BODEPY FL-14-dUTP, Rhodamine Green-5-dUTP, Alexa Fluor 532-5-dUTP, BODEPY TMR-14-dUTP, Tetramethylrhodamine-6-dUTP, Alexa Fluor 546-14-dUTP, Alexa Fluor 568-5-dUTP, Texas Red-12-dUTP, Texas Red-5-dUTP, BODEPY TR-14-dUTP, Alexa Fluor 594-5-dUTP, BODEPY 630/650-14-dUTP, BODIPY 650/665-14-dUTP; Alexa Fluor 488-7-OBEA-dCTP, Alexa Fluor 546-16-OBEA-dCTP, Alexa Fluor 594-7-OBEA-dCTP, Alexa Fluor 647-12-OBEA-dCTP. It is contemplated that nucleic acids may be labeled with two different labels.

It is contemplated that synthetic miRNAs may be labeled with more than one label, or with two different labels. Furthermore, fluorescence resonance energy transfer (FRET) may be employed in methods of the invention (e.g., Klostermeier et al., 2002; Emptage, 2001; Didenko, 2001, each incorporated by reference). Fluorescent energy transfer dyes, such as thiazole orange-ethidium heterodimer; and, TOTAB may be used. Alternatively, the label may not be detectable per se, but indirectly detectable or allowing for the isolation or separation of the targeted nucleic acid. For example, the label could be biotin, digoxigenin, polyvalent cations, chelator groups and the other ligands, include ligands for an antibody.

Visualization Techniques

A number of techniques for visualizing or detecting labeled nucleic acids are readily available. The reference by Stanley T. Crooke, 2000 has a discussion of such techniques (Chapter 6), which is incorporated by reference. Such techniques include, microscopy, arrays, Fluorometry, Light cyclers or other real time PCR™ machines, FACS analysis, scintillation counters, Phosphoimagers, Geiger counters, MRI, CAT, antibody-based detection methods (Westerns, immunofluorescence, immunohistochemistry), histochemical techniques, HPLC (Griffey et al, 1997, spectroscopy, capillary gel electrophoresis (Cummins et ah, 1996), spectroscopy; mass spectroscopy; radiological techniques; and mass balance techniques. Alternatively, nucleic acids may be labeled or tagged to allow for their efficient isolation. In other embodiments of the invention, nucleic acids are biotinylated.

When two or more differentially colored labels are employed, fluorescent resonance energy transfer (FRET) techniques may be employed to characterize the dsRNA. Furthermore, a person of ordinary skill in the art is well aware of ways of visualizing, identifying, and characterizing labeled nucleic acids, and accordingly, such protocols may be used as part of the invention. Examples of tools that may be used also include fluorescent microscopy, a BioAnalyzer, a plate reader, Storm (Molecular Dynamics), Array Scanner, FACS (fluorescent activated cell sorter), or any instrument that has the ability to excite and detect a fluorescent molecule.

Array Preparation

The present invention can be employed with miRNA arrays, which are ordered macroarrays or microarrays of nucleic acid molecules (probes) that are fully or nearly complementary or identical to a plurality of miRNA molecules or precursor miRNA molecules and that are positioned on a support material in a spatially separated organization. Macroarrays are typically sheets of nitrocellulose or nylon upon which probes have been spotted. Microarrays position the nucleic acid probes more densely such that up to 10,000 nucleic acid molecules can be fit into a region typically 1 to 4 square centimeters. Microarrays can be fabricated by spotting nucleic acid molecules, e.g., genes, oligonucleotides, etc., onto substrates or fabricating oligonucleotide sequences in situ on a substrate. Spotted or fabricated nucleic acid molecules can be applied in a high density matrix pattern of up to about 30 non-identical nucleic acid molecules per square centimeter or higher, e.g. up to about 100 or even 1000 per square centimeter. Microarrays typically use coated glass as the solid support, in contrast to the nitrocellulose-based material of filter arrays. By having an ordered array of miRNA-complementing nucleic acid samples, the position of each sample can be tracked and linked to the original sample. A variety of different array devices in which a plurality of distinct nucleic acid probes are stably associated with the surface of a solid support are known to those of skill in the art. Useful substrates for arrays include nylon, glass and silicon Such arrays may vary in a number of different ways, including average probe length, sequence or types of probes, nature of bond between the probe and the array surface, e.g. covalent or non-covalent, and the like.

Representative methods and apparatus for preparing a microarray have been described, for example, in U.S. Pat. Nos. 5,143,854; 5,202,231; 5,242,974; 5,288,644; 5,324,633; 5,384,261; 5,405,783; 5,412,087; 5,424,186; 5,429,807; 5,432,049; 5,436,327; 5,445,934; 5,468,613; 5,470,710; 5,472,672; 806; U.S. Pat. Nos. 5,525,464; 5,503,980; 5,510, 270; 5,525,464; 5,527,681; 5,529,756; 5,532,128; 5,545,531; 5,547,839; 5,554,501; 5,556,752; 5,561,071; 5,571,639; 5,580,726; 5,580,732; 5,593,839; 5,599,695; 5,599,672; 5,610,287; 5,624,711; 5,631,134; 5,639,603; 5,654,413; 5,658,734; 5,661,028; 5,665,547; 5,667,972; 5,695,940; 5,700,637; 5,744,305; 5,800,992; 5,807,522; 5,830,645; 5,837,196; 5,871,928; 5,847,219; 5,876,932; 5,919,626; 6,004,755; 6,087,102; 6,368,799; 6,383,749; 6,617,112;

6,638,717; 6,720,138, as well as WO 93/17126; WO 95/11995; WO 95/21265; WO 95/21944; WO 95/35505; WO 96/31622; WO 97/10365; WO 97/27317; WO 99/35505; WO 09923256; WO 09936760; WO0138580; WO 0168255; WO 03020898; WO 03040410; WO 03053586; WO 03087297; WO 03091426; WO03100012; WO 04020085; WO 04027093; EP 373 203; EP 785 280; EP 799 897 and UK 8 803 000; the disclosures of which are all herein incorporated by reference. It is contemplated that the arrays can be high density arrays, such that they contain 100 or more different probes. It is contemplated that they may contain 1000, 16,000, 65,000, 250,000 or 1,000,000 or more different probes. The probes can be directed to targets in one or more different organisms. The oligonucleotide probes range from 5 to 50, 5 to 45, 10 to 40, or 15 to 40 nucleotides in length in some embodiments, hi certain embodiments, the oligonucleotide probes are 20 to 25 nucleotides in length.

The location and sequence of each different probe sequence in the array are generally known. Moreover, the large number of different probes can occupy a relatively small area providing a high density array having a probe density of generally greater than about 60, 100, 600, 1000, 5,000, 10,000, 40,000, 100,000, or 400,000 different oligonucleotide probes per $cm^2$. The surface area of the array can be about or less than about 1, 1.6, 2, 3, 4, 5, 6, 7, 8, 9, or 10 $cm^2$.

Moreover, a person of ordinary skill in the art could readily analyze data generated using an array. Such protocols are disclosed above, and include information found in WO 9743450; WO 03023058; WO 03022421; WO 03029485; WO03067217; WO 03066906; WO 03076928; WO 03093810; WO 03100448A1, all of which are specifically incorporated by reference.

Recently, alternative profiling methods have become available, based on solution hybridization and subsequent immobilization and identification e.g. Illumina platform.

Sample Preparation

It is contemplated that the miRNA of a wide variety of samples can be analyzed using assays described herein. While endogenous miRNA is contemplated for use with some embodiments, recombinant or synthetic miRNA—including nucleic acids that are identical to endogenous miRNA or precursor miRNA—can also be handled and analyzed as described herein. Samples may be biological samples, in which case, they can be from blood, CSF, tissue, organs, tumor, semen, sputum, stool, urine, saliva, tears, other bodily fluid, hair follicles, skin, or any sample containing or constituting biological cells. Alternatively, the sample may not be a biological sample, but be a chemical mixture, such as a cell-free reaction mixture (which may contain one or more biological enzymes).

Cell Assays to Identify miRNAs with Ties to Disease

Specifically contemplated applications include identifying miRNAs that contribute to EMT that are themselves parts of a disease or conditions or might otherwise be associated with a particular disease state. Additionally, a contemplated application includes the identification of miRNAs that are able to revert EMT and induce MET. Also, miRNA functions may be compared between a sample believed to be susceptible to a particular disease or condition associated with EMT and one believed to be not susceptible or resistant to that disease or condition. It is specifically contemplated that RNA molecules of the present invention can be used to treat any of the diseases or conditions discussed in the previous section or modulate any of the cellular pathways discussed in the previous section. Specifically contemplated applications include identifying miRNAs that contribute to EMT cellular processes that are themselves parts of a disease or might otherwise be associated with a particular disease state. Also, miRNA functions may be compared between a sample believed to be susceptible to a particular disease or condition associated with EMT and one believed to be not susceptible or resistant to that disease or condition.

The efficacy of different therapeutic drugs may be altered by miRNAs as defined and used according to the present invention. Moreover, it has been described that tumor cells that have undergone EMT may become resistant to chemo and immunotherapy (Thiery et al. 2009 Cell 139:871-90). Therefore, miRNA based drugs that induce reversal of EMT may enhance susceptibility to e.g. chemo and immunotherapy. Such therapeutic drugs include, but are not limited to, chemotherapeutic drugs. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma and calicheamicin omega); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including morpholmo-doxorubicm, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex; razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-II); topoisomerase inhibitor RFS 2000; difluoromethylornithine (DMFO); retinoids such as retinoic acid; capecitabine; and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY1 17018, onapristone, and toremifene; aromatase inhibitors that inhibit the enzyme aromatase, which regulates estrogen production in the adrenal glands, such as, for example, 4(5)-imidazoles, aminoglutethimide, megestrol acetate, exemestane, formestanie, fadrozole, vorozole, letrozole, and anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in aberrant cell proliferation, such as, for example, PKC-α, Raf and H-Ras; ribozymes such as a VEGF expression inhibitor and a HER2 expression inhibitor; vaccines such as gene therapy vaccines and pharmaceutically acceptable salts, acids or derivatives of any of the above. A list of U.S. FDA approved oncology drugs with their approved indications can be found on the World Wide Web at accessdata.fda.gov/scripts/cder/onctools/druglist.cfm. Moreover, it is contemplated that samples that have differences in the activity of certain pathways may also be compared. Such cellular pathways include but are not limited to the following: any adhesion or motility pathway including but not limited to those involving cyclic AMP, protein kinase A, G-protein couple receptors, adenylyl cyclase, L-selectin, E-selectin, PECAM, VCAM-1, α-actinin, paxillin, cadherins, AKT, integrin-α, integrin-β, RAF-I, ERK, PI-3 kinase, vinculin, matrix metalloproteinases, Rho GTPases, p85, trefoil factors, profilin, FAK, MAP kinase, Ras, caveolin, calpain-1, calpain-2, epidermal growth factor receptor, ICAM-1, ICAM-2, cofilin, actin, gelsolin, Rho A, Rac, myosin light chain kinase, platelet-derived growth factor receptor or ezrin; any apoptosis pathway including but not limited to those involving AKT, Fas ligand, NFKB, caspase-9, PB kinase, caspase-3, caspase-7, ICAD, CAD, EndoG, Granzyme B, Bad, Bax, Bid, Bak, APAF-I, cytochrome C, p53, ATM, Bcl-2, PARP, Chk1, Chk2, Rho-21, c-Jun, Rho73, Rad51, Mdm2, Rad50, c-Abl, BRCA-I, perforin, caspase-4, caspase-8, caspase-6, caspase-1, caspase-2, caspase-10, Rho, Jun kinase, Jun kinase kinase, Rip2, lamin-A, lamin-B1, lamin-B2, Fas receptor, $H_2O_2$, Granzyme A, NADPH oxidase, HMG2, CD4, CD28, CD3, TRADD, IKK, FADD, GADD45, DR3 death receptor, DR4/5 death receptor, FLIPs, APO-3, GRB2, SHC, ERK, MEK, RAF-1, cyclic AMP, protein kinase A, E2F, retinoblastoma protein, Smac/Diablo, ACH receptor, 14-3-3, FAK, SODD, TNF receptor, RTP, cyclin-Dl, PCNA, BcI-XL, PIP2, PIP3, PTEN, ATM, Cdc2, protein kinase C, calcineurin, IKKα, IKKβ, IKKγ, SOS-I, c-FOS, Traf-1, Traf-2, IκBβ or the proteasome; any cell activation pathway including but not limited to those involving protein kinase A, nitric oxide, caveolin-1, actin, calcium, protein kinase C, Cdc2, cyclin B, Cdc25, GRB2, SRC protein kinase, ADP-ribosylation factors (ARFs), phospholipase D, AKAP95, p68, Aurora B, CDK1, Eg7, histone H3, PKAc, CD80, PI3 kinase, WASP, Arp2, Arp3, p34, p20, PP2A, angiotensin, angiotensin-converting enzyme, protease-activated receptor-1, protease-activated receptor-4, Ras, RAF-I, PLCβ, PLCγ, COX-I, G-protein-coupled receptors, phospholipase A2, IP3, SUMO1, SUMO 2/3, ubiquitin, Ran, Ran-GAP, Ran-GEF, p53, glucocorticoids, glucocorticoid receptor, components of the SWI/SNF complex, RanBP1, RanBP2, importins, exportins, RCCl, CD40, CD40 ligand, p38, DCKα, IKKβ, NFKB, TRAF2, TRAF3, TRAF5, TRAF6, IL-4, IL-4 receptor, CDK5, AP-I transcription factor, CD45, CD4, T cell receptors, MAP kinase, nerve growth factor, nerve growth factor receptor, c-Jun, c-Fos, Jun kinase, GRB2, SOS-I, ERK-I, ERK, JAK2, STAT4, IL-12, IL-12 receptor, nitric oxide synthase, TYK2, IFNγ, elastase, IL-8, epithelins, IL-2, IL-2 receptor, CD28, SMAD3, SMAD4, TGFβ or TGFβ receptor; any cell cycle regulation, signaling or differentiation pathway including but not limited to those involving TNFs, SRC protein kinase, Cdc2, cyclin B, Grb2, Sos-1, SHC, p68, Aurora kinases, protein kinase A, protein kinase C, Eg7, p53, cyclins, cyclin-dependent kinases, neural growth factor, epidermal growth factor, retinoblastoma protein, ATF-2, ATM, ATR, AKT, CHK1, CHK2, 14-3-3, WEE1, CDC25 CDC6, Origin Recognition Complex proteins, p15, p16, p27, p21, ABL, c-ABL, SMADs, ubiquitin, SUMO, heat shock proteins, Wnt, GSK-3, angiotensin, p73 any PPAR, TGFα, TGFβ, p300, MDM2, GADD45, Notch, cdc34, BRCA-I, BRCA-2, SKP1, the proteasome, CUL1, E2F, pi 07, steroid hormones, steroid hormone receptors, IκBα, IκBβ, Sin3A, heat shock proteins, Ras, Rho, ERKs, IKKs, PI3 kinase, Bcl-2, Bax, PCNA, MAP kinases, dynein, RhoA, PKAc, cyclin AMP, FAK, PIP2, PIP3, integrins, thrombopoietin, Fas, Fas ligand, PLK3, MEKs, JAKs, STATs, acetylcholine, paxillin calcineurin, p38, importins, exportins, Ran, Rad50, Rad51, DNA polymerase, RNA polymerase, Ran-GAP, Ran-GEF, NuMA, Tpx2, RCCl, Sonic Hedgehog, Crml, Patched (Ptc-1), MPF, CaM kinases, tubulin, actin, kinetochore-associated proteins, centromere-binding proteins, telomerase, TERT, PP2A, c-MYC, insulin, T cell receptors, B cell receptors, CBP, 1 KB, NFKB, RAl, RAFl, EPO, diacylglycerol, c-Jun, c-Fos, Jun kinase, hypoxia-inducible factors, GATA4, β-catenin, α-catenin, calcium, arrestin, survivin, caspases, procaspases, CREB, CREM, cadherins, PECAMs, corticosteroids, colony-stimulating factors, calpains, adenylyl cyclase, growth factors, nitric oxide, transmembrane receptors, retinoids, G-proteins, ion channels, transcriptional activators, transcriptional coactivators, transcriptional repressors, interleukins, vitamins, interferons, transcriptional corepressors, the nuclear pore, nitrogen, toxins, proteolysis, or phosphorylation; or any metabolic pathway including but not limited to those involving the biosynthesis of amino acids, oxidation of fatty acids, biosynthesis of neurotransmitters and other cell signaling molecules, biosynthesis of polyamines, biosynthesis of lipids and sphingolipids, catabolism of amino acids and nutrients, nucleotide synthesis, eicosanoids, electron transport reactions, ER-associated degradation, glycolysis, fibrinolysis, formation of ketone bodies, formation of phagosomes, cholesterol metabolism, regulation of food intake, energy homeostasis, prothrombin activation, synthesis of lactose and other sugars, multi-drug resistance, biosynthesis of phosphatidylcholine, the proteasome, amyloid precursor protein, Rab GTPases, starch synthesis, glycosylation, synthesis of phoshoglycerides, vitamins, the citric acid cycle, IGF-I receptor, the urea cycle, vesicular transport, or salvage pathways. It is further contemplated that nucleic acids molecules of the invention can be employed in diagnostic and therapeutic methods with respect to any of the above pathways or factors. Thus, in some embodiments of the invention, a miRNA inhibits, eliminate, activates, induces, increases, or otherwise modulates one or more of the above pathways or factors is contemplated as part of methods of the invention. The nucleic acid can be used to diagnosis a disease or condition based on the relation of that miRNA to any of the pathways described above.

Other Assays

In addition to the use of arrays and microarrays, it is contemplated that a number of difference assays could be employed to analyze miRNAs, their activities and their effects. Such assays include, but are not limited to, RT-PCR, in situ hybridization, hybridization protection assay (HPA) (GenProbe), branched DNA (bDNA) assay (Collins, M. L. et al. (1997). Nucleic Acids Research 25: 2979-2984), rolling circle amplification (RCA), single molecule hybridization detection (US Genomics), Invader assay (ThirdWave Technologies), and Bridge Litigation Assay (Qiagen). It is contemplated that such methods may be used in the context of arrays, as well as in the context of diagnostic assays.

Therapeutic and Diagnostic Applications miRNAs that affect phenotypic traits provide intervention points for therapeutic applications as well as diagnostic applications (by screening for the presence or absence of a particular miRNA). It is specifically contemplated that RNA molecules of the present invention can be used to treat any of the diseases or conditions discussed in the previous section. Moreover, any of the methods described above can also be employed with respect to therapeutic and diagnostic aspects of the invention. For example, methods with respect to detecting miRNAs or screening for them can also be employed in a diagnostic context. In therapeutic applications, an effective amount of the miRNAs of the present invention is administered to a cell, which may or may not be in an animal. In some embodiments, a therapeutically effective amount of the miRNAs of the present invention is administered to an individual for the treatment of disease or condition. The term "effective amount" as used herein is defined as the amount of the molecules of the present invention that are necessary to result in the desired physiological change in the cell or tissue to which it is administered. The term "therapeutically effective amount" as used herein is defined as the amount of the molecules of the present invention that achieves a desired effect with respect to a disease or condition associated with EMT as earlier defined herein. A skilled artisan readily recognizes that in many cases the molecules may not provide a cure but may provide a partial benefit, such as alleviation or improvement of at least one symptom. In some embodiments, a physiological change having some benefit is also considered therapeutically beneficial. Thus, in some embodiments, an amount of molecules that provides a physiological change is considered an "effective amount" or a "therapeutically effective amount."

In some embodiments a molecule has a sequence that corresponds to the miRNA sequence from that particular animal, as opposed to from another animal. Thus, in some embodiments, a human sequence is utilized as a RNA molecule of the present invention. In in vivo experiments, a miRNA sequence used in a test animal may differ from a corresponding human sequence. In that case, a miRNA that differs from the human sequence might be used to demonstrate therapeutic effect in the animal. Results obtained with this sequence tested in an animal may be extrapolated expected results in human with a corresponding miRNA molecule.

Modes of Administration and Formulations

The nucleic acid molecules of the invention may be administered to a subject alone or in the form of a pharmaceutical composition for the treatment of a condition or disease. Pharmaceutical compositions may be formulated in conventional manner using one or more physiologically acceptable carriers, diluents, excipients or auxiliaries which facilitate processing of the miRNA into preparations which can be used pharmaceutically. Proper formulation is dependent upon the route of administration chosen. For topical administration the miRNAs of the invention may be formulated as solutions, gels, ointments, creams, suspensions, etc. as are well-known in the art. Systemic formulations include those designed for administration by injection, e.g. subcutaneous, intravenous, intramuscular, intrathecal or intraperitoneal injection, as well as those designed for transdermal, transmucosal, inhalation, oral or pulmonary administration. For injection, the nucleic acids of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the nucleic acid molecules may be in powder form for constitution with a suitable vehicle, e.g., sterile pyrogen-free water, before use. For transmucosal administration, penetrants appropriate to the barrier to be permeated are used in the formulation. Such penetrants are generally known in the art. For oral administration, the nucleic acids can be readily formulated by combining the molecules with pharmaceutically acceptable carriers well known in the art. Such carriers enable the nucleic acids of the invention to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, e.g. lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques. For oral liquid preparations such as, for example, suspensions, elixirs and solutions, suitable carriers, excipients or diluents include water, glycols, oils, alcohols, etc. Additionally, flavoring agents, preservatives, coloring agents and the like may be added. For buccal administration, the molecules may take the form of tablets, lozenges, etc. formulated in conventional manner. For administration by inhalation, the molecules for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator may be formulated containing a powder mix of the nucleic acids and a suitable powder base such as lactose or starch. The RNA molecules may also be formulated in rectal or vaginal compositions such as suppositories or retention enemas, e.g., containing conventional suppository bases such as cocoa butter or other glycerides.

In addition to the formulations described previously, the molecules may also be formulated as a depot preparation. Such long acting formulations may be administered by implantation (for example subcutaneously or intramuscularly) or by intramuscular injection. Thus, for example, the molecules may be formulated with suitable polymeric or hydrophobic materials (for example as an emulsion in an acceptable oil) or ion exchange resins, or as sparingly soluble derivatives, for example, as a sparingly soluble salt. Alternatively, other pharmaceutical delivery systems may be employed.

Liposomes and emulsions are well-known examples of delivery vehicles that may be used to deliver nucleic acids of the invention.

A nucleic acid of the invention may be administered in combination with a carrier or lipid to increase cellular uptake. For example, the oligonucleotide may be administered in combination with a cationic lipid. Examples of cationic lipids include, but are not limited to, lipofectin, DOTMA, DOPE, and DOTAP. The publication of WO0071096, which is specifically incorporated by reference, describes different formulations, such as a DOTAP; cholesterol or cholesterol derivative formulation that can effectively be used for gene therapy. Other disclosures also discuss different lipid or liposomal formulations including nanoparticles and methods of administration; these include, but are not limited to, U.S. Patent Publication 20030203865, 20020150626, 20030032615, and 20040048787, which are specifically incorporated by reference to the extent they disclose formulations and other related aspects of administration and delivery of nucleic acids. Methods used for forming particles are also disclosed in U.S. Pat. Nos. 5,844,107, 5,877,302, 6,008,336, 6,077,835, 5,972,901, 6,200,801, and 5,972,900, which are incorporated by reference for those aspects. The nucleic acids may also be administered in combination with a cationic amine such as poly-L-lysine.

Nucleic acids may also be conjugated to a chemical moiety, such as transferrin and cholesteryls. In addition, oligonucleotides may be targeted to certain organs or tissues by linking specific chemical groups to the oligonucleotide. For example, linking the oligonucleotide to a suitable array of mannose residues will target the oligonucleotide to the liver. Other targeting ligands are described in Liu B., Brief Funct. Genomic Proteomic 6:112-119, 2007. Additional examples are carbohydrate sugars such as galactose, N-acetylgalactosamine, mannose; vitamins such as folates small molecules including naproxen, ibuprofen or other known protein-binding molecules, cyclodextrin, which targets the transferrin receptor, also called transferring modified cyclodextrin (Hu-Lieskovan et al., 2005), PEI (RGD-targeted PEG-PEI, Schiffelers et al. 2004), anisamide, RGD-peptide or RGD mimics, poly-arginin, anti-TfR single chain antibody fragment/TfRscFv, Annexin A5 (targeting phophatidylserine exposing membranes, Garnier B. et al., Bioconjug Chem., 2009, 11:2114-22), WO 2009/126933 describing compositions and methods for site-specific delivery of nucleic acids by combining them with targeting ligands and endosomolytic components. Targeting ligands that are preferentially suitable are tumor associated cell surface proteins, more preferably prostate tumor associated cell surface proteins. Targeting of nucleic acids may also be accomplished by using aptamer technology as described in WO2005/111238. Moreover, additional lipid moieties, such as PEG-lipids, cholesterol, endosomolytic helper lipids or peptides (WO2009/046220) or the overall morphology of the generated nanoparticles (characterized by charge and particle size) to the above mentioned delivery vehicles may confer targeting specificity to either cancer cells and/or tumor vasculature.

Additionally, the molecules may be delivered using a sustained-release system, such as semipermeable matrices of solid polymers containing the therapeutic agent. Various of sustained-release materials have been established and are well known by those skilled in the art. Sustained-release capsules may, depending on their chemical nature, release the molecules for a few weeks up to over 100 days. Depending on the chemical nature and the biological stability of the chimeric molecules, additional strategies for molecule stabilization may be employed.

Alternatively, the molecules may be delivered using a coordination chemistry based delivery system as described in WO2007011217, which is specifically incorporated herein by reference.

Nucleic acids may be included in any of the above-described formulations as the free acids or bases or as pharmaceutically acceptable salts. Pharmaceutically acceptable salts are those salts that substantially retain the biological activity of the free bases and which are prepared by reaction with inorganic acids. Pharmaceutical salts tend to be more soluble in aqueous and other protic solvents than are the corresponding free base forms.

Pharmaceutical compositions of the present invention comprise an effective amount of one or more miRNA molecules dissolved or dispersed in a pharmaceutically acceptable carrier. The phrases "pharmaceutical or pharmacologically acceptable" refers to molecular entities and compositions that do not produce or produce acceptable adverse, allergic or other untoward reaction when administered to an animal, such as, for example, a human, as appropriate. Whether certain adverse effects are acceptable is determined based on the severity of the disease. The preparation of an pharmaceutical composition that contains at least one chimeric polypeptide or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The miRNAs may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g. aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to an animal or a patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, or 2% to 75% of the weight of the unit or 25% to 60% for example and any range derivable therein. In other non-limiting examples, a dose may also comprise less than 1 microgram/kg/body weight, or 1 microgram/kg/body weight, from 5 microgram/kg/body weight, 10 microgram/kg/body weight, 50 microgram/kg/body weight, 100 microgram/kg/body weight, 200 microgram/kg/body weight, 350 microgram/kg/body weight, 500 microgram/kg/body weight, 1 milligram/kg/body weight, 5 milligram/kg/body weight, 10 milligram/kg/body weight, 50 milligram/kg/body weight, 100 milligram/kg/body weight, 200 milligram/kg/body weight, 350 milligram/kg/body weight, or 500 milligram/kg/body weight, to 1000 mg/kg/body weight or more per administration, and any range derivable therein. In non-limiting examples of a derivable range from the numbers listed herein, a range of 5 mg/kg/body weight to 100 mg/kg/body weight, 5 microgram/kg/body weight to 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The molecules may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines. In certain embodiments, the molecules are prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. or combinations of the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

Any embodiment discussed above with respect to delivery or transport to cells can also be employed with respect to implementing delivery of medicinal compounds discussed in this section.

Effective Dosages

The molecules of the invention will generally be used in an amount effective to achieve the intended purpose. For use to treat or prevent a disease condition, the molecules of the invention, or pharmaceutical compositions thereof, are administered or applied in a therapeutically effective amount. A therapeutically effective amount is an amount effective to ameliorate or prevent the symptoms, or prolong the survival of the patient being treated. Determination of a therapeutically effective amount is well within the capabilities of those skilled in the art, especially in light of the detailed disclosure provided herein.

For systemic administration, a therapeutically effective dose can be estimated initially from in vitro assays. For example, a dose can be formulated in animal models to achieve a circulating concentration range that includes the EC50 as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the molecules which are sufficient to maintain therapeutic effect. Usual patient dosages for administration by injection range from 0.01 to 0.1 mg/kg/day, or from 0.1 to 5 mg/kg/day, preferably from 0.5 to 1 mg/kg/day or more. Therapeutically effective serum levels may be achieved by administering multiple doses each day.

In cases of local administration or selective uptake, the effective local concentration of the proteins may not be related to plasma concentration. One having skill in the art will be able to optimize therapeutically effective local dosages without undue experimentation.

The amount of molecules administered will, of course, be dependent on the subject being treated, on the subject's weight, the severity of the affliction, the manner of administration and the judgment of the prescribing physician.

The therapy may be repeated intermittently while symptoms detectable or even when they are not detectable. The therapy may be provided alone or in combination with other drugs or treatment (including surgery).

Toxicity

Preferably, a therapeutically effective dose of the molecules described herein will provide therapeutic benefit without causing substantial toxicity. Toxicity of the molecules described herein can be determined by standard pharmaceutical procedures in cell cultures or experimental animals, e.g., by determining the LD50 (the dose lethal to 50% of the population) or the LD100 (the dose lethal to 100% of the population). The dose ratio between toxic and therapeutic effect is the therapeutic index. Proteins which exhibit high therapeutic indices are preferred. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al, 1975, In: The Pharmacological Basis of Therapeutics, Ch. 1, p. 1).

Pendant Groups

A "pendant group" may be attached or conjugated to the nucleic acid. Pendant groups may increase cellular uptake of the nucleic acid. Pendant groups can be linked to any portion of the nucleic acid but are commonly linked to the end(s) of the oligonucleotide chain. Examples of pendant groups include, but are not limited to: acridine derivatives (i.e. 2-methoxy-6-chloro-9-ammoacridine); cross-linkers such as psoralen derivatives, azidophenacyl, proflavin, and azidoproflavin; artificial endonucleases; metal complexes such as EDTA-Fe(II), o-phenanthroline-Cu(I), and porphyrin-Fe (II); alkylating moieties; nucleases such as amino-1-hexanol-staphylococcal nuclease and alkaline phosphatase; terminal transferases; abzymes; cholesteryl moieties; lipophilic carriers; peptide conjugates; long chain alcohols; phosphate esters; amino; mercapto groups; radioactive markers; nonradioactive markers such as dyes; and polylysine or other polyamines. In one example, the nucleic acid is conjugated to a carbohydrate, sulfated carbohydrate, or glycan.

Kits

Any of the compositions described herein may be comprised in a kit. In a non-limiting example, individual miRNAs are included in a kit. The kit may further include one or more negative control synthetic miRNAs that can be used to control for the effects of synthetic miRNA delivery. The kit may further include water and hybridization buffer to facilitate hybridization of the two strands of the synthetic miRNAs. The kit may also include one or more transfection reagent(s) to facilitate delivery of the miRNA to cells.

In another non-limiting example, multiple synthetic miRNAs are included in a kit. The kit may further include one or more negative control synthetic miRNAs that can be used to control for the effects of synthetic miRNA delivery. The kit may also include one or more transfection reagents to facilitate delivery into cells.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit (labeling reagent and label may be packaged together), the kit also will generally contain a second, third or other additional container into which the additional components may be separately placed. However, various combinations of components may be comprised in a vial. The kits of the present invention also will typically include a means for containing the nucleic acids, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred.

However, the components of the kit may be provided as dried powder(s). When reagents and/or components are provided as a dry powder, the powder can be reconstituted by the addition of a suitable solvent. It is envisioned that the solvent may also be provided in another container means.

The container means will generally include at least one vial, test tube, flask, bottle, syringe and/or other container means, into which the nucleic acid formulations are placed, preferably, suitably allocated. The kits may also comprise a second container means for containing a sterile, pharmaceutically acceptable buffer and/or other diluent. The kits of the present invention will also typically include a means for containing the vials in close confinement for commercial sale, such as, e.g., injection and/or blow-molded plastic containers into which the desired vials are retained.

Such kits may also include components that preserve or maintain the miRNA or that protect against its degradation. Such components may be RNAse-free or protect against RNAses. Such kits generally will comprise, in suitable means, distinct containers for each individual reagent or solution.

A kit will also include instructions for employing the kit components as well the use of any other reagent not included in the kit. Instructions may include variations that can be implemented.

Kits of the invention may also include one or more of the following: miRNA, library of miRNAs, combination library of miRNA, negative control miRNA, nuclease-free water; RNase-free containers, such as 1.5 ml tubes; hybridization buffer; and transfection reagent(s).

It is contemplated that such reagents are embodiments of kits of the invention. Such kits, however, are not limited to the particular items identified above and may include any reagent used for the manipulation or characterization of miRNA.

Sequence Identity

"Sequence identity" is herein defined as a relationship between two or more nucleic acid (nucleotide, polynucleotide, RNA, DNA) sequences, as determined by comparing the sequences. In the art, "identity" also means the degree of sequence relatedness between nucleic acid sequences, as the case may be, as determined by the match between strings of such sequences.

In a preferred embodiment, identity also means identity percentage and can be calculated by the number of equal nucleotides between subject and query, divided by the total length of the query, and multiplied by 100.

"Identity" and "similarity" can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990). The well-known Smith Waterman algorithm may also be used to determine identity.

Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a miRNA molecule, an equivalent or a source thereof or a composition as defined herein may comprise additional component(s) than the ones specifically identified, said additional component(s) not altering the unique characteristic of the invention. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

EXAMPLES

Example 1

Material and Methods

Figure 1A:
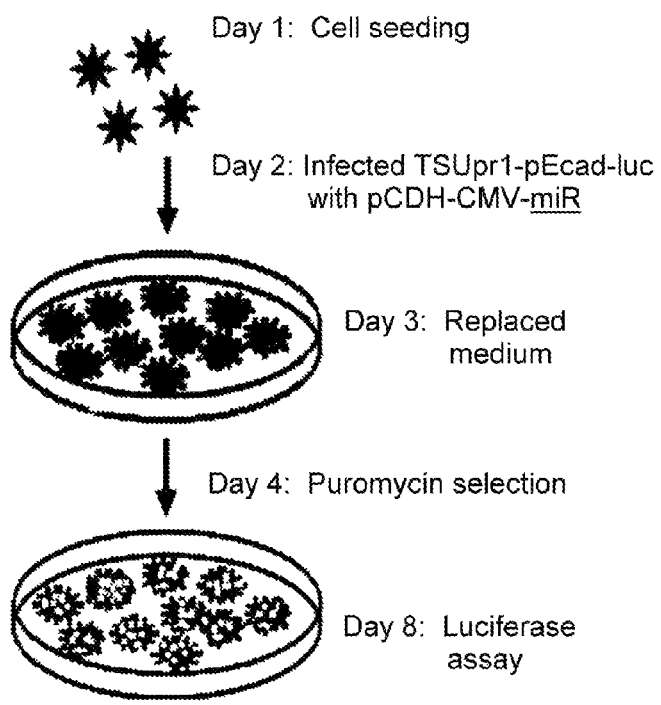
FIG. 1. Flow chart of the screening protocol for EMT reversal, and overview of the results obtained from one of the Lentivirus-based microRNA expression library plates (ITM0081-0160). A, Lentivirus stock (1.0 ul; MOI=3 to 300) was added to TSUpr1-pEcad-Luc cells for 24 hours. Two days post infection (day 4), puromycin selection was applied, and six days after infection (day 8) luciferase activity was measured. B, The background-corrected firefly/*Renilla* luciferase ratios were plotted against the lentiviral MOI. The four miRs with signals significantly above background (FLuc/RLuc ratio>average+2× standard deviation) are encircled. The four control values represent FLuc/RLuc ratios induced by miR-141 and miR-200c, which were supplied in separate tubes (both in duplicate).

Generation of the Lentiviral Library Encoding miRNAs

Human miRNAs were selected from both the public miRNA repository (www.mirbase.org) and proprietary small RNA deep sequencing data (see WO 2007/081204). The miRNA sequences were amplified from their genomic location with amplicons containing the full-length pre-miRNA hairpin and a flanking sequence on both sides of 50-150 basepairs. The primers for the amplicons were designed using Primer3 software (www.geneious.com). If the primer design program could not find appropriate primers in the designated sequences, the requirements for the flanking sequences were adjusted to 0-200 basepairs. The designed primers were complemented with a 5' GCGC overhang and a restriction site for directional cloning. As default the primer upstream of the miRNA was complemented with a BamHI restriction site (GGATCC) and the primer downstream of the miRNA was complemented with an EcoRI restriction site (GAATTC). Primers of amplicons with internal BamHI or EcoRI restriction sites (i.e. occurring in the genomic sequence) were complemented with either a BglII site (AGATCT) or a XbaI site (TCTAGA) respectively. The miRNAs were amplified using the abovementioned primers from human genomic DNA of a single individual in the following PCR reaction:

| constituent | concentration | volume | supplier/cat # |
|---|---|---|---|
| buffer | 10X | 1 uL | Stratagene/600159 |
| dNTPs | 10 mM each | 0.2 uL | GE Healthcare/27-18(5-8)0-04 |
| fwd primer | 10 uM | 0.2 uL | IDT (Integrated DNA Technologies) |
| rev primer | 10 uM | 0.2 uL | IDT (Integrated DNA Technologies) |
| gDNA | 100 ng/uL | 0.1 uL | private source |
| Pfu DNA pol | 2.5 U/uL | 0.1 uL | Stratagene/600159 |
| $H_2O$ | N/A | 8.2 uL | N/A |

| temp (° C.) | time | cycles |
|---|---|---|
| 95 | 2 min | |
| 95 | 15 s | 40 |
| 59* | 15 s | 40 |
| 72 | 90 s | 40 |
| 72 | 15 min | |
| 4 | ∞ | |

*−0.1° C./cycle

All miRNA loci were amplified in separate 10 uL PCR reactions. The products were purified using the Qiagen PCR Clean-Up buffer set and Whatman Unifilter GF/C filter plates (cat #7700-1101). DNA was eluted with 17 uL $H_2O$ per well. The separate eluates were used in the following restriction reaction:

| constituent | concentration | volume | supplier/cat # |
|---|---|---|---|
| buffer E | 10X | 2 uL | Promega/R005A |
| EcoRI* | 12 U/uL | 0.1 uL | Promega/R6017 |

| constituent | concentration | volume | supplier/cat # |
|---|---|---|---|
| BamHI* | 10 U/uL | 0.1 uL | Promega/R6025 |
| eluate | N/A | 16 uL | N/A |
| H$_2$O | N/A | 1.8 uL | N/A |

*Amplicons with internal restriction sites for EcoRI or BamHI were cut with XbaI or BglII respectively instead. The EcoRI + BglII reaction was done with Promega buffer D. The BamHI + XbaI reaction was done with Promega buffer E.

Restriction for 2 hours at 37° C. The separate 20 uL restriction reactions were purified using the Qiagen PCR Clean-Up buffer set and Whatman Unifilter GF/C filter plates (cat #7700-1101). DNA was eluted with 20 uL H$_2$O per well. The separate eluates were used in the following ligation reaction:

| constituent | concentration | volume | supplier/cat # |
|---|---|---|---|
| buffer | 10X | 2 uL | Promega/C1263 |
| T4 DNA ligase | 1-3 U/uL | 0.2 uL | Promega/M1804 |
| restricted pCDH* | 1 ng/uL | 7.8 uL | System Biosciences/CD510B-1 |
| eluate | N/A | 10 uL | N/A |

Ligation overnight at 4° C.
*For directional cloning, pCDH was cut with both EcoRI and BamHI. An alternate construct called pCDH– was made with reversed EcoRI and BamHI restriction sites so that the amplicons with 5' BamHI and 3' EcoRI were cloned in the proper direction. The amplicons with an internal EcoRI site were cut with XbaI and ligated into a pCDH vector that was restricted with XbaI and BamHI.

The resulting ligates were transformed separately into bacteria (Promega Single Step (KRX) competent cells, cat #L3002). 50 uL competent cells was diluted with 950 uL transformation buffer II (10 mM MOPS, 75 mM CaCl$_2$, 10 mM RbCl, 15% glycerol, filter-sterilized). Per 20 uL ligate 20 uL diluted competent cells was added. The mix was incubated for 15 minutes on ice, heat-shocked at 37° C. for 30 seconds, and put back on ice. After 2 minutes the transformed bacteria were reconstituted in 150 uL lysogeny broth (LB). The bacteria were allowed to recover for 20 minutes at 37° C. after which they were plated out separately on ampicillin-containing (50 ug/mL) LB-agar plates and grown overnight at 37° C.

Single colonies of each plate are picked and subcultured overnight in 400 uL ampicillin-containing (50 ug/mL) LB. 1 uL of subculture is lysed in 100 uL water for sequencing purposes. Bacterial lysate is used in the following PCR reaction:

| constituent | concentration | volume | supplier/cat # |
|---|---|---|---|
| buffer | 5X | 1 uL | private source |
| dNTPs | 10 mM each | 0.1 uL | GE Healthcare/27-18(5-8)0-04 |
| pCDH-fwd | 10 uM | 0.1 uL | IDT (Integrated DNA Technologies) |
| pCDH-rev | 10 uM | 0.1 uL | IDT (Integrated DNA Technologies) |
| lysate | 1:100 | 1 uL | N/A |
| Taq DNA pol | unknown | 0.02 uL | private source |
| H$_2$O | N/A | 2.68 uL | N/A |

| temp (° C.) | time | cycles | |
|---|---|---|---|
| 95 | 2 min | | |
| 95 | 15 s | 40 | |
| 59* | 15 s | 40 | *–0.1 ° C./cycle |
| 72 | 90 s | 40 | |
| 72 | 15 min | | |
| 4 | ∞ | | |

| pCDH-fwd | CACGCTGTTTTGACCTCCATAGA |
|---|---|
| pCDH-rev | CACTGACGGGCACCGGAG |
| (SEQ ID NO: 84-85) | |

The PCR products were diluted 25×. 1 uL of diluted PCR product was used in the following Sanger Sequencing reaction:

| constituent | concentration | volume | supplier/cat # |
|---|---|---|---|
| buffer | N/A | 1.9 uL | private source |
| BigDye v3.1 | N/A | 0.1 uL | ABI/4336921 |
| pCDH-seq | 10 uM | 0.1 uL | IDT (Integrated DNA Technologies) |
| PCR product | 1:25 | 1 uL | N/A |
| H$_2$O | N/A | 1.9 uL | N/A |

| temp (° C.) | time | cycles |
|---|---|---|
| 94 | 10 sec | |
| 50 | 5 s | 40 |
| 60 | 2 min | 40 |
| 10 | | |

| pCDH-seq | GACCTCCATAGAAGATTCTAGAGCTAGC |
|---|---|
| (SEQ ID NO: 86) | |

30 u precipitation mix (80% ethanol, 50 mM sodium acetate pH 5.5) was added to each of the sequencing reaction products. The mixes were vortexed for 10 seconds and spun down at 5000 rcf for 45 minutes at 4° C. Supernatant was aspirated and DNA pellets were washed with 30 uL ice cold 80% ethanol and spun at 5000 rcf for 5 minutes at 4° C. Supernatant was aspirated and the DNA pellet was dried on a heat block for 10 minutes. The dry DNA pellet was dissolved in 10 uL H$_2$O. The resulting DNA solution was sequenced on an ABI 3730XL DNA Analyzer. Sequences were compared to the expected genomic sequences. Correct clones were added to the library. For incorrect clones an additional 4 bacterial colonies were picked, and analyzed for insert sequence.

Library constructs were subcultured overnight in 50 mL ampicillin-containing (100 ug/mL) LB and isolated with the Qiagen QIAfilter Plasmid Midi Kit (cat #12245) supplemented with the Qiagen EndoFree Plasmid Buffer Set (cat #19048) according to the instructions of the manufacturer. DNA was dissolved in the supplied TE buffer and brought to a final concentration of 500 ng/uL.

We ordered constructs that we were not able to clone ourselves as minigenes from Integrated DNA Technologies. In these cases, the full-length hairpin plus 20 basepairs flanking each site were cloned into our vector as a service by IDT.

Packaging and virus production was performed by System Biosciences as described in the user manual of CD-500B1-CD523-A1.

Cell Culture

Figure 2:
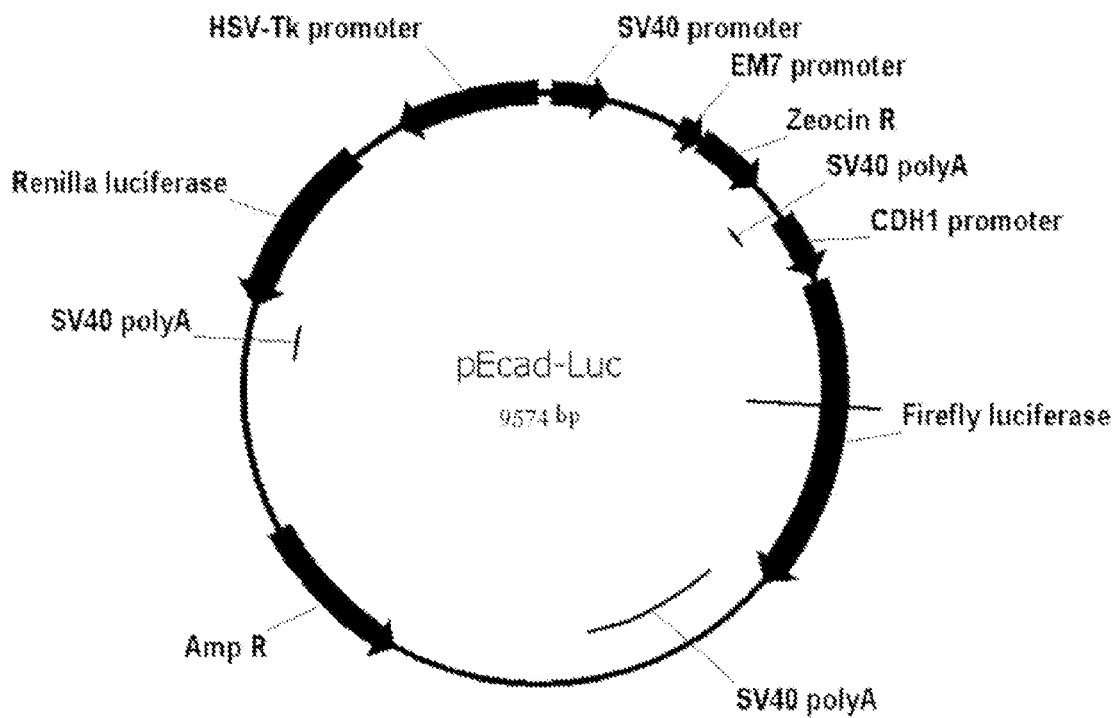
FIG. 2: Overview of the pEcad-Luc/Rluc expression vector. The CDH1 gene promoter (GenBank L34545, position −294 to +44), containing the three E-boxes, was obtained by PCR amplification using human genomic DNA as a template. The CDH1 promoter fragment was cloned upstream of the firefly luciferase gene in the pGL2-basic vector (Promega). The HSV-Tk promoter-driven *Renilla* luciferase cassette was obtained from the pRL-TK vector (Promega), and the SV40 promoter-driven Zeocin antibiotics-resistance cassette from the pVgRXR vector (Invitrogen). The *Renilla* luciferase and the ZeocinR cassettes were cloned into the pGL2-basic vector at the indicated locations.

The TSUpr1/pEcad-luc/Rluc cell line was generated by stable transfection of the human transitional cell bladder carcinoma cell line TSUpr1 with the pEcad-Luc/Rluc expression vector (FIG. 2). A single, zeocin-resistant, clone (clone 1.c.4) was used for all experiments.

TSUpr1/pEcad-luc/Rluc cells were maintained in RPMI-1640 medium (Invitrogen, 31870), supplemented with 10% Fetal Bovine Serum (Sigma, F7524), L-Glutamine (Invitrogen 25030-024) and 50 µg/ml Zeocin (Invitrogen, R250-01). Cells were maintained in a humidified atmosphere at 37° C. and 5% $CO_2$. Cells were split once a week at a 1:20 ratio.

Chemicals

Polybrene (2 µg/ml; Sigma, H9268) was used to increase the efficiency of infection with the miRNA-encoding lentiviral particles. Puromycin (5 µg/ml; Sigma, P8833) was used to select for cells expressing the miRNA of interest. Zeocin (50 µg/ml; Invitrogen, R250-01) was used to maintain integration and expression of the Ecad-luc/Rluc transgene.

MET Screening Protocol:

Day 1: Cell Seeding

TSUpr1/pEcad-luc/Rluc cells were seeded at a density of 2,500 cells per well in 96-well plates (100 µl total volume per well), in duplicate.

Day 2: Lentiviral Infection

The packaged lentiviral constructs were provided as frozen VSV-G pseudotyped viral particles, and are stored at −80° C. Before use, contents were thawed at room temperature and put on ice immediately afterwards. To open tubes a SepraSeal Cap Removal Tool (Fisher Scientific Cat#: 50823908) was used and precipitates were resuspended by pipetting a few times. Medium was removed using a multichannel pipette. Gently, 200 µl of fresh medium (+FBS/glutamine/zeocin) containing 2 µg/ml polybrene (Sigma, H9268) was added to the cells. Next, 1.0 µl of undiluted lentiviral particles was added to each well (in duplicate). On each 96-well plate, miR-141 and miR-200c encoding lentiviral particles were added as positive controls.

Day 3: Refresh Medium

Twenty-four hours after the addition of lentivirus, medium was removed using a multichannel pipette. Cells were washed once with 0.9% NaCl, 50 µl per well. Subsequently, 100 µl fresh medium (+FBS/glutamine/zeocin) was added to each well.

Day 4: Puromycin-Selection

Medium was removed using a multichannel pipette. To select for transduced cells, 200 µl fresh medium containing 5 µg/ml Puromycin (Sigma, P8833) was added to the cells. Note, the cells were not washed in between.

Day 8: Dual-Luciferase Reporter Assay (Promega)

Medium was removed using a multichannel pipette. Next, cells were washed gently with 0.9% NaCl (50 µl/well). To prepare cell lysates, Passive Lysis Buffer 1× (Promega, E1980) was added to the cells (20 µl per well), and incubated at room temperature for 20 minutes on a plate shaker. Cell lysates were transferred to a white 96-well microtiter plates (Thermo Scientific, 9502887). Firefly and *Renilla* luciferase activity were measured on a Victor³ Multilabel Counter (PerkinElmer), according to the manufacturer's instructions.

Total RNA Isolation

TSUpr1/pEcad-luc/Rluc cells were seeded at a density of 15,000 cells per well in 24-well plates. Lentiviral infection was performed as described above. Due to the limited amount of viral particles, virus was added at a multiplicity of infection (MOI) of 30, and if possible an MOI of 100. At day 8, total RNA was isolated using Trizol reagent (200 µl per well), according to the manufacturer's instructions (Invitrogen, 15596-018). Concentration and purity of the RNA was determined on a Nanodrop-1000 spectrophotometer (Thermo Scientific).

Real Time RT-PCR

Two micrograms of total RNA was DNase-1-treated (Invitrogen, 18068-015) and cDNA was synthesized using random hexamer primers and SuperScript II-MMLV reverse transcriptase (Invitrogen, 18064-014). The RT-reaction (30 µl) was diluted 4 times in $H_2O$.

Gene expression was determined by SYBR Green qPCR, using SYBR Green PCR mix (Roche, 04707516001) and 2 µl cDNA as a template. RNA not subjected to reverse transcriptase was used as a negative control for PCR amplification. Gene-specific primers are as follows:

(SEQ ID NO: 48-63)

| Gene | Direction | Sequence |
|---|---|---|
| E-Cadherin | forward1 | 5'-GAAAAGAGAGTGGAAGTG-3' |
|  | reverse1 | 5'-GTGAAGGGAGATGTATTG-3' |
| E-cadherin | forward2 | 5'-CAGGTCTCCTCTTGGCTCTG-3' |
|  | reverse2 | 5'-ACTTTGAATCGGGTGTCGAG-3' |
| N-Cadherin | forward | 5'-GAGGATTAGCCGGAACAACA-3' |
|  | reverse | 5'-AACAAATTTCCCCCATCTCC-3' |
| SNAIL | forward | 5'-AGGATCTCCAGGCTCGAAAG-3' |
|  | Reverse | 5'-GACATCTGAGTGGGTCTGGA-3' |
| SLUG | forward | 5'-TTCGGACCCACACATTACCT-3' |
|  | Reverse | 5'-TTGGAGCAGTTTTTGCACTG-3' |
| ZEB1 | forward | 5'-ATGCGGAAGACAGAAAATGG-3' |
|  | reverse | 5'-GTCACGTTCTTCCGCTTCTC-3' |
| ZEB2 | forward | 5'-CGCTTGACATCACTGAAGGA-3' |
|  | reverse | 5'-CTTGCCACACTCTGTGCATT-3' |
| β2M | forward | 5'-AGCAGAGAATGGAAAGTCAAA-3' |
|  | reverse | 5'-TGCTGCTTACATGTCTCG-3'. |

Q-PCR was performed on a LightCycler LC480 instrument (Roche), using the following amplification conditions: 5 min. 95° C., followed by 45 cycles of 10 sec. 95° C., 20 sec. 60° C., 20 sec. 72° C. For E-cadherin primer set 1, an annealing temperature of 49° C. (instead of 60° C.) was used. Cp values were determined using the LightCycler 480 SW 1.5 software (Roche). Beta-2-microglobulin expression was used for normalization. Relative gene expression levels were calculated according to the model described by Pfaffl (18).

Stem-Loop RT-PCR

MicroRNA expression was determined by stem-loop RT-PCR as described (19). For this, 100 ng total RNA was reverse transcribed using 0.375 µmol miR-specific stem-loop (SL) primers:

```
                                          (SEQ ID NO: 64-71)
miR-141:
5'-GTCGTATCCAGTGCAGGGTCCGAGGTATTCGCACTGGATACGAC

CCATCT-3' miR-200c:
5'-GTCGTATCCAGTGCAGGGTCCGAGGTATTCGCACTGGATACGAC

TCCATC-3' miR-181a-1:
5'-GTCGTATCCAGTGCAGGGTCCGAGGTATTCGCACTGGATACGACA

CTCAC-3' miR-124*:
5'-GTCGTATCCAGTGCAGGGTCCGAGGTATTCGCACTGGATACGAC

GGCATT-3' miR-518b:
5'-GTCGTATCCAGTGCAGGGTCCGAGGTATTCGCACTGGATACGACA

CCTCT-3' miR-520f:
5'-GTCGTATCCAGTGCAGGGTCCGAGGTATTCGCACTGGATACGAC

AACCCT-3' miR-524-5p:
5'-GTCGTATCCAGTGCAGGGTCCGAGGTATTCGCACTGGATACGAC

GAGAAA-3' miR-524-3p:
5'-GTCGTATCCAGTGCAGGGTCCGAGGTATTCGCACTGGATACGAC

ACTCCA-3'
``` in 1×RT buffer, containing 0.25 mM dNTPs, 3.33 U/µl SuperScript II-MMLV reverse transcriptase (Invitrogen) and 0.25 U/µl HRP-I RNase Inhibitor (Amersham), for 30 min. at 16° C., 30 min at 42° C. and 5 min at 85° C. Stem-loop RT products were diluted 2 times in H₂O.

MicroRNA expression was determined by SYBR Green qPCR, using PCR mix (0.5 µl forward primer (25 µmol/µl), 0.5 µl reverse primer (25 µmol/µl), 8 µl H₂O, 10 µl 2×SYBR Green PCR mix, Roche) and 2 µl of stem-loop RT product as a template. RNA not subjected to SL-RT was used as a negative control for PCR amplification. The miR-specific primers are as follows:
Forward Primers:

```
                                          (SEQ ID NO: 72-80)
   miR-141:       5'-GCCCGCTAACACTGTCTGGTAAAG-3' miR-200c:      5'-GCCCGCTAATACTGCCGGGTAATG-3' miR-181a-1:    5'-TGCCAGAACATTCAACGCTGTCG-3' miR-124*:      5'-TGCCAGTAAGGCACGCGGTGA-3' miR-518b:      5'-TGCCAGCAAAGCGCTCCCCTTTAG-3' miR-520f:      5'-GCCCGCAAGTGCTTCCTTTTAGAG-3' miR-524-5p:    5'-GCCCGCCTACAAAGGGAAGCACT-3' miR-524-3p:    5'-TGCCAGGAAGGCGCTTCCCTTTG-3'

A universal reverse primer was used:
   5'-GTGCAGGGTCCGAGGT-3'
```

Q-PCR was performed on a LightCycler LC480 instrument (Roche), using the following amplification conditions: 5 min. 95° C., followed by 45 cycles of 10 sec. 95° C., 20 sec. 60° C., 10 sec. 72° C. Cp values were determined using the LightCycler 480 SW 1.5 software (Roche). Expression of the U6 snRNA (RNA6-1) was used for normalization (U6 (RNU6-1) primers: RT 5'-GTCATCCTTGCGCAGG-3' U6 forward 5'-CGCTTCGGCAGCACATATAC-3' and U6 reverse 5'-AGGGGCCATGCTAATCTTCT-3' (SEQ ID NO: 81-83). Relative miR expression levels were calculated according to the model described by Pfaffl (18).

DNA Sequence Analysis

The sequence of the cloned miRNAs in the lentiviral vectors for the hits as described in Table 1 was verified as follows. Total nucleic acids of lentiviral transduced cells were isolated using Trizol reagent, according to the manufacturer's instructions (Invitrogen, 15596-018). Concentration and purity of the nucleic acids was determined on a Nanodrop-1000 spectrophotometer (Thermo Scientific). Proviral DNA was amplified by PCR, using 500 ng of nucleic acids as input, and pCDH lentiviral vector-specific primers (forward: 5'-CACGCTGTTTTGACCTCCATAGA-3', reverse: 5'-CACTGACGGGCACCGGAG-3', (SEQ ID NO: 84-85).) for 35 cycles at an annealing temperature of 65° C. Amplified products were purified using the Wizard PCR preps DNA purification system (Promega). DNA sequence analysis was performed using 2 µl of purified amplicon, 5 pmoles of pCDH-specific primer (5'-GACCTCCATAGAAGATTCTA-GAGCTAGC-3', (SEQ ID NO: 86).), and the Big Dye Terminator v 1.1 kit (Applied Biosystems). Products were analyzed on a 3730 DNA Analyzers (Applied Biosystems). Data were collected using the Collection Software v3.0 and analyzed using the Sequencing Analysis v5.3.1 program (Applied Biosystems). The sequence for all cloned miRNAs was correct and is given in Table 4.

Results

Mesenchymal to Epithelial Transition (MET) microRNA Screening

EMT in tumor cells results from a transcriptional reprogramming of the cell. In particular the transcriptional repression of the E-cadherin (CDH1) gene promoter has been shown to trigger the EMT phenotype. The E-cadherin protein is one of the most important cadherin molecules mediating cell-cell contacts in epithelial cells/tissues. CDH1 is repressed by binding of the transcriptional repressors, SNAI1, SNAI2, TCF3, TWIST, ZEB1 or ZEB2 (20-23), to three so-called E-boxes in the CDH1 proximal promoter region (24-26). Inhibiting the binding of these repressors to the CDH1 promoter can revert EMT, also called mesenchymal-to-epithelial transition (MET), and inhibits tumor cell invasion and tumor progression in animal models (27). We hypothesized that an extensive set of microRNAs is able to induce MET, by targeting one of the EMT-associated transcriptional repressors. Suppression of the EMT-associated transcriptional repressors will result in the re-activation of CDH1 gene expression. This re-activation of CDH1 can be easily monitored by CDH1 promoter-driven firefly luciferase activation. Therefore, we cloned the core element of the CDH1 gene promoter, containing the three E-boxes (24;25), in an expression vector to drive firefly luciferase expression. As an internal control, a HSV-Tk promoter-driven Renilla luciferase cassette was inserted into the same vector (pEcad-Luc). We have stably transfected the bladder cancer cell line TSUpr1 with this reporter construct. Endogenous CDH1 mRNA expression in this cell line is undetectable, whilst several mesenchymal markers are expressed (24;28).

microRNA-Induced MET Screening: SETUP

TSUpr1-pEcad-Luc cells are susceptible to puromycin selection. As a first step in setting up the screening model, we determined the transduction efficiency of TSU cells. TSU cells were infected with a eGFP-expressing lentivirus at different MOIs, and transduced cells were selected in puromycin-containing medium. The number of infected, and hence puromycin-resistant, cells was determined by a MTT cell survival assay. In two independent experiments, we have shown that at an MOI of 8, a transduction efficiency (MTT of infected cell+puro/MTT of infected cell-puro×100%) of at least 60% could be achieved. Based on these results, we decided to perform the pilot infection experiments at an MOI of 3 and 30.

Recently, the miR-200 family and miR-205 were shown to regulate EMT by targeting ZEB1 and ZEB2 (13-15). Two miRNAs of the miR-200 family, miR-141 and miR-200c, were selected to setup and optimize our MET screening assay. TSU cells were infected with both miRNA vectors (MOI=30). Two (day 4) and six (day 8) days post infection, E-cadherin promoter-driven firefly luciferase activity was measured and normalized against the HSV-Tk controlled *Renilla* luciferase activity. At day 8, the FLuc/RLuc ratio was induced more than 2-fold by miR-200c, and more than 1.5-fold by miR-141 (FIG. 1; Table 1). To decrease the 'noise' of uninfected cells (FLuc– and RLuc+), puromycin selection was applied. The miR-141 and miR-200c-induced FLuc/RLuc ratios were comparable to those without selection.

Figure 1B:
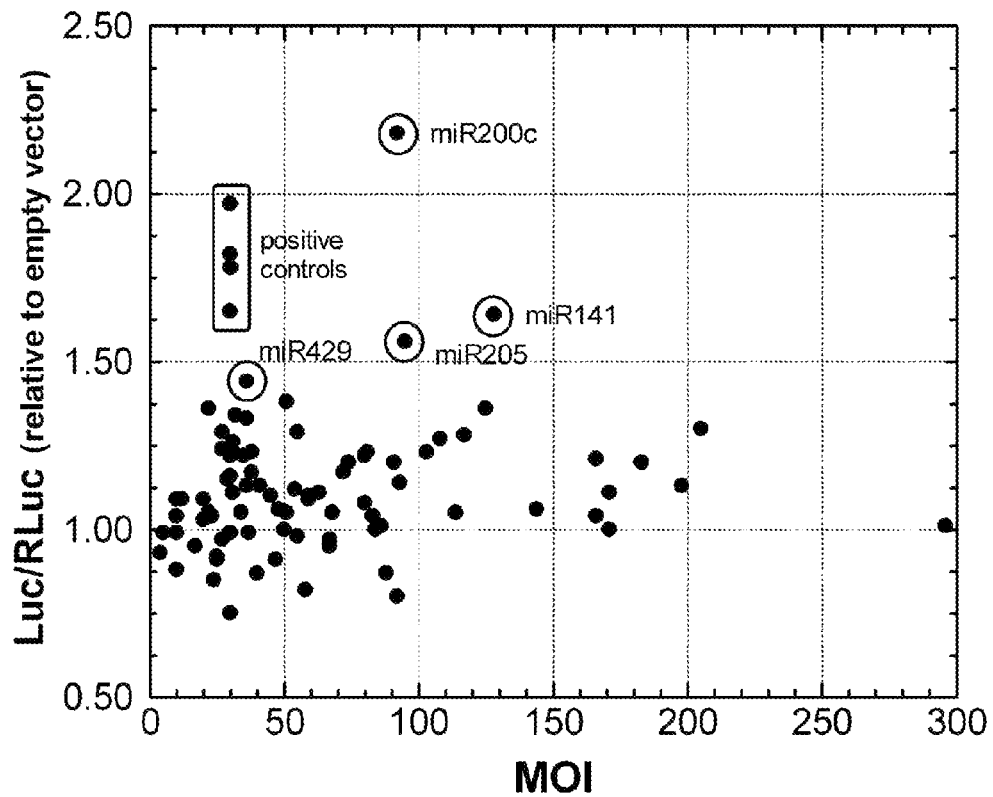

TSU cells were infected with 0.2 microliter of undiluted miR-lentivirus. Two days after infection, puromycin selection was applied for 4 days. Six days post-infection luciferase activities were measured. The result of screening of the first 80 microRNAs is shown in FIG. 1. The four positive 'hits' (FLuc/RLuc>average+2×SD) were microRNAs known to regulate EMT, i.e. miR-141, miR-200c, miR-205, and miR-429. This pilot experiment indicated the validity of the screening system.

microRNA-Induced MET Screening

Several lentiviral constructs in the miR library have very high titers. Therefore, without dilution of virus stocks prior to infection, in some cases high MOIs of virus were applied. The addition of miR-141 and miR-200c lentivirus at high MOI (100 to 600) had no significant toxicity, whilst the induction of the FLuc/RLuc ratio was slightly enhanced. Therefore, the entire lentivirus-based microRNA expression library was screened using one microliter of undiluted lentivirus (all in duplicate). After screening all 1120 miRs (14 plates, each containing 80 miR vectors), 65 positive 'hits' (FLuc/RLuc>average+2×SD) were found. In addition to these 65 miRs, 59 additional miRs were selected based on, e.g. increased Luc signal with increased RLuc signal, leaving the ratio below the threshold. These 124 miRs were re-screened in the TSUpr1-pEcad-luc model, after which 30 miRs with a reproducible positive FLuc/RLuc ratio remained (26 of 30 from the group of 65 'hits').

Preliminary MET microRNA Validation

To further validate and select miRs relevant for EMT/MET regulation, we studied their effects on endogenous gene expression, i.e. CDH1 (E-cadherin), CDH2 (N-cadherin), SNAI1 (SNAIL), SNAI2 (SLUG), ZEB1 (deltaEF1) and ZEB2 (SIP1). TSUpr1-pEcad-luc cells were infected with the 30 miRs identified by MET screening (MOI=30 and 100). Six days after infection, total RNA was isolated and used for qPCR analysis of the above-mentioned genes (Table 1). The expected upregulation of CDH1 (E-cadherin) expression was only observed with a few miRs (n=10), as was the downregulation of CDH2 (N-cadherin) expression (n=8). Of those miRs, miR-181a-1, miR-200a, mir-429 and miR-524 resulted in both upregulation of CDH1 and downregulation of CDH2. The kinetics of cadherin expression by EMT-associated miRs is cadherin-dependent. This may explain the non-consistent up and down regulation of both cadherins, at the chosen time point (6 days post miR introduction). The hallmark of EMT or the reverse, MET, is cadherin switching. Therefore, the (relative) ratio of CDH1/CDH2 expression was used as a measure to study the role of the identified miRs on EMT regulation. As shown in Table 1, ten miRs (out of 12) had an increased CDH1/CDH2 ratio (range: 1.85-17.65). The other two miRs induced CDH1 expression significantly (in line with the FLuc induction), but these miRs also substantially (>2-fold) induced CDH2 expression. Of the 12 miRs that induced endogenous CDH1 expression or induced a cadherin switch, all also down regulated at least one CDH1 transcriptional repressor at the RNA level.

Conclusions

In the set of 12 selected miRs, the known EMT-associated miRs (miR-200 family and miR-205) are present, which confirms the specificity of our system. Of the remaining 9 miRs, three miRs (miR-518b, miR-520f and miR-524) belong to the human miR-515 family. In this study, the miR-200 family members in general down regulated ZEB2 expression, which was associated with down regulation of CDH2 expression (at day 8). On the other hand, the miR-515 family members in general down regulated SNAI2 expression, which was associated with up regulation of CDH1 expression. These remarkable differences may underlie two different mechanisms of EMT regulation by the miR-200 and miR-515 family members. Expression and function of the 3 miR-515 family members has not been studied and reported in the publically available databases, and therefore provides a first insight over the role of these miR in EMT.

Example 2

Materials and Methods

Cell Culture

TSUpr1/pEcad-luc/Rluc (a.k.a. TSUpr1-pEcad) cells and the PC-3 prostate cancer cell line (ATCC# CRL-1435) were maintained in RPMI-1640 medium (Invitrogen, 31870), supplemented with 10% Fetal Bovine Serum (Sigma, F7524), L-Glutamine (Invitrogen 25030-024) and for TSUpr1/pEcad-luc/Rluc 50 µg/ml Zeocin (Invitrogen, R250-01). Cells were maintained in a humidified atmosphere at 37° C. and 5% $CO_2$.

Generation of an Inducible miRNA Expression System

To facilitate long-term and controlled miRNA expression, use was made of the Tet-inducible miR-X miRNA expression system (Clontech Inc.). The miRNA precursor was cloned in the 3'UTR of the ZsGreen fluorescent protein transcription unit. MiRNA expression is governed in the vector by the tightly regulated, inducible promoter Ptight, and the activity of the co-expressed transactivator (Tet-on). In the presence of doxycycline the Ptight promoter will be activated, resulting in the co-expression of high levels of miRNA and ZsGreen1 protein, with low levels of expression in non-induced cells.

Figure 5A:
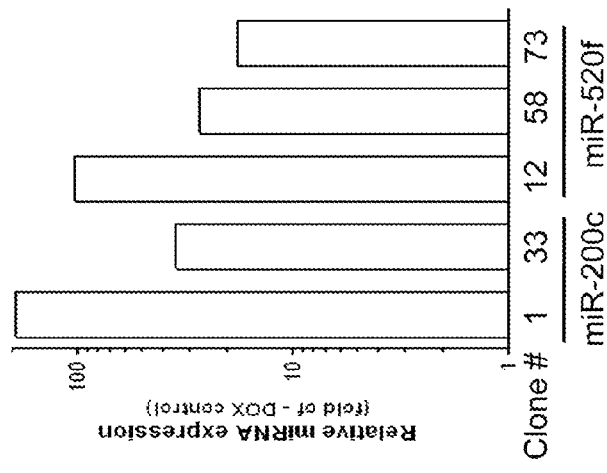
FIG. 5: Creation of doxycycline inducible miRNA expression systems. A, The miR-200c and miR-520f precursors were isolated from the provirus integrated into pCDH-lentivirus infected TSUpr1 cells (in the miR screening experiments) by restriction enzyme digestion. The miR precursors were cloned into the NheI/EagI sites of the pmRi-ZsGreen1 inducible miR expression vector (Clontech PT5049-1). Map of the miR-520f expression vector is shown. B, PC3 cells (ATCC# CRL-1435) were transfected with the pTet-on-advanced vector (Clontech PT3899-5), and selected in G418 (300 ug/ml)-containing medium. Cells were transiently transfected with the pTRE-Luc reporter vector, treated with 0, 0.1 and 1.0 ug/ml doxycycline (DOX, Sigma D9891) for 2 days, and then analyzed for Luc activation. C, PC3-Tet-on cells (clone 8) were then transfected with the pmRi-ZsGreen1-miR-200c or miR-520f vector, and selected in puromycin (5 ug/ml)-containing medium. Stable clones of PC3-mRi-ZsGreen-miR-X were tested for the induction of miRNA and gene expression. Cells were treated with 0 and 1.0 ug/ml DOX for 4 days, total RNA was isolated, and miRNA and gene expression (Table 8) were analyzed by qPCR.

The miR-200c and miR-520f precursors were PCR amplified, using proviral DNA of lentivirus-infected TSUpr1 cells as a template, and the universal pCDH forward and reverse vector-specific primers (SEQ ID NO: 84-85). The amplification products were digested with EcoRI/NheI; these sites are from the lentiviral pCDH vector multiple cloning site. The digested fragments were cloned into the EcoRI/NheI sites of a modified pEGFP-N3 vector (Clontech #6080-1), which was obtained by BamHI/NotI excizing the EGFP ORF from the vector, and closing the vector after Klenow DNA polymerase-mediated filling-in of the BamHI and NotI overhangs. The miR precursor was excised from this vector by EagI/NheI-digestion and cloned into the EagI/NheI sites of the pmRi-ZsGreen1 vector (Clontech PT5049-1; FIG. 5A). Proper cloning was confirmed by DNA sequence analysis. The pTet-on transactivator vector (Clontech PT3899-5) was transfected into the PC3 prostate cancer cell line (ATCC#CRL-1435). G418-resistant clones were tested for proper pTet-on activity, in a transient pTRE-luciferase-reporter assay.

Next, the pmRi-ZsGreen1-miR-X vectors were transfected into the PC3-Tet-on cells (clone 8), along with a puromycin selection marker. Puromycin-resistant colonies were selected, and quick-screened for DOX-inducible ZsGreen1 expression (by fluorescence measurement in 96 well plates on the Victor3 multimeter). ZsGreen1-positive cells were further analyzed for DOX-inducible miRNA expression.

Cell Invasion Assays

Figure 6B:
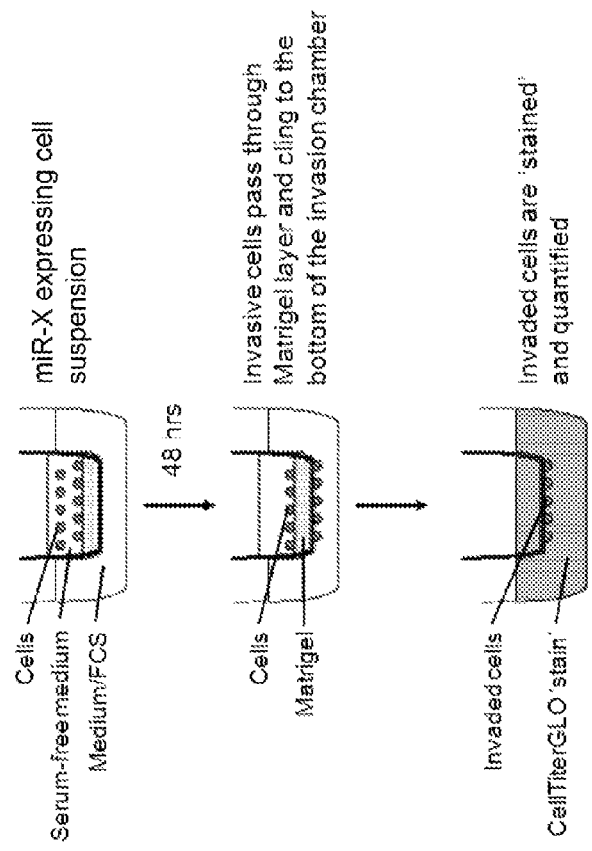
FIG. 6: Influence of miRNAs on tumor cell invasion. A, Fifty thousand (PC3) or fourty thousand (TSUpr1) cells were seeded into Biocoat Matrigel Invasion chambers, 8 micron (BD 354480), in serum-free medium. The invasion chamber was placed in a 24-well containing medium with 10% fetal calf serum as chemoattractant. As a control, the same amount of cells was seeded onto the surface of a 24-well culture plate. After 48 hours incubation, cells in the invasion chamber were removed by aspiration and cleaning the inner compartment with a cotton swab. The invasion chamber was then put into CellTiter-GLO (CTG, Promega-G7571) cell viability reagent, and incubated for 15 minutes. CTG activity was measured on a Victor3 luminometer. B, Cell invasion assays were performed with PC3-mRi-ZsGreen1-miR-X cells that were pre-treated for 2 days with 1 ug/ml DOX. In addition, PC3 cells infected with miR-200c and miR-520f lentivirus (MOI=30), and selected on puromycin for 4 days, were used. The percentage of cell invasion was calculated as the CTG activity on the lower part of the membrane divided by the total CTG activity (of the cells grown on the surface of a 24 well culture plate). Inhibition of cell invasion by a specific miRNA was calculated by dividing the percentage of cell invasion versus untreated (−DOX) or control (empty vector virus) cells. C, Relative microRNA expression levels in parallel cultures were determined by stem-loop RT-qPCR. D, Cell invasion assays were performed with TSUpr-pEcad cells that were infected with empty-vector, miR-124-1, miR-181a-1, miR-200c, miR-206, miR-518b, miR-520f or miR-524 precursor-containing lentivirus (MOI=30), and selected on puromycin for 4 days. Cell invasion was calculated as described in FIG. 6B.
Figure 6A:
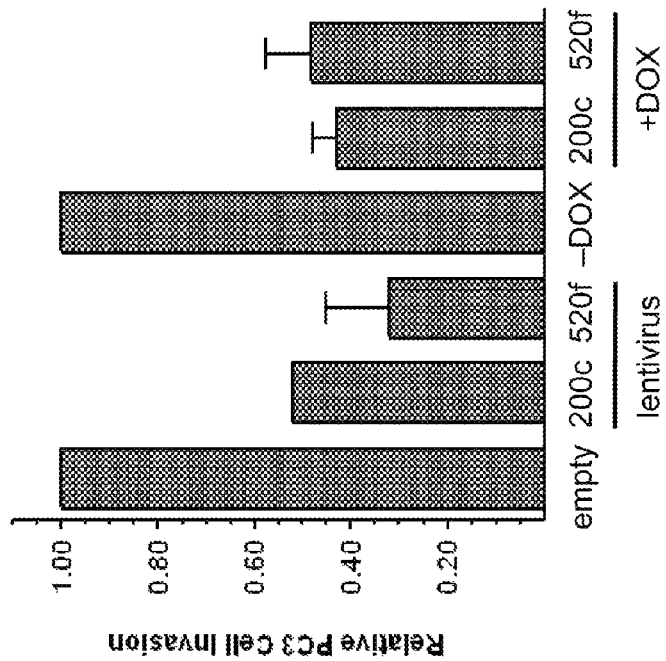

For cell invasion assays, DOX-inducible PC3-mRi-ZsGreen1-miR-X cells were incubated in the presence of DOX (1 ug/ml) for 2 days, prior to the invasion assay. PC3 and TSUpr1-pEcad cells were transduced with miR-expressing lentiviral particles (MOI=30), as described in example 1. The lentiviral transduced cells were puromycin-selected and passaged 1 time before use. Fifty thousand (PC3) or 40,000 (TSUpr1-pEcad) cells were seeded into Biocoat Matrigel Invasion chambers (8 micron; BD 354480) in serum-free medium (FIG. 6A). The invasion chamber was placed in a 24-well containing medium with 10% fetal calf serum as chemo-attractant. As a control, the same amount of cells was seeded in 24-well culture plates. After 48 hours incubation, cells in the invasion chamber were removed by aspiration and cleaning the inner compartment with a cotton swab. The invasion chamber was then put into CellTiter-GLO (CTG, Promega-G7571) cell viability reagent, incubated for 15 minutes, and then analyzed on a Victor3 luminometer. Cell invasion was calculated as the CTG activity on the lower part of the membrane divided by the CTG activity of the cells grown in a 24 well plate. Inhibition of cell invasion by a specific miRNA was calculated by dividing the percentage of cell invasion of DOX-treated cells versus untreated cells, or invasion of transduced cells versus empty-vector-transduced cells.

Real Time RT-PCR

The same protocol as described under example 1 was used to RT-PCR the following genes: vimentin and CDH11 and HPRT. The following primers were used for the respective genes:

```
                                    (SEQ ID NO: 112-117)
HPRT      forward  5'-CTCAACTTTAACTGGAAAGAATGTC-3' reverse  5'-TCCTTTTCACCAGCAAGCT-3'

Vimentin  forward  5'-GGCTCAGATTCAGGAACAGC-3' reverse  5'-GCTTCAACGGCAAAGTTCTC-3'

CDH11     forward  5'-GGTCTGGAACCAGTTCTTCG-3' reverse  5'-GGCATGAATGTTCCCTGATT-3'
```

Figure 3:
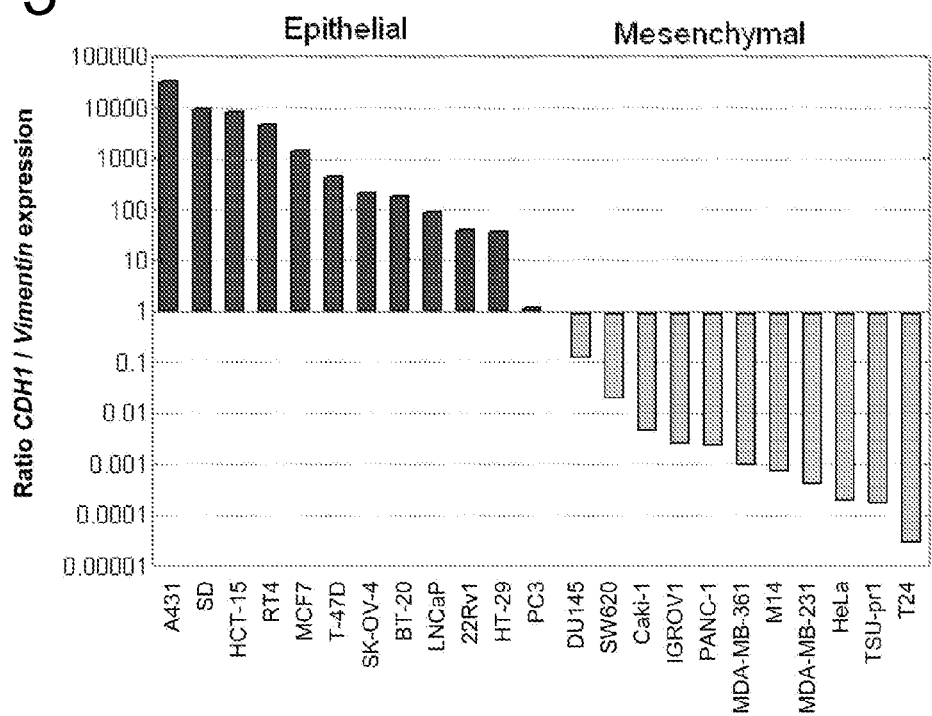
FIG. 3: Characterization of tumor cell line models. Total RNA was isolated from 70-80% confluent cell line cultures, and analyzed for CDH1 and Vimentin expression by qPCR. Relative expression values were plotted, and cells with high CDH1/low VIM and low CDH1/high VIM were designated epithelial and mesenchymal, respectively.
Figure 4A:
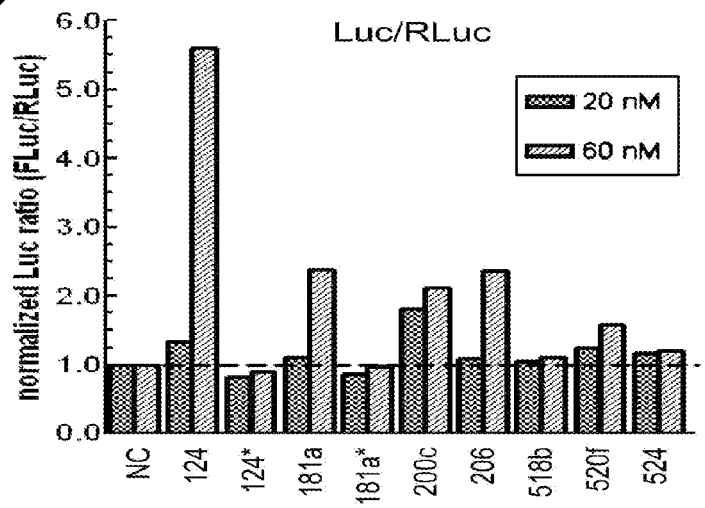
FIG. 4: MET induction using synthetic miRNA mimics. A, TSUpr1-pEcad-Luc cells were transiently transfected with 20 to 60 nM of synthetic miR mimics (Ambion or Dharmacon; see Table 7 for details). Four days post-transfection, Luc and RLuc activity were measured, and the Luc/RLuc ratios were normalized for negative control (NC)-transfected cells. B, Cells were transfected and treated as described in FIG. 4A. Total RNA was isolated and used for miRNA and gene qPCR analysis. Expression levels of CDH1 and CDH2, normalized to the HPRT housekeeping gene, as percentage of NC-transfected cells are shown. C, Different parental tumor cell lines were transfected with miR-200c and miR-520f mimics and other miR mimics and analyzed for CDH1 expression (as described in FIG. 4B).
Figure 4B:
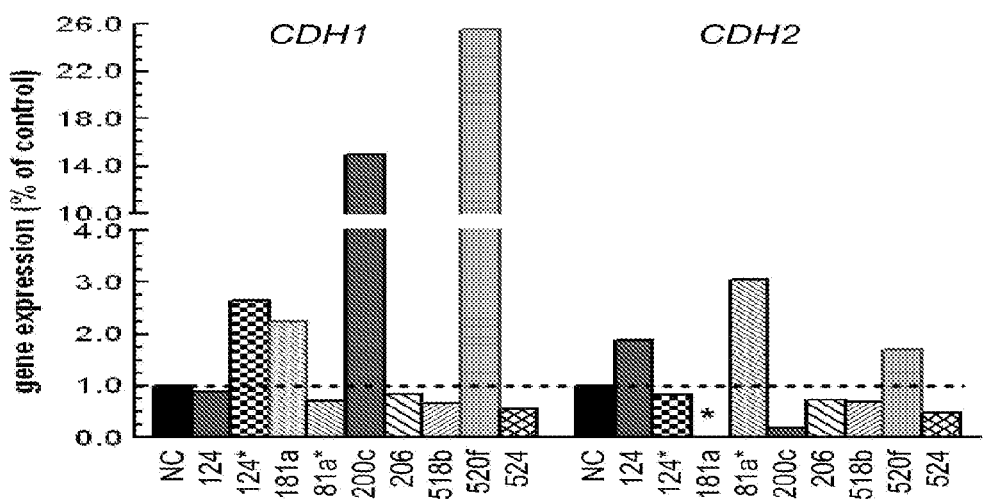
Figure 4C:
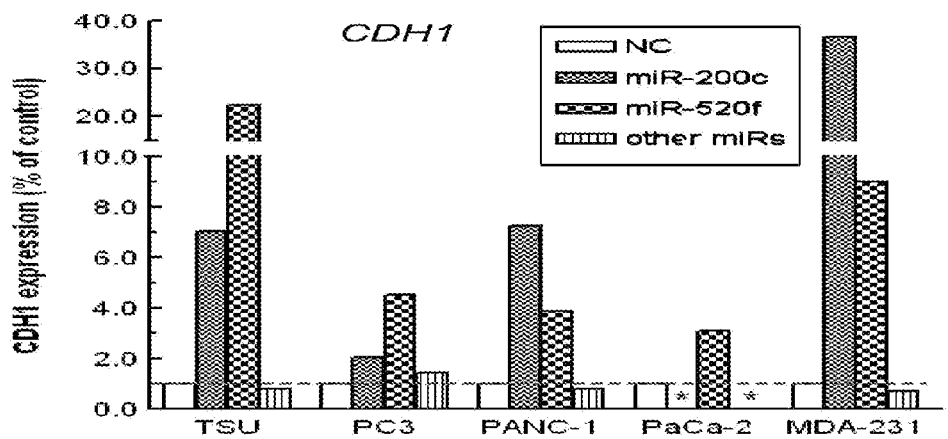

Results
Validation of the MET-Inducing microRNAs
In Vitro Validation Using microRNA Mimics To validate the microRNAs identified by screening a lentiviral miRNA expression library, synthetic miRNA mimics were used. Synthetic miR mimics used were supplied by Ambion or Dharmacon (Thermo Scientific); see Table 7 for details. MiR-200c mimics of both companies were compared and showed equal efficacy (i.e. CDH1 induction; data not shown). TSUpr1-pEcad-luc/Rluc cells were transiently transfected with 20 to 60 nM of synthetic miR mimics. Four days post-transfection, Luc and RLuc activity were measured, and the Luc/RLuc ratios were normalized for negative control (NC) mimic-transfected cells. Of all of the mimics tested, miR-124, 181a, 200c, 206 and miR-520f showed an induction of the Luc/RLuc ratio (FIG. 4A). Except for miR-200c and miR-520f, the other miR mimics downregulated RLuc activity, and displayed cellular toxicity (not shown). Of all these miRs, miR-200c and miR-520f strongly induced (~20-fold) endogenous CDH1 expression, whilst miR-124* and miR-181a induced CDH1 about 2.5-fold (FIG. 4B). MiR-200c, miR-518 and miR-524 downregulated CDH2 expression more than 30% (FIG. 4B). The efficacy of the miR mimics was further tested in several other tumor cell lines with a mesenchymal-like phenotype (based on the CDH1 and vimentin mRNA expression ratios; FIG. 3). Like in TSUpr1-pEcad-luc/Rluc, miR-200c and miR-520f also induced CDH1 expression in wild-type TSUpr1, PC3, PANC-1, MIA-PaCa2, and MDA-MB-231 cells (FIG. 4C).

Generation of an Inducible miRNA Expression System

Figure 5B:
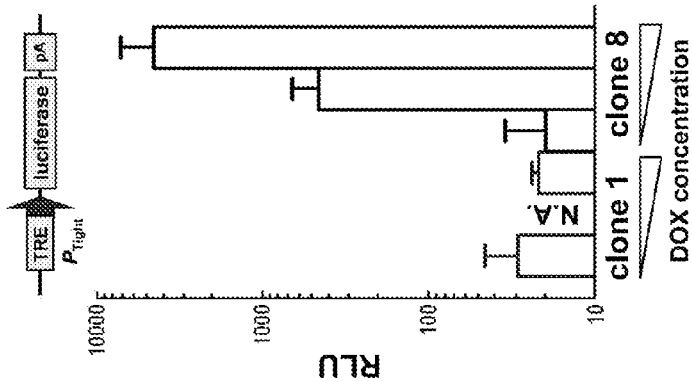
Figure 5C:
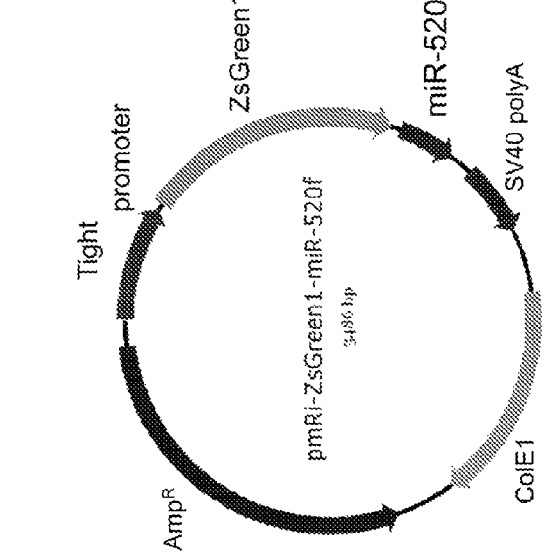

G418-resistant clones were tested for proper pTet-on activity, in a transient pTRE-luciferase-reporter assay. Upon doxycycline (DOX) treatment (0.1 and 1.0 ug/ml), clone 8 showed a strong induction of luciferase expression, whilst Luc activity in non-induced cells (no DOX) did not exceed background levels (FIG. 5B). As shown in FIG. 5C, several pmRi-ZsGreen1-miR-X transfected clones displayed DOX-inducible miR-200c or miR-520f expression, which was DOX dose dependent, reaching maximum levels at about 1 ug/ml DOX (not shown).

Endogenous gene expression in the inducible miR-200c and miR-520f expressing cells was analyzed by qPCR. Upregulation of CDH1 was observed, whilst downregulation of CDH11 and vimentin was observed repeatedly for both miRs (Table 8). PC3 cells also showed the weakest induction of CDH1 by miR-200c and miR-520f mimics of all cell lines tested. In addition to the down-regulation of mesenchymal markers, transcriptional repressors, such as ZEB1, ZEB2 and SNAI2 were also downregulated after induction of miR-200c and miR-520f (Table 8). Collectively, these data indicate that in the miR-200c and miR-520f inducible cell lines, the corresponding miRs as well as their direct and indirect EMT target genes can be regulated at the molecular level.

Inhibition of Tumor Cell Invasion

Figure 6D:
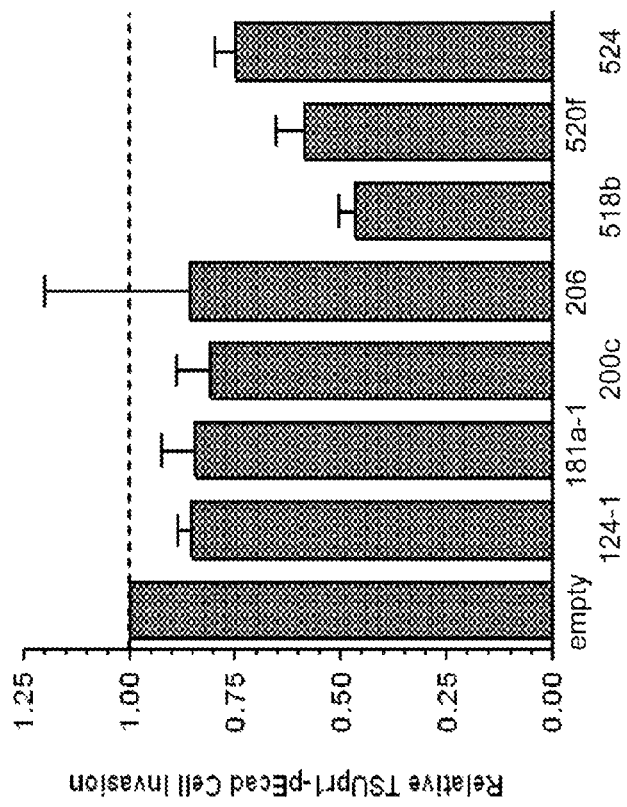
Figure 6C:
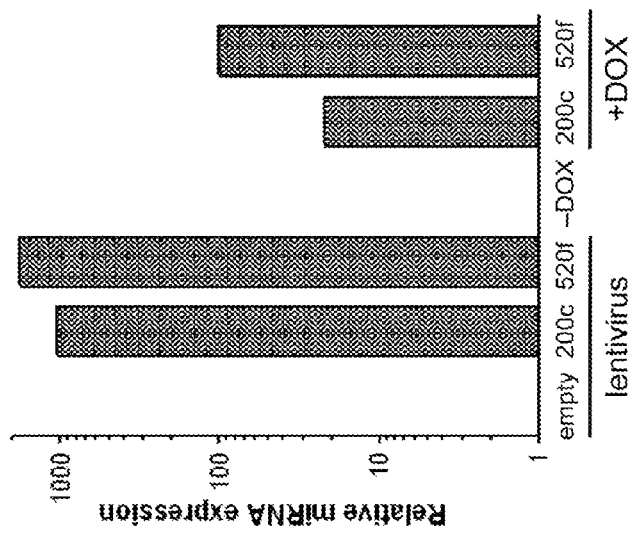

To study whether the identified miRs also regulate EMT at the cellular level, cell invasion assays were performed using the miR-520f and miR-200c inducible stable clones as generated above, and miR-200c and miR-520f expressing lentivirus as described above. All miR-200c and miR-520f clones tested, inhibited cell invasion in the range of 48-68% (FIG. 6B). Induction of miRNA expression was determined in parallel cultures and found positive (FIG. 6C). MiR levels did not show a significant correlation with invasion percentage. These data indicate that miR-520f, identified in the Luc screening assay as an MET-inducing miRNA, could also revert one of the key cell biological aspects of EMT, namely cell invasion.

To confirm the effect of the other miR-515 family members, miR-518b and miR-524, on cell invasion was tested in the TSUpr1/pEcad-luc/Rluc screening model. TSUpr1-pEcad cells were infected with miR-precursor containing lentivirus. All three miRs belonging to the same miR-515 family, miR-518b, miR-520f and miR-524, inhibited cell invasion by 25-53% (FIG. 6D). Expression of the corresponding mature miRNAs was confirmed by stem-loop qPCR (as described in example 1; not shown).

Conclusions

The three miR-515 family members, miR-518b, miR-520f and miR-524, were identified in the MET screening. Mimics for miR-518b and miR-524 downregulated the expression of the mesenchymal marker CDH2, whereas, miR-520f mimics strongly upregulated the expression of the epithelial marker CDH1 in several cell line models. Cell invasion of PC3 cells through Matrigel was inhibited after induction of miR-520f expression. The anti-invasion effect was also observed when all three miRNAs were expressed in the TSUpr1-pEcad screening model. In fact, miR-200c did not reduce invasion in this model. This indicates the great potentcy of these three miR-515 members as having anti-invasion activity in several cell and tumor types in contrast to miR-200c.

Inhibition of Metastasis Formation in an Animal Model

The fact that these three miR-515 family members could activate the E-cadherin gene promoter in vitro, based on luciferase reporter activation, and endogenous CDH1 induction (miR-520f) or decrease CDH2 expression (miR-518b and miR-524), and could all inhibit tumor cell invasion in vitro, indicates that these microRNAs are potent tools to inhibit the invasion and metastasis of tumor cells in vivo. To confirm the anti-metastatic activity of miR-520f, miR-518b and miR-524 in an in vivo setting, an experimental tumor metastasis experiment was set up. Male, immunodeficient, BALB/c nude mice (6-8 weeks old) are injected with 0.5×106 (200 μl volume) PC3-mRi-ZsGreen1 cells expressing either miR-520f, miR-518b and miR-524, via the (lateral) tail vein (29). Groups of 6 mice are given DOX-containing (0.2 mg/ml) drinking water during the entire experiment, and a control group of mice injected with non-DOX treated PC3-mRi-ZsGreen1 cells expressing either miR-520f, miR-518b and miR-524 receive DOX-free water. Mice are monitored daily, and if not suffering from serious inconvenience, are sacrificed after 2 months. The lungs are the primary site of metastasis, since it contains the first capillary bed the injected cells will encounter after injection (30, 31). It is suggested that cells passing the lung capillary bed, may also form metastasis in other organs (30). The number and size of metastasis are determined macroscopically (i.e. by visual examination through a dissection microscope) and microscopically (i.e. by studying ZsGreen expression in lung and other tissue sections). It is anticipated, based on all available data presented above, that cells expressing either miR-520f, miR-518b or miR-524 form less (and smaller) metastasis in this animal model than cells that do not express said miRNAs.

This proof of concept will pave the way for further preclinical testing of miR-520f, miR-518b and miR-524 as a drug to treat EMT-associated diseases.

To further confirm the inhibitory effect of miR-520f, miR-518b and miR-524 on metastasis in vivo, different tumor cell lines, engineered with pmRi-ZsGreen1-miR-520f, 518b or 524, are orthotopically injected into nude mice (NOD-SCID or BALB/c nu/nu). At different times after tumor cell injection, mice receive DOX-containing or DOX-free water. Local invasion and distant metastasis to the lungs and other organs are monitored by in vivo imaging of ZsGreen1 or LUC. Over-expression of miR-520f, miR-518b or miR-524 (induced by DOX in the drinking water) is expected to reduce the number of metastases. Moreover, mice orthotopically injected with tumor cells, in which miR-520f, miR-518b or miR-524 was activated, are expected to have a mean survival rate that will be significantly prolonged compared with that of mice not receiving DOX (i.e. no miR-520f, miR-518b or miR-524 activation in tumor cells). Survival of the animals will be defined by serious complication-free survival.

TABLE 1

List of microRNAs identified by MET (Luciferase) screening and regulation of endogenous EMT-associated genes. TSUpr1-pEcad-Luc cells were infected with 30 luciferase-positive microRNAs (see text). Total RNA was reverse-transcribed, and used for SYBR Green real-time PCR analysis of the CDH1 (Ecad), CDH2 (Ncad), SNAI1, SNAI2, ZEB1 and ZEB2 genes. LUC, induction of FLuc/RLuc ratio, average of 3 experiments; CDH1, (induction of) endogenous CDH1 expression; CDH2, (inhibition of) endogenous CDH2 expression; Repesser, CDH1 transcriptional repressers that were down regulated at least 2-fold, or between 1.3 and 2-fold (underlined). Only data for 12 microRNAs that are of interest for further studies are shown; see text for a detailed reasoning of selecting these 12 miRs.

| miRNA | LUC | CDH1 | CDH2 | CDH1/CDH2 | Repressor |
|---|---|---|---|---|---|
| miR-124-1 | 1.76 | 1.30 | 2.46 | 0.53 | SNAI2 |
| miR-181a-1 | 1.59 | 4.22 | 0.89 | 4.74 | SNAI2 |
| miR-141 | 1.95 | 0.58 | 0.04 | 14.45 | ZEB2, SNAI1 |
| miR-200a | 1.66 | 2.18 | 0.67 | 3.25 | ZEB2 |
| miR-200c | 2.53 | 0.71 | 0.04 | 17.65 | ZEB2, ZEB1 |
| miR-205 | 1.79 | 0.39 | 0.08 | 4.86 | ZEB2 |
| miR-429 | 1.50 | 3.39 | 0.41 | 8.28 | ZEB2 |
| miR-206 | 1.73 | 2.24 | 2.07 | 1.08 | SNAI2 |
| miR-518b | 1.62 | 3.09 | 1.67 | 1.85 | SNAI2 |
| miR-520f | 1.43 | 12.92 | 1.16 | 11.14 | SNAI2, ZEB2 |
| miR-524 | 1.57 | 1.60 | 0.45 | 3.56 | ZEB2 |
| miR-200b | 2.08 | 5.17 | 1.18 | 4.38 | ZEB2 |

TABLE 2

Precursor sequences of miRNAs identified in MET screening (see table 1) List of miRNA precursor sequences (5' to 3' direction). All sequences were obtained from miRBase (release 14: Sep. 2009; www.mirbase.org).

| SEQ ID | miRNA | Precursor sequence |
|---|---|---|
| 22 | miR-124-1 | AGGCCUCUCUCUCCGUGUUCACAGCGGACCUUGAUUUAAAUGUC CAUACAAUUAAGGCACGCGGUGAAUGCCAAGAAUGGGGCUG |
| 23 | miR-124-2 | AUCAAGAUUAGAGGCUCUGCUCUCCGUGUUCACAGCGGACCUUGAU UUAAUGUCAUACAAUUAAGGCACGCGGUGAAUGCCAAGAGCGGAGC CUACGGCUGCACUUGAA |
| 24 | miR-124-3 | UGAGGGCCCCUCUGCGUGUUCACAGCGGACCUUGAUUUAAUGUCUA UACAAUUAAGGCACGCGGUGAAUGCCAAGAGAGGCGCCUCC |
| 25 | miR-181a-1 | UGAGUUUUGAGGUUGCUUCAGUGAACAUUCAACGCUGUCGGUGAGU UUGGAAUUAAAAUCAAAACCAUCGACCGUUGAUUGUACCCUAUGGC UAACCAUCAUCUACUCCA |

TABLE 2-continued

Precursor sequences of miRNAs identified in MET screening (see table 1) List of miRNA precursor sequences (5' to 3' direction). All sequences were obtained from miRBase (release 14: Sep. 2009; www.mirbase.org).

| SEQ ID | miRNA | Precursor sequence |
|---|---|---|
| 26 | miR-141 | CGGCCGGCCCUGGGUCCAUCUUCCAGUACAGUGUUGGAUGGUCU AAUUGUGAAGCUCCUAACACUGUCUGGUAAAGAUGGCUCCCGGGUG GGUUC |
| 27 | miR-200a | CCGGGCCCCUGUGAGCAUCUUACCGGACAGUGCUGGAUUUCC CAGCUUGACUCUAACACUGUCUGGUAACGAUGUUCAAAGGUGA CCCGC |
| 28 | miR-200c | CCCUCGUCUUACCCAGCAGUGUUUGGGUGCGGUUGGGAGUCUC UAAUACUGCCGGGUAAUGAUGGAGG |
| 29 | miR-205 | AAAGAUCCUCAGACAAUCCAUGUGCUUCUCUUGUCCUUCAUUCC ACCGGAGUCUGUCUCAUACCCAACCAGAUUUCAGUGGAGUGA AGUUCAGGAGGCAUGGAGCUGACA |
| 30 | miR-429 | GCGUCUUACCAGACAUGGUUAGACCUGGCCCUCUGUCUAAUAC UGUCUGGUAAAACCGUCCAUCCGCUGC |
| 31 | miR-206 | UGCUUCCCGAGGCCACAUGCUUCUUUAUAUCCCCAUAUGGAUU ACUUUGCUAUGGAAUGUAAGGAAGUGUGUGGUUUCGGCAAGUG |
| 32 | miR-518b | UCAUGCUGUGGCCCUCCAGAGGGAAGCGCUUUCUGUUGUCUGAAAG AAAACAAAGCGCUCCCCUUUAGAGGUUUACGGUUUGA |
| 33 | miR-520f | UCUCAGGCUGUGACCCUCUAAAGGGAAGCGCUUUCUGUGGU CAGAAAGAAAAGCAAGUGCUUCCUUUUAGAGGGUUACCGUUU GGGA |
| 34 | miR-524 | UCUCAUGCUGUGACCCUACAAAGGGAAGCACUUUCUCUUGUCCAAA GGAAAAGAAGGCGCUUCCCUUUGGAGUGUUACGGUUUGAGA |
| 35 | miR-200b | CCAGCUCGGGCAGCCGUGGCCAUCUUACUGGGCAGCAUUGGAUGGA GUCAGGUCUCUAAUACUGCCUGGUAAUGAUGACGGCGGAGCCCUGC ACG |

TABLE 3

Mature sequences of miRNAs identified in MET screening (see table 1) List of mature miRNA sequences (5' to 3' direction). All sequences were obtained from miRBase (release 14: Sep. 2009; www.mirbase.org).

| microRNA | mature miRNA | SEQ ID | SEQ mature miRNA |
|---|---|---|---|
| hsa-miR-124-1 hsa-miR-124-2 hsa-miR-124-3 | miR-124 miR-124* | 2 3 | uaaggcacgcggugaaugcc cguguucacagcggaccuugau |
| hsa-miR-181a-1 | miR-181a miR-181a* | 4 5 | aacauucaacgcugucggugagu accaucgaccguugauuguacc |
| hsa-miR-141 | miR-141 miR-141* | 6 7 | uaacacugucugguaaagaugg caucuuccaguacaguguugga |
| hsa-miR-200a | miR-200a miR-200a* | 8 9 | uaacacugucugguaacgaugu caucuuaccggacagugcugga |
| hsa-miR-200b | miR-200b miR-200b* | 10 11 | uaauacugccugguaaugauga caucuuacugggcagcauugga |
| hsa-miR-200c | miR-200c miR-200c* | 12 13 | uaauacugccggguaaugaugga cgucuuacccagcaguguugg |
| hsa-miR-205 | miR-205 miR-205* | 14 15 | uccuucauuccaccggagucug gauuucaguggagugaaguuc |
| hsa-miR-429 | miR-429 | 16 | uaauacugucugguaaaaccgu |
| hsa-miR-206 | miR-206 | 17 | uggaauguaaggaagugugugg |
| hsa-miR-518b | miR-518b | 18 | caaagcgcuccccuuuagaggu |
| hsa-miR-520f | miR-520f | 19 | aagugcuuccuuuuagagggu |
| hsa-miR-524 | miR-524-5p miR-524-3p | 20 21 | cuacaaagggaagcacuuucuc gaaggcgcuucccuuuggagu |

TABLE 4

Sequences of miRNAs identified in MET screening as cloned in lentiviral vectors (see table 1)

| Seq ID | miRNA | Cloned sequence in lentiviral vector |
|---|---|---|
| 36 | miR-124-1 | TTTCTTTCACCTTTCCTTCCTTCCTTCCTCCTTTCCTTCCTCAGGAGAA AGGCCTCTCTCTCCGTGTTCACAGCGGACCTTGATTTAAATGTCCATA CAATTAAGGCACGCGGTGAATGCCAAGAATGGGGCTGGCTGAGCA CCGTGGGTCGGCGAGGGCCCGCCAAGGAAGGAGCGACC |
| 37 | miR-181a-1 | GTTGTTTCTGTCTCCCATCCCCTTCAGATACTTACAGATACTGTAAAG TGAGTAGAATTCTGAGTTTTGAGGTTGCTTCAGTGAACATTCAACGCT GTCGGTGAGTTTGGAATTAAAATCAAAACCATCGACCGTTGATTGTAC CCTATGGCTAACCATCATCTACTCCATGGTGCTCAGAATTCGCTGAAG ACAGGAAACCAAA |
| 38 | miR-141 | CCTGTAGCAACTGGTGAGCGCGCACCGTAGTTCTCTGTCGGCCGGCC CTGGGTCCATCTTCCAGTACAGTGTTGGATGGTCTAATTGTGAAGCTC CTAACACTGTCTGGTAAAGATGGCTCCCGGGTGGGTTCTCTCGGCAGT AACCTTCAGGGAGCCCTGAAGACCATGGAGGACTACTGACCAACAA CCTCTGACCTT |
| 39 | miR-200a | GTTCTTCCCTGGGCTTCCACAGCAGCCCCTGCCTGCCTGGCGGGACC CCACGTCCCTCCCGGGCCCCTGTGAGCATCTTACCGGACAGTGCTGG ATTTCCCAGCTTGACTCTAACACTGTCTGGTAACGATGTTCAAAGGTG ACCCGCCGCTCGCCGGGGACACCACCGAGGCACATCCGGAGCTCCTACT |
| 40 | miR-200c | AAGCTGCCTGACCCAAGGTGGGCGGGCTGGGCGGGGCCCTCGTCT TACCCAGCAGTGTTTGGGTGCGGTTGGGAGTCTCTAATACTGCCGGG TAATGATGGAGGCCCCTGTCCCTGTGTCAGCAACATCCATCGCCTCA |
| 41 | miR-205 | AGTGTCTACAGGCTGAGGTTGACATGCATCCCCACCCTCTGAGAAAAA GATCCTCAGACAATCCATGTGCTTCTCTTGTCCTTCATTCCACCGGAGT CTGTCTCATACCCAACCAGATTTCAGTGGAGTGAAGTTCAGGAGGCAT GGAGCTGACAACCATGAGGCCTCGGCAGCCACCGCCACCACCGCCGC CGCCACCACCGTAGCAGCAGCAGCAGCAGCAGCAGCAGCAGCAGCA GCAGCAAGAGTAACT |
| 42 | miR-429 | AGACACCAGCCCAGGACCCGGAGGCCACCCACACCACCGCCGGCCGA TGGGCGTCTTACCAGACATGGTTAGACCTGGCCCTCTGTCTAATACTGT CTGGTAAAACCGTCCATCCGCTGCCTGATCACCGTTAGAGGAGAGAGC TGCCTGCCCTGCAGCTCATCAGTGCAAAGCC |
| 43 | miR-206 | GCAAGGAGGAAAGATGCTACAAGTGGCCCACTTCTGAGATGCGGGCT GCTTCTGGATGACACTGCTTCCCGAGGCCACATGCTTCTTTTATATCCC CATATGGATTACTTTGCTATGGAATGTAAGGAAGTGTGTGGTTTCGGC AAGTGCCTCCTCGCTGGCCCCAGGGTACCACCCGGAGCACAGGTTTG GTGACCTTCTTC |
| 44 | miR-518b | GCAAACAGGGCAAATAAATGCATCTTTATTTTGTGTCCATTTTAACCT GGTCAAGGAAAATTCCAACAGCAACATCAAAAAACCAGTGTTGGAG CAAGAATATGTCATGCTGTGGCCCTCCAGAGGGAAGCGCTTTCTGTT GTCTGAAAGAAAACAAAGCGCTCCCCTTTAGAGGTTTACGGTTTGAG TAAAGCAGCGTTGAAGTTGATGCTGATCTTGGTAATACATTTGCAGA GCGTGCTTATCATCAG |
| 45 | miR-520f | TGTGTCCATTTAAACCTGGTCAAGGAAGATTCCCACAAAAAATCCAC GGTGCTGGAGCAAGAGGATCTCAGGCTGTGACCCTCTAAAGGGAA GCGCTTTCTGTGGTCAGAAAGAAAAGCAAGTGCTTCCTTTTAGAGG GTTACCGTTTGGGAAAAGCAATGTTGAAGTTGATGCTGATCTTGGT AAAATATTTGCAGAGCGTGCTTATCATCAG |
| 46 | miR-524 | CAAACAGGGCCAATAAATGCATCCTCATTTTTGTGTCCATTTTAACCT GGGCAAGGAAAATTCCAACAAAAAACCCAGAGTTCTGGAGCAAGAA GATCTCATGCTGTGACCCTACAAAGGGAAGCACTTTCTCTTGTCCAA AGGAAAAGAAGGCGCTTCCCTTTGGAGTGTTACGGTTTGAGAAAAG CAGCGTTGAAGTTGATGCTTATCTCGGTAATACATTTGTAGAGCATG CTTATCATGAGGCTTGGAC |
| 47 | miR-200b | CAGCCGGGCGGCCCCCGGACCCAGCTCGGGCAGCCGTGGCCATCTT ACTGGGCAGCATTGGATGGAGTCAGGTCTCTAATACTGCCTGGTAAT GATGACGGCGGAGCCCTGCACGCAGCGACCGGCCGACCCCGT |

TABLE 5

Seed sequences of miRNAs identified in MET screening (see Table 1) List of miRNA seed sequences (5' to 3' direction). All sequences were obtained from miRBase (release 14: Sep. 2009; www.mirbase.org). Seed sequence is defined as nucleotide 2-8 (5' to 3' direction) of the mature miRNA sequence.

| microRNA | mature miRNA | SEQ ID | Seed sequence |
|---|---|---|---|
| hsa-miR-124-1 | miR-124 | 87 | aaggcac |
| hsa-miR-124-2 | miR-124* | 88 | guguuca |
| hsa-miR-124-3 | | | |
| hsa-miR-181a-1 | miR-181a | 89 | acauuca |
| | miR-181a* | 90 | ccaucga |
| hsa-miR-141 | miR-141 | 91 | aacacug |
| | miR-141* | 92 | aucuucc |
| hsa-miR-200a | miR-200a | 93 | aacacug |
| | miR-200a* | 94 | aucuuac |
| hsa-miR-200b | miR-200b | 95 | aauacug |
| | miR-200b* | 96 | aucuuac |
| hsa-miR-200c | miR-200c | 97 | aauacug |
| | miR-200c* | 98 | gucuuac |
| hsa-miR-205 | miR-205 | 99 | ccuucau |
| | miR-205* | 100 | auuucag |
| hsa-miR-429 | miR-429 | 101 | aauacug |
| hsa-miR-206 | miR-206 | 102 | ggaaugu |
| hsa-miR-518b | miR-518b | 103 | aaagcgc |
| hsa-miR-520f | miR-520f | 104 | agugcuu |
| | | 105 | aagugcu |
| hsa-miR-524 | miR-524-5p | 106 | uacaaag |
| | miR-524-3p | 107 | aaggcgc |

TABLE 6

IsomiR sequences of miRNAs identified in screening (see Table 1) These isomiRs have been detected after the analysis of 66 human tissue samples using high-throughput deep sequencing and only isomiRs that represent >5% of the total number of cloned sequences are listed here, unless otherwise indicated.

| miRNA | Mature miRNA | Seed (SEQ ID) | IsomiR sequence (SEQ ID) |
|---|---|---|---|
| hsa-miR-520f | mir-520f | AGUGCUU (104) | AAGUGCUUCCUUUUAGAGGGU (118) |
| | | AAGUGCU (105) | AAGUGCUUCCUUUUAGAGGGUU*[1] (119) |
| | | | CAAGUGCUUCCUUUUAGAGGGU (120) |
| hsa-miR-518b | mir-518b | AAAGCGC (103) | CAAAGCGCUCCCCUUUAGAGGU (121) |
| | | | CAAAGCGCUCCCCUUUAGAGG (122) |
| | | | CAAAGCGCUCCCCUUUAGAG (123) |
| hsa-miR-524 | mir-524-3p | AAGGCGC (107) | GAAGGCGCUUCCCUUUGGAGUG (124) |
| | | | GAAGGCGCUUCCCUUUGGAGU (125) |
| | mir-524-5p | UACAAAG (106) | CUACAAAGGGAAGCACUUUCU (126) |
| | | | CUACAAAGGGAAGCACUUUCUC (127) |
| | | | CUACAAAGGGAAGCACUUUC (128) |
| hsa-miR-124-1 | mir-124 | AAGGCAC (87) | UAAGGCACGCGGUGAAUGCCAA (129) |
| hsa-miR-124-2 | | | UAAGGCACGCGGUGAAUGCCA (130) |
| hsa-miR-124-3 | | | UAAGGCACGCGGUGAAUGC (131) |
| | | | UAAGGCACGCGGUGAAUGCC*[3] (132) |
| hsa-miR-206 | mir-206 | GGAAUGU (102) | UGGAAUGUAAGGAAGUGUGUGG (133) |
| | | | UGGAAUGUAAGGAAGUGUGUGGU (134) |
| | | | UGGAAUGUAAGGAAGUGUGUG (135) |
| hsa-miR-181a-1 | mir-181a | ACAUUCA (89) | AACAUUCAACGCUGUCGGUGAGUUU (136) |
| | | | AACAUUCAACGCUGUCGGUGAGU (137) |
| | | | AACAUUCAACGCUGUCGGUGAG (138) |
| | | | AACAUUCAACGCUGUCGGUGAGUU (139) |
| | | | AACAUUCAACGCUGUCGG (140) |
| | | | AACAUUCAACGCUGUCGGU (141) |
| | | | AACAUUCAACGCUGUCGGUG (142) |
| | | | AACAUUCAACGCUGUCGGUGA (143) |
| hsa-miR-141 | mir-141 | AACACUG (91) | UAACACUGUCUGGUAAAGAUGG (144) |
| | | | UAACACUGUCUGGUAAAGAUG (145) |
| | | | UAACACUGUCUGGUAAAGAUGGC (146) |
| | | | UAACACUGUCUGGUAAAGAU (147) |
| | | | UAACACUGUCUGGUAAAGA (148) |
| | | | UAACACUGUCUGGUAAAGAUGGCU (149) |

TABLE 6-continued

IsomiR sequences of miRNAs identified in screening (see Table 1)
These isomiRs have been detected after the analysis of 66 human tissue samples using
high-throughput deep sequencing and only isomiRs that represent >5% of the total
number of cloned sequences are listed here, unless otherwise indicated.

| miRNA | Mature miRNA | Seed (SEQ ID) | IsomiR sequence (SEQ ID) |
|---|---|---|---|
| hsa-miR-200a | mir-200a | AACACUG (93) | UAACACUGUCUGGUAACGAUGUU (150) |
|  |  |  | UAACACUGUCUGGUAACGAUGU (151) |
| hsa-miR-200b | mir-200b | AAUACUG (95) | UAAUACUGCCUGGUAAUGAUGAC (152) |
|  |  |  | UAAUACUGCCUGGUAAUGAUGA (153) |
|  | mir-200b* | AUCUUAC (96) | CAUCUUACUGGGCAGCAUUGGA (154) |
|  |  |  | CAUCUUACUGGGCAGCAUUGG (155) |
| hsa-miR-200c | mir-200c | AAUACUG (97) | UAAUACUGCCGGGUAAUGAUGGA (156) |
|  |  |  | UAAUACUGCCGGGUAAUGAUGG (157) |
| hsa-miR-205 | mir-205 | CCUUCAU (99) | UCCUUCAUUCCACCGGAGUCU (158) |
|  |  |  | UCCUUCAUUCCACCGGAGUCUG (159) |
|  |  |  | UCCUUCAUUCCACCGGAGUCUGU (160) |
| hsa-miR-429 | mir-429 | AAUACUG (101) | UAAUACUGUCUGGUAAAACCGU (161) |
|  |  |  | UAAUACUGUCUGGUAAAACCG (162) |

*[1] miRBase-annotated sequence. Not detected in the deep-sequencing analysis
*[2] Only 0.9% of the total number of cloned sequences
*[3] Only 0.7% of the total number of cloned sequences

TABLE 7

List of microRNA mimics used for validation of MET screening results. Suppliers and product codes for all synthetic miR precursors are shown. All listed mimics are double stranded, with each strand having a 100% complementary alignment with each other. One strand will be the exact sequence of the mature miRNA sequences as deposited in miRBase and listed in table 3. The other strand contains certain modifications.

| miRNA mimic | Supplier | Product code |
|---|---|---|
| Mimic Negative Control #1** | Dharmacon* | CN-001000-01-05 |
| hsa-miR-200c miRIDIAN Mimic | Dharmacon | C-300646-05-0005 |
| hsa-miR-520f miRIDIAN Mimic | Dharmacon | C-300779-03-0005 |
| hsa-miR-524-5p miRIDIAN Mimic | Dharmacon | C-300806-03-0005 |
| hsa-miR-518b miRIDIAN Mimic | Dharmacon | C-300798-03-0005 |
| hsa-miR-124 Pre-miR precursor | Ambion | PM10691 |
| hsa-miR-124* Pre-miR precursor | Ambion | PM11154 |
| hsa-miR-181a Pre-miR precursor | Ambion | PM10421 |
| hsa-miR-181a* Pre-miR precursor | Ambion | PM10381 |
| hsa-miR-200c Pre-miR precursor | Ambion | PM11714 |
| hsa-miR-206 Pre-miR precursor | Ambion | PM10409 |

*Dharmacon is now part of Thermo Fisher Scientific.
**This negative control is based on C. Elegans Cel-miR-67 (Seq ID 163).

TABLE 8

Gene expression in inducible microRNA transfected PC3 cells.
PC3-Tet-on (clone 8) cells were stably transfected with pmRi-ZsGreen1-miR-X expression plasmids. Selected clones (see FIG. 5) were treated with 1 μg/ml DOX for 4 days. Total RNA was isolated and gene expression was studied by qPCR.

| Gene | PC3-mRi-miR-200c | PC3-mRi-miR-520f |
|---|---|---|
| CDH1 | = | Up * |
| CDH2 | Weakly expressed | Weakly expressed |
| CDH11 | Down * | Down |
| VIM | Down | n.d. |
| ZEB1 | Down | Down |
| ZEB2 | Down | = |
| SNAI1 | = | = |
| SNAI2 | Down | Down |

* more than 1.5-fold;
=, no change;
n.d., not determined.

REFERENCE LIST

1. Tomita, K., van, B. A., van Leenders, G. J., Ruijter, E. T., Jansen, C. F., Bussemakers, M. J., and Schalken, J. A. Cadherin switching in human prostate cancer progression. *Cancer Res.* 60: 3650-3654 (2000).
2. Umbas, R., Isaacs, W. B., Bringuier, P. P., Schaafsma, H. E., Karthaus, H. F., Oosterhof, G. O., Debruyne, F. M., and Schalken, J. A. Decreased E-cadherin expression is associated with poor prognosis in patients with prostate cancer. *Cancer Res.* 54: 3929-3933 (1994).
3. Oort van, I., Tomita, K., van, B. A., Bussemakers, M. J., Kiemeney, L. A., Karthaus, H. F., Witjes, J. A., and Schalken, J. A. The prognostic value of E-cadherin and the cadherin-associated molecules alpha-, beta-, gamma-catenin and p120ctn in prostate cancer specific survival: a long-term follow-up study. *Prostate.* 67: 1432-1438 (2007).
4. Batlle, E., Sancho, E., Franci, C., Dominguez, D., Monfar, M., Baulida, J., and Garcia, D. H. The transcription factor snail is a repressor of E-cadherin gene expression in epithelial tumour cells. *Nat. Cell Biol.* 2: 84-89 (2000).
5. Cano, A., Perez-Moreno, M. A., Rodrigo, I., Locascio, A., Blanco, M. J., del Barrio, M. G., Portillo, F., and Nieto, M.

A. The transcription factor snail controls epithelial-mesenchymal transitions by repressing E-cadherin expression. *Nat. Cell Biol.* 2: 76-83 (2000).
6. Hajra, K. M., Chen, D. Y., and Fearon, E. R. The SLUG zinc-finger protein represses E-cadherin in breast cancer. *Cancer Res.* 62: 1613-1618 (2002).
7. Yang, J., Mani, S. A., Donaher, J. L., Ramaswamy, S., Itzykson, R. A., Come, C., Savagner, P., Gitelman, I., Richardson, A., and Weinberg, R. A. Twist, a master regulator of morphogenesis, plays an essential role in tumor metastasis. *Cell* 117: 927-939 (2004).
8. Bussemakers, M. J., Giroldi, L. A., van Bokhoven, A., and Schalken, J. A. Transcriptional regulation of the human E-cadherin gene in human prostate cancer cell lines: characterization of the human E-cadherin gene promoter. *Biochem. Biophys. Res. Commun.* 203: 1284-1290 (1994).
9. Giroldi, L. A., Bringuier, P. P., de Weijert, M., Jansen, C., van Bokhoven, A., and Schalken, J. A. Role of E boxes in the repression of E-cadherin expression. *Biochem. Biophys. Res. Commun.* 241: 453-458 (1997).
10. Rodrigo, I., Cato, A. C. B., and Cano, A. Regulation of E-cadherin gene expression during tumor progression: the role of a new Ets-binding site and the E-pal element. *Exp. Cell Res.* 248: 358-371 (1999).
11. Conacci-Sorrell, M., Simcha, I., Ben Yedidia, T., Blechman, J., Savagner, P., and Ben Ze'ev, A. Autoregulation of E-cadherin expression by cadherin-cadherin interactions: the roles of beta-catenin signaling, Slug, and MAPK. *J. Cell Biol.* 163: 847-857 (2003).
12. Gregory, P. A., Bracken, C. P., Bert, A. G., and Goodall, G. J. MicroRNAs as regulators of epithelial-mesenchymal transition. *Cell Cycle.* 7: 3112-3118 (2008).
13. Burk, U., Schubert, J., Wellner, U., Schmalhofer, O., Vincan, E., Spaderna, S., and Brabletz, T. A reciprocal repression between ZEB1 and members of the miR-200 family promotes EMT and invasion in cancer cells. *EMBO Rep.* 9: 582-589 (2008).
14. Gregory, P. A., Bert, A. G., Paterson, E. L., Barry, S. C., Tsykin, A., Farshid, G., Vadas, M. A., Khew-Goodall, Y., and Goodall, G. J. The miR-200 family and miR-205 regulate epithelial to mesenchymal transition by targeting ZEB1 and SIP1. *Nat. Cell Biol.* 10: 593-601 (2008).
15. Park, S. M., Gaur, A. B., Lengyel, E., and Peter, M. E. The miR-200 family determines the epithelial phenotype of cancer cells by targeting the E-cadherin repressors ZEB1 and ZEB2. *Genes Dev.* 22: 894-907 (2008).
16. Berezikov, E., van, T. G., Verheul, M., van de, B. J., van, L. L., Vos, J., Verloop, R., van de, W. M., Guryev, V., Takada, S., van Zonneveld, A. J., Mano, H., Plasterk, R., and Cuppen, E. Many novel mammalian microRNA candidates identified by extensive cloning and RAKE analysis. *Genome Res.* 16: 1289-1298 (2006).
17. Lowery, A. J., Miller, N., Devaney, A., McNeill, R. E., Davoren, P. A., Lemetre, C., Benes, V., Schmidt, S., Blake, J., Ball, G., and Kerin, M. J. MicroRNA signatures predict oestrogen receptor, progesterone receptor and HER2/neu receptor status in breast cancer. *Breast Cancer Res.* 11: R27 (2009).
18. Pfaffl, M. W. A new mathematical model for relative quantification in real-time RT-PCR. *Nucleic Acids Res.* 29: e45 (2001).
19. Chen, C., Ridzon, D. A., Broomer, A. J., Zhou, Z., Lee, D. H., Nguyen, J. T., Barbisin, M., Xu, N. L., Mahuvakar, V. R., Andersen, M. R., Lao, K. Q., Livak, K. J., and Guegler, K. J. Real-time quantification of microRNAs by stem-loop RT-PCR. *Nucleic Acids Res.* 33: e179 (2005).
20. Batlle, E., Sancho, E., Franci, C., Dominguez, D., Monfar, M., Baulida, J., and Garcia, D. H. The transcription factor snail is a repressor of E-cadherin gene expression in epithelial tumour cells. *Nat. Cell Biol.* 2: 84-89 (2000).
21. Cano, A., Perez-Moreno, M. A., Rodrigo, I., Locascio, A., Blanco, M. J., del Barrio, M. G., Portillo, F., and Nieto, M. A. The transcription factor snail controls epithelial-mesenchymal transitions by repressing E-cadherin expression. *Nat. Cell Biol.* 2: 76-83 (2000).
22. Hajra, K. M., Chen, D. Y., and Fearon, E. R. The SLUG zinc-finger protein represses E-cadherin in breast cancer. *Cancer Res.* 62: 1613-1618 (2002).
23. Yang, J., Mani, S. A., Donaher, J. L., Ramaswamy, S., Itzykson, R. A., Come, C., Savagner, P., Gitelman, I., Richardson, A., and Weinberg, R. A. Twist, a master regulator of morphogenesis, plays an essential role in tumor metastasis. *Cell* 117: 927-939 (2004).
24. Bussemakers, M. J., Giroldi, L. A., van Bokhoven, A., and Schalken, J. A. Transcriptional regulation of the human E-cadherin gene in human prostate cancer cell lines: characterization of the human E-cadherin gene promoter. *Biochem. Biophys. Res. Commun.* 203: 1284-1290 (1994).
25. Giroldi, L. A., Bringuier, P. P., de Weijert, M., Jansen, C., van Bokhoven, A., and Schalken, J. A. Role of E boxes in the repression of E-cadherin expression. *Biochem. Biophys. Res. Commun.* 241: 453-458 (1997).
26. Rodrigo, I., Cato, A. C. B., and Cano, A. Regulation of E-cadherin gene expression during tumor progression: the role of a new Ets-binding site and the E-pal element. *Exp. Cell Res.* 248: 358-371 (1999).
27. Conacci-Sorrell, M., Simcha, I., Ben Yedidia, T., Blechman, J., Savagner, P., and Ben Ze'ev, A. Autoregulation of E-cadherin expression by cadherin-cadherin interactions: the roles of beta-catenin signaling, Slug, and MAPK. *J. Cell Biol.* 163: 847-857 (2003).
28. Bussemakers, M. J., van, B. A., Tomita, K., Jansen, C. F., and Schalken, J. A. Complex cadherin expression in human prostate cancer cells. *Int. J. Cancer.* 85: 446-450 (2000).
29. Mohanty, S., and Xu, L. Experimental metastasis assay. *J. Vis. Exp.* 1942 (2010).
30. Rubio, N., Villacampa, M. M., El, H. N., and Blanco, J. Metastatic burden in nude mice organs measured using prostate tumor PC-3 cells expressing the luciferase gene as a quantifiable tumor cell marker. *Prostate.* 44: 133-143 (2000).
31. Fukuchi, K., Steiniger, S. C., Deryugina, E., LIU, Y., Lowery, C. A., Gloeckner, C., Zhou, B., Kaufmann, G. F., Quigley, J. P., and Janda, K. D. Inhibition of tumor metastasis: functional immune modulation of the CUB domain containing protein 1. *Mol. Pharm.* 7: 245-253 (2010).

ABBREVIATIONS

CDH1—E-cadherin
CDH2—N-cadherin
CDH11—OB-cadherin
CTG—CEllTiter-GLO (cell viability assay)
DOX—Doxycycline
EMT—epithelial to mesenchymal transition
miR—microRNA
MET—mesenchymal to epithelial transition
MOI—multiplicity of infection
MTT—(3-(4,5-Dimethylthiazol-2-yl)-2,5-diphenyltetrazolium bromide
qPCR—quantitative PCR
PCa—prostate cancer SNAI1—SNAIL homolog 1, alias SNAIL
SNAI2—SNAIL homolog 2, alias SLUG
TSU—TSUpr1-pEcad-Luc cells
UBC—urinary bladder cancer VIM—vimentin
ZEB1—zinc finger E-box binding homeobox 1, alias deltaEF1
ZEB2—zinc finger E-box binding homeobox 2, alias SIP1

The invention claimed is:

1. A method of treating a patient having a bladder and/or a prostate cancer, said treatment comprising administering a composition comprising an effective amount of a mature miRNA molecule comprising a minimum length of 6 nucleotides and a maximum length of 50 nucleotides, comprising at least 6 of the 7 nucleotides present in a seed sequence selected from the group consisting of SEQ ID NO: 103-107, and comprising at least 80% identity with a sequence selected from the group consisting of SEQ ID NO: 18-21 and 118-128; wherein said treatment results in amelioration of a symptom of said cancer.

2. The method of claim 1, wherein said miRNA molecule comprises at least 90% identity.

3. The method of claim 1 wherein said miRNA molecule is a minimum of 10 nucleotides in length.

4. The method of claim 1, wherein said miRNA molecule is a minimum of 30 nucleotides in length.

5. The method of claim 1, wherein said patient has a solid epithelial tumor, and wherein said amelioration comprises a decrease of proliferation of said tumor cells and/or an increase in said tumor cell death.

6. The method of claim 1, wherein said treatment further comprises chemotherapy, radiotherapy and/or surgery.

7. The method according to claim 1, wherein said miRNA molecule comprises a miRNA-518b, miRNA-520f and/or miRNA-524.

8. The method of claim 1, wherein 0.1 to 5 mg/kg/day of the miRNA molecule is administered to the patient.

9. The method of claim 1, wherein the miRNA molecule comprises a nucleotide analogue.

10. A method of treating a patient having a bladder and/or a prostate cancer, said treatment comprising administering a composition comprising an effective amount of a mature miRNA molecule comprising a minimum length of 6 nucleotides and a maximum length of 50 nucleotides, comprising at least 6 of the 7 nucleotides present in a seed sequence selected from the group consisting of SEQ ID NO: 103-107, and comprising at least 80% identity with a sequence selected from the group consisting of SEQ ID NO: 18-21 and 118-128; wherein said treatment results in amelioration of a symptom of said cancer, wherein a tumor of said patient comprises cells which exhibit decreased expression of the E-cadherin (CDH1) gene relative to a reference E-cadherin (CDH1) gene expression value.

11. A method of treating a patient having a bladder and/or a prostate cancer, said treatment comprising administering a composition comprising an effective amount of a mature miRNA molecule comprising a minimum length of 6 nucleotides and a maximum length of 50 nucleotides, comprising at least 6 of the 7 nucleotides present in a seed sequence selected from the group consisting of SEQ ID NO: 103-107, and comprising at least 80% identity with a sequence selected from the group consisting of SEQ ID NO: 18-21 and 118-128; wherein said treatment results in amelioration of a symptom of said cancer, wherein a tumor of said patient comprises cells which exhibit decreased expression of the E-cadherin (CDH1) gene relative to a reference E-cadherin-(CDH1) gene expression value, wherein said decreased expression of said E-cadherin gene comprises at least a 5% decrease relative to said reference value and/or at least a 1.5 fold decrease relative to said reference value.

12. A method of treating a patient having a bladder and/or a prostate cancer, said treatment comprising administering a composition comprising an effective amount of a mature miRNA molecule comprising a minimum length of 6 nucleotides and a maximum length of 50 nucleotides, comprising at least 6 of the 7 nucleotides present in a seed sequence selected from the group consisting of SEQ ID NO: 103-107, and comprising at least 80% identity with a sequence selected from the group consisting of SEQ ID NO: 18-21 and 118-128; wherein said treatment results in amelioration of a symptom of said cancer, wherein a tumor of said patient comprises cells which exhibit decreased expression of the E-cadherin (CDH1) gene relative to a reference E-cadherin-(CDH1) gene expression value, wherein said reference E-cadherin (CDH1) gene is a nontumor cell epithelial tissue gene.

13. A method of treating a patient having a bladder and/or prostate cancer, said treatment comprising administering a composition comprising an effective amount of
   a precursor of a miRNA molecule of 50-400 nucleotides having at least 80% identity with a sequence selected from the group consisting of SEQ ID NOs: 32-34 and 44-46; and
   a precursor of a miRNA molecule of 50-400 nucleotides having at least 80% identity with a sequence selected from the group consisting of SEQ ID NOs: 22-31, 35, 36-43 and 47; wherein said treatment results in amelioration of a symptom of said cancer.

14. The method of claim 13, wherein said precursor RNA identity is at last 99% or is 100%.

15. The method of claim 13, wherein said precursor RNA molecule is a minimum of 60 nucleotides.

16. The method of claim 13, wherein said precursor RNA molecule is no more than 200 nucleotides in length.

17. The method of claim 13, wherein the mature miRNA molecule comprises at least 80% identity with a sequence selected from the group consisting of SEQ ID NOs: 44-46.

18. A method of treating a patient having a bladder and/or a prostate cancer, said treatment comprising administering a composition comprising an effective amount of a mature miRNA molecule comprising a minimum length of 6 nucleotides and a maximum length of 50 nucleotides, comprising at least 6 of the 7 nucleotides present in a seed sequence selected from the group consisting of SEQ ID NO: 103-107, and comprising at least 80% identity with a sequence selected from the group consisting of SEQ ID NO: 18-21 and 118-128; wherein said treatment results in amelioration of a symptom of said cancer and wherein said composition further comprises another miRNA molecule, selected from: at least one of miRNA-124-1, miRNA-206, miRNA-181a-1, miRNA-141, miRNA-200a, miRNA-200b, miRNA-200c, miRNA-429 and miRNA-205.

19. A method of treating a patient suffering from fibrosis wherein fibrotic cells in said patient exhibit lower expression of E-Cadherin, increased expression of N-Cadherin, and increased expression of integrin $\alpha v \beta 3$, by administering a composition comprising an effective amount of a mature miRNA molecule comprising a minimum length of 6 nucleotides and a maximum length of 50 nucleotides, comprising at least 6 of the 7 nucleotides present in a seed sequence selected from the group consisting of SEQ ID NO: 103-107, and comprising at least 80% identity with a sequence selected from the group consisting of SEQ ID NO: 18-21 and 118-128, wherein said treatment results in a decrease in the number of said fibrotic cells.

20. A method of treating a patient having a bladder and/or prostate cancer, said treatment comprising administering a composition comprising an effective amount of:
  a mature miRNA molecule comprising a minimum length of 6 nucleotides and a maximum length of 50 nucleotides, comprising at least 6 of the 7 nucleotides present in a seed sequence selected from the group consisting of SEQ ID NO: 103-107, and/or comprising at least 80% identity with a sequence selected from the group consisting of SEQ ID NO: 18-21 and 118-128; and
  a mature miRNA molecule comprising a minimum length of 6 nucleotides and a maximum length of 50 nucleotides, comprising at least 6 of the 7 nucleotides present in a seed sequence selected from the group consisting of SEQ ID NO: 87-102 and/or comprising at least 80% identity with a sequence selected from the group consisting of SEQ ID NO: 2-17 and 129-162, wherein said treatment results in amelioration of a symptom of said cancer.

* * * * *